United States Patent
Melker et al.

(10) Patent No.: US 10,137,245 B2
(45) Date of Patent: Nov. 27, 2018

(54) CENTRAL SITE PHOTOPLETHYSMOGRAPHY, MEDICATION ADMINISTRATION, AND SAFETY

(75) Inventors: Richard J. Melker, Gainesville, FL (US); Donn M. Dennis, Gainesville, FL (US); Jeremy Melker, Gainesville, FL (US); Mark Rice, Gainesville, FL (US); Robert Hurley, Gainesville, FL (US); Mark Gold, Alachua, FL (US); Richard Allen, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 694 days.

(21) Appl. No.: 13/817,156

(22) PCT Filed: Aug. 8, 2011

(86) PCT No.: PCT/US2011/046943
§ 371 (c)(1),
(2), (4) Date: Jun. 6, 2013

(87) PCT Pub. No.: WO2012/024106
PCT Pub. Date: Feb. 23, 2012

(65) Prior Publication Data
US 2013/0276785 A1 Oct. 24, 2013

Related U.S. Application Data

(60) Provisional application No. 61/374,597, filed on Aug. 17, 2010, provisional application No. 61/438,620, (Continued)

(51) Int. Cl.
*A61M 16/01* (2006.01)
*A61M 16/10* (2006.01)
(Continued)

(52) U.S. Cl.
CPC ......... *A61M 5/1723* (2013.01); *A61B 5/0205* (2013.01); *A61B 5/14551* (2013.01);
(Continued)

(58) Field of Classification Search
CPC . A61B 5/14551; A61B 5/0205; A61B 5/4839; A61B 5/4821; A61B 5/002;
(Continued)

(56) References Cited

U.S. PATENT DOCUMENTS 4,944,485 A * 7/1990 Daoud ............... A61M 39/284
137/560
5,335,659 A * 8/1994 Pologe ............... A61B 5/02427
128/207.18
(Continued)

FOREIGN PATENT DOCUMENTS

| CA | 2508976 A1 | 7/2004 |
|---|---|---|
| CA | 2748541 A1 | 7/2010 |

OTHER PUBLICATIONS

U.S. Appl. No. 61/152,964, filed Feb. 16, 2009.*
(Continued)

*Primary Examiner* — Colin W Stuart
*Assistant Examiner* — Douglas Sul

(57) ABSTRACT

A monitoring and control system, apparatus and method for safe administration, reduction or cessation of administration of at least on medication, fluid or both, which includes at least one Central Source Site (CSS) Photoplethysmography (PPG) sensor coupled to means for control of delivery of the at least one medication, fluid or both.

11 Claims, 36 Drawing Sheets

Related U.S. Application Data filed on Feb. 1, 2011, provisional application No. 61/441,621, filed on Feb. 10, 2011.

(51) Int. Cl.
| | |
|---|---|
| *A61M 5/172* | (2006.01) |
| *A61M 5/142* | (2006.01) |
| *A61B 5/0205* | (2006.01) |
| *A61B 5/1455* | (2006.01) |
| *A61M 16/06* | (2006.01) |
| *A61M 16/16* | (2006.01) |
| *G06F 19/00* | (2018.01) |
| *A61M 5/168* | (2006.01) |
| *A61B 5/00* | (2006.01) |
| *A61B 5/024* | (2006.01) |
| *A61B 5/0402* | (2006.01) |
| *A61B 5/08* | (2006.01) |
| *A61B 5/083* | (2006.01) |
| *A61M 16/00* | (2006.01) |

(52) U.S. Cl.
CPC .......... *A61B 5/4839* (2013.01); *A61B 5/6803* (2013.01); *A61M 16/00* (2013.01); *A61M 16/0051* (2013.01); *A61M 16/026* (2017.08); *A61M 16/0666* (2013.01); *A61M 16/0677* (2014.02); *A61M 16/10* (2013.01); *A61M 16/161* (2014.02); *G06F 19/00* (2013.01); *G06F 19/3456* (2013.01); *G06F 19/3468* (2013.01); *A61B 5/002* (2013.01); *A61B 5/024* (2013.01); *A61B 5/0402* (2013.01); *A61B 5/0816* (2013.01); *A61B 5/0826* (2013.01); *A61B 5/0836* (2013.01); *A61B 5/4818* (2013.01); *A61B 5/4821* (2013.01); *A61B 5/7246* (2013.01); *A61M 2005/16863* (2013.01); *A61M 2016/0027* (2013.01); *A61M 2205/3368* (2013.01); *A61M 2230/04* (2013.01); *A61M 2230/205* (2013.01); *A61M 2230/432* (2013.01)

(58) Field of Classification Search
CPC ........ A61M 16/104; A61M 2016/1035; A61M 2230/04; A61M 5/1723; A61M 2005/1726; A61M 5/16813; A61M 5/116831; A61M 5/16836; A61M 5/16831; A61M 2005/16863

See application file for complete search history.

(56) References Cited

U.S. PATENT DOCUMENTS

| | | | |
|---|---|---|---|
| 2007/0010756 A1* | 1/2007 | Viertio-Oja | A61B 5/048 600/544 |
| 2007/0060874 A1* | 3/2007 | Nesbitt | A61M 5/14228 604/80 |
| 2008/0072906 A1* | 3/2008 | Starr | A61B 5/02007 128/204.23 |
| 2008/0083414 A1* | 4/2008 | Messerges | A61B 5/0205 600/301 |
| 2009/0005655 A1* | 1/2009 | Frank | A61B 5/0205 600/301 |
| 2009/0221986 A1* | 9/2009 | Wang | A61M 5/16877 604/503 |
| 2011/0137134 A1* | 6/2011 | Hemmerling | A61B 5/0205 600/301 |
| 2011/0137297 A1* | 6/2011 | Kiani | A61B 5/0205 604/890.1 |
| 2013/0276785 A1 | 10/2013 | Melker | |

OTHER PUBLICATIONS

Foreign search report dated Feb. 24, 2016 for CA application serial No. 2,808,379.

Foreign search report for CA 2,808,379 dated Jan. 6, 2017.

* cited by examiner

CENTRAL SITE PHOTOPLETHYSMOGRAPHY, MEDICATION ADMINISTRATION, AND SAFETY

CROSS-REFERENCE TO RELATED APPLICATION

This application is the 35 U.S.C. § 371 national stage of, and claims priority to and the benefit of, PCT application PCT/US2011/046943, filed Aug. 8, 2011, which claims priority to and the benefit of U.S. Application Nos. 61/374,597, filed 17 Aug. 2010 and of 61/438,620, filed 1 Feb. 2011, and of 61/441,621, filed 10 Feb. 2011, the disclosure of each of which is hereby incorporated by reference in their entirety.

FIELD OF THE INVENTION

Monitoring and control systems, apparatuses and methods for safe administration, reduction or cessation of administration of medications or fluids.

BACKGROUND OF THE INVENTION

The present invention provides a substantially medication agnostic method, system and device for enhancing the safety of delivering medications and/or fluids to subjects in need thereof. There are several related aspects of the invention by means of which this comprehensive and substantially medication agnostic safety system operates, but in general, the invention provides means for monitoring the combined effects of clinical interventions and a patient's underlying clinical condition and, based on such monitoring, provides a processed output to advise medical personnel of the need for modifying the intervention(s), or, in particular scenarios, automatically initiates alternate interventions to secure the safety of the subject. For example, and without limitation, for conscious sedation and administration of opioid and other drugs, including drugs which alone or in combination with other drugs, and/or the patient's clinical condition(s) cause or can cause respiratory depression, the present system, method and apparatus: (a) monitors subject breath rate, breathing effort, as well as, optionally, a plethora of other physiologic parameters, and (b) on detection of an adverse parameter based on algorithms and limits built into the system, advises medical personnel of the need for intervention and/or automatically intervenes to, for example, shut off or diminish delivery of the opioid or other medication, and initiates non-invasive positive pressure and/or ventilation to ensure that the patient is adequately oxygenated and ventilated. When used in a clinical setting, such as in an Intensive Care Unit (ICU), where the patient is already or could be intubated, ventilation could be modified accordingly, while still deriving the benefit of the additional information available from implementation of the present system.

To date, no commercially available closed-loop system or "advisory" system exists, at least in the United States, for administration of anesthetics (see Sahinovic et al., Current Opinion in Anesthesiology, 2010, 23:734-740; see also the American Society of Anesthesiologist's comments to the FDA respecting an Application for Premarket Approval for SEDASYS™ System by Ethicon Endo-Surgery, Inc. Docket No FDA-2009-N-0664; Meeting ID 2009-4438 before FDA's Anesthesiology and Respiratory Therapy Devices Panel of the Medical Devices Advisory Committee, publicly available at http://www.asahq.org/For-Members/Practice-Management/ASA-Practice-Management-Resources/ASA-Regulatory-Comment-Letters/ASA-Comments-to-the-FDA-regarding-SEDASYS.aspx). In one aspect of the present invention, a system, method and apparatus is provided which addresses the concerns expressed by the ASA before the FDA.

In a number of scenarios, it is possible to safely infuse subjects with pharmaceutically active agents or fluids. In other scenarios, for example where a subject is to be infused with an opioid, there remains substantial danger to the subject, unless they are closely monitored, and, even then, in the absence of the safety features provided by the present device, system and method, substantial risk remains. The present invention, therefore, provides a solution to this problem, which represents a long-term critical unmet medical need.

Conventional monitoring for respiratory depression in the hospital setting involves monitoring, for example, end tidal carbon-dioxide (ETCO2). However, ETCO2 monitoring is impractical in many scenarios. For example, it is difficult to measure in ambulatory patients (non-intubated patients). It is also costly, and the relevant equipment is cumbersome. The ability to directly monitor the pharmacodynamic (PD) effects of all of the factors that may contribute to hypopnea and/or apnea is far more valuable, for example, than knowing a single physiologic measurement, such as the ETCO2. Knowing the combined effects of $CO_2$, hypoxemia, opioids, other drugs, and physiologic state of a patient would provide much more valuable information for the patient's safety. Trending of various parameters would also be highly valuable, not only for closed-loop systems, but also for improved monitoring of patients in a hospital setting.

The present inventors have identified a number of technologies which may be adapted, as disclosed herein below in the detailed disclosure of the invention, for the particular purposes to be achieved by practice of the present invention. Thus, references to such technologies herein, and the documents in which those technologies are described, are to be considered as having been fully set forth herein.

For example, in U.S. Pat. No. 7,785,262B2, METHOD AND APPARATUS FOR DIAGNOSING RESPIRATORY DISORDERS AND DETERMINING THE DEGREE OF EXACERBATIONS, hereafter "the '262 patent", involves the identification of peaks and troughs in plethysmograph signals, preferably acquired from a central site location of a subject, such as the nasal ala(e), identifying midpoints or minima between peaks and troughs, and using an interpolated line to represent venous impedance, permits extracting of venous impedance and capacitance to thereby obtain an low frequency (or venous impedance) component signal indicative of respiratory rate and effort, inspiratory and/or expiratory times, thereby facilitating detection of an airway obstruction or cessation of breathing event (such as obstructive sleep or central apnea). Because the details of how that method is practiced is relevant here, we note that the '262 patent discloses and claims a method of monitoring respiration in a patient by securing a probe to a central source/sensing site of a patient to generate a plethysmography signal stream, and processing the signal stream received from the probe to obtain a venous impedance component signal. As disclosed in the '262 patent, the processing of the signal stream involves identifying peaks and troughs in the signal stream, identifying midpoints or minimum values between the peaks and troughs, and generating an interpolated line connecting the midpoints or minimum values which represents the venous impedance component. The thus identified venous impedance component is extracted from the signal stream to thereby obtain a separate arterial component signal and separate venous impedance component signal. This extraction and analysis algorithm makes it possible to observe changes in the venous impedance component signal which correlate with respiratory rate, inspiratory or expiratory events, or combinations of these events in a patient. The central source site is identified as preferably being selected from the group consisting of a nasal septum, a nasal alar, a pre- or post-auricular region, a cheek, or an ear canal of the patient. Applying the '262 technology in the present invention in the context of control of medication delivery provides a powerful method for monitoring a patient's respiratory rate, respiratory effort and associated parameters, to implement appropriate interventions as necessary, and as described in detail herein below. As disclosed further herein below, such a system may be integrated into the present system, method, and device for enhanced safety in providing certain types of treatment or therapy in particular contexts. In particular, for example, in providing opioid therapy via a closed loop or "advisory" system, integration of such technology into an infusion device, optionally including in a given embodiment, any one or a combination of (a) a means for providing positive pressure ventilation, whether, preferably, via a novel non-invasive patient ventilation apparatus as described in further detail herein below, or via a more invasive intubation ventilation interface such as those known in the art, (b) a means for occluding the delivery of the medication, (c) an accelerometer, or (d) other features disclosed herein; provides enhanced safety controls.

Likewise, with respect to published US patent application US2010/0192952, herein incorporated by reference, the present invention disclosure provides significant new applications and enhancements to the devices and methods disclosed therein. US2010/0192952 discloses certain pulse oximeter/plethysmography probes designed for securement to the nose, in a stand-alone form or incorporated into a mask of an air pilot or fire-fighter, pulse oximeter/plethysmography probes designed for securement to the pre-auricular portion of a subject's ear, to the ear canal of a subject's ear, to the post-auricular portion of the subject's ear, or to the cheek of a subject's face. All of these designs are incorporated by reference into this disclosure, with the key modifications of these probes as described herein below, and the key modifications to the methods and systems disclosed herein which facilitate the safe, effective and efficient open- or closed-loop delivery of appropriate medications to the subject, dependent on the analysis of PD and/or PK signals obtained from the subject, optionally including in a given embodiment, any one or a combination of (a) a means for providing positive pressure ventilation, (b) a means for occluding the delivery of the medication, (c) an accelerometer; (d) Self Monitoring and Reporting Technology, SMART, which provides an independent means for confirming dosage, time and identity of medication administered; (e) other features disclosed herein; provides enhanced safety controls.

The modifications and enhancement disclosed herein are likewise applicable to the context's disclosed in the U.S. Pat. Nos. 6,909,912, 7,024,235, and 7,127,278, i.e. to prevent Gravity-induced Loss of Consciousness (GLOC) or Almost Loss of Consciousness (ALOC), as well as, for example, in the context of the fire-fighter. The key enhancements disclosed herein for this purpose include either an integrated or separately housed infusion system as well as enhancements achieved by coupling PPG signal acquisition and processing to nasal pressure signal acquisition and processing. In the contexts of GLOC and ALOC, for example, the present invention provides the option not only of altering the G-force induced loss or almost loss of consciousness, by setting off an alarm or interfacing with an aircraft's onboard computer, but to also, or instead, provide the option of pharmacologic intervention, e.g. by detection of GLOC or ALOC and infusing the subject with an appropriate dose, for example, of glucose, epinephrine, institution of oxygen or increased flow of oxygen or the like, or combinations thereof, calculated to avert the potentially catastrophic sequelae of a loss of consciousness in these circumstances, optionally including in a given embodiment, any one or a combination of (a) a means for providing positive pressure ventilation, (b) a means for occluding the delivery of the medication, (c) an accelerometer, (d) SMART; (e) other features disclosed herein; provides enhanced safety controls.

Similarly, the technology described in Diab U.S. Pat. No. 6,157,850 (hereafter the '850 patent) provides, in particular with respect to blood oximetry measurements, methods, systems, algorithms and apparatuses to extract meaningful physiological information. Such a system may be integrated into the present method, device, system, to enhance safety by providing relevant pharmacodynamic (PD), pharmacokinetic (PK), or both PD and PK guided infusion in particular therapeutic contexts, optionally including in a given embodiment, any one or a combination of (a) a means for providing positive pressure ventilation, (b) a means for occluding the delivery of the medication, (c) an accelerometer, or (d) other features disclosed herein; provides enhanced safety controls.

U.S. Pat. No. 7,569,030 and related Medtronic MiniMed patents (see, e.g. U.S. Pat. No. 6,827,702, and U.S. Pat. No. 6,740,972) describes a system for delivery of insulin for control of physiological glucose concentration. In these patents, however, there is very little disclosure about the "sensing device for sensing a biological state" element even for a closed loop system for delivery of insulin. The only sensing device identified is one for measuring glucose concentration. The main thrust of these patents is a system for setting safety limits for the amount of insulin provided by an infusion pump, and the ability for the user to over-ride certain limits to simulate, for example, the body's "leading insulin secretion reflex". Other over-rides, to address medications or activity states (sleep, stress, etc), forms a central part of the disclosure. Methods for calculating delivery rates of an infusion formulation of insulin in response to a sensed glucose concentration are disclosed.

The need for dynamic modelling to control opioid administration has been recognized. See, for example, Mitsis et al., *J Appl Physiol.* 2009 April; 106(4):1038-49, "The effect of remifentanil on respiratory variability, evaluated with dynamic modelling", (hereafter, "Mitsis et al.) which noted that opioid drugs disrupt signalling in the brain stem respiratory network affecting respiratory rhythm. Mitsis et al., evaluated the influence of a steady-state infusion of a model opioid, remifentanil, on respiratory variability during spontaneous respiration using dynamic linear and nonlinear models to examine the effects of remifentanil on both directions of the ventilatory loop, i.e., on the influence of natural variations in end-tidal carbon dioxide $PET_{CO2}$ on ventilatory variability, (which was assessed by tidal volume ($V_T$) and breath-to-breath ventilation i.e., the ratio of tidal volume over total breath time $V_T/Ttot$), and vice versa. Breath-by-breath recordings of expired $CO_2$ and respiration were made during a target-controlled infusion of remifentanil for 15 min at estimated effect site (i.e., brain tissue) concentrations of 0, 0.7, 1.1, and 1.5 ng/ml, respectively.

They found that Remifentanil caused a profound increase in the duration of expiration. The obtained models revealed a decrease in the strength of the dynamic effect of $PET_{CO2}$ variability on $V_T$ (the "controller" part of the ventilatory loop) and a more pronounced increase in the effect of $V_T$ variability on $PET_{CO2}$ (the "plant" part of the loop). Non-linear models explained these dynamic interrelationships better than linear models. The described approach allows detailed investigation of drug effects in the resting state at the systems level using non-invasive and minimally perturbing experimental protocols, which can closely represent real-life clinical situations.

By contrast, the present invention involves using physiological signals, software algorithms and infusion devices (e.g. with a subcutaneous catheter, implanted device) and, in preferred embodiments, intranasal delivery, e.g. delivery to the mucosa of the nasal septum, particularly at Kiesselbach's plexus [also known as "Little's area"] and/or the nasal mucosa of the turbinates for the safe delivery of drugs which could potentially cause hypopnea, apnea and death if given in excess quantities. Since no single dose is appropriate for all individuals, and due to other medications and/or underlying clinical conditions, dosing without physiologic monitoring as disclosed herein, is unsafe. Furthermore, in the particular context of medical operations, the present invention provides a system, method and apparatus, herein referred to by the acronym TET (trauma environment treatment), in which operatives in trauma environment situations are able to receive appropriate pharmacologic intervention at a much earlier stage than has previously been possible. By coupling the PD, PK or PD+PK measurement sensors and signals of the present invention with the processor of this invention, and which then controls delivery of appropriate fluids and/or drugs to a subject, morbidity and mortality and potentially Post-traumatic Stress Disorder (PTSD) are substantially reduced.

In addition, by incorporating into TET a global positioning system, (GPS), a subject in need can be located, triaged, monitored, and optimally treated with drugs and/or fluids, either locally or remotely (e.g., rescue helicopters).

With respect to a further aspect of the present invention mentioned above, namely a system, method and apparatus combining PPG⁺+SMART (photoplethysmography plus other physiologic parameters+Self Monitoring and Reporting Therapeutics), there is disclosed integration of SMART technology described with PPG-based acquisition of medically relevant subject parameters. The SMART technology is covered by at least the following patent documents, each of which is herein incorporated by reference, including, as appropriate, pending and issued international and national equivalents thereof:

U.S. Pat. No. 7,820,108, Marker Detection Method and Apparatus to Monitor Drug Compliance; US US20050233459, Marker Detection Method and Apparatus to Monitor Drug Compliance; US20070224128, Drug Adherence Monitoring System; WO2007103474, Medication Adherence Monitoring System; W02008103924, Medication Adherence Monitoring System; U.S. Pat. No. 7,104,963, Method and Apparatus for Monitoring Intravenous (IV) Drug Concentration Using Exhaled Breath.

The PPG⁺ technology described herein for integration with the SMART system, is covered by at least the following patent documents, each of which is herein incorporated by reference, including, as appropriate, pending and issued international and national equivalents thereof: U.S. Pat. No. 6,909,912, Non-Invasive Perfusion Monitor and System, Specially Configured Oximeter Probes, Methods of Using Same, and Covers for Probes; WO/2004/000114, Perfusion Monitor and System, Including Specifically Configured Oximeter Probes and Covers for Oximeter Probes; U.S. Pat. No. 7,127,278, and U.S. Pat. No. 7,024,235, Novel Specially Configured Lip/Cheek Pulse Oximeter/Photoplethysmography Probes, Selectively With Sampler for Capnography and Covering Sleeves for Same; US 2007-0027375 A1, Optimized Gas Supply Using Photoplethysmography; WO/2005/065540, Novel Specially Configured Nasal Pulse Oximeter; WO/2006/086010, METHODS AND DEVICES FOR COUNTERING GRAVITY INDUCED LOSS OF CONSCIOUSNESS AND NOVEL PULSE OXIMETER PROBES; (WO/2006/116469) METHOD AND APPARATUS FOR DIAGNOSING RESPIRATORY DISORDERS AND DETERMINING THE DEGREE OF EXACERBATIONS; US 2008-0067132 A1, Method for Using Photoplethysmography to Optimize Fluid Removal During Renal Replacement Therapy by Hemodialysis or Hemofiltration; (WO/2008/020845) METHODS AND DEVICES FOR CENTRAL PHOTOPLETHYSMOGRAPHIC MONITORING METHODS With respect to infusion pumps, which are ubiquitous in hospitals and other healthcare settings, recently the FDA promulgated the "Infusion Pump Improvement Initiative" due to numerous reports of morbidity and mortality related to infusion pump (mis)use. See, for example, http://www.fda.gov/MedicalDevices/ProductsandMedicalProcedures/GeneralHospitalDevicesandSupplies/InfusionPumps/default.htm The predominant numbers of reported cases deal with PCA (Patient Controlled Analgesia) pumps, since such devices are designed to allow patients to self-administer, for example, opioids. While there are some control systems in place which limit the total dose of opioid and/or the frequency with which they are delivered, most dosing algorithms do not take into account all of the varying and relevant factors including, but not limited to, patient size and fitness (e.g., weight), pharmacokinetic interactions (Liberation, Adsorption, Distribution, Metabolism, and Elimination, LADME) that can alter opioid concentration in the blood, pharmacodynamic interactions (patient age, underlying medical conditions, including but not limited to undiagnosed obstructive or central sleep apnea, unusual sleep staging, cardiorespiratory disease, kidney or liver disease) that can markedly alter the biological sensitivity to opioids as well as active ingredients of medications in other medical classes.

Knowledge of these factors is required to properly calculate the appropriate (safe) dosing schedule of an opioid or such other medications for any particular patient. While this problem is particularly hazardous during opioid delivery, it can also occur in other medical settings where a patient is receiving intravenous (or medications administered by other routes such as epidural/intrathecal, and the like) medications and/or fluids, all of which have the potential of creating untoward and unexpected effects, especially when multiple medications are infused simultaneously or used in conjunction with many oral medications.

A 2005 review of PCA provides this summary of the potential dangers of this technology:

"Risk Factors for Respiratory Depression and Mishaps with IV-PCA

Several authors have summarized the risk factors for respiratory depression with IV-PCA. These risk factors can be categorized as "patient/disease related" and "technique/equipment" related. The patient/disease related risk factors apply regardless of route of opioid administration and include advanced age, head injury, sleep apnea syndrome, obesity, respiratory failure, concurrent use of sedative medications, especially benzodiazepines, hypovolemia, and renal failure. Unfortunately, avoidable instances of critical events continue to occur when IV-PCA alone is used. Some of the reasons include operator errors: programming errors (the most frequent mishap), accidental bolus administration during syringe change, inappropriate dose prescription or lockout interval, drug errors (wrong drug or wrong concentration), inappropriate drug selection (i.e., morphine or meperidine in a patient with renal failure), and disconnection or absence of Y-connector (allowing for accumulation of opioid in the IV tubing followed by intermittent bolus delivery). Common patient errors include activation of the PCA pump by others (i.e., family members), and failure to understand the device. Possible equipment problems include siphoning of drug (pump placed above patient without flow restriction valve or cracking of a glass syringe) and equipment failure resulting in spontaneous activation of drug delivery. A case report illustrates how IV-PCA can result in a lethal mishap. Vicente et al. describe a 19-yr-old woman who underwent uneventful cesarean section delivery, after which morphine IV-PCA was ordered. A drug cassette containing 1 mg/mL was unavailable, so the nurse substituted a cassette that contained 5 mg/mL. The patient was found dead 7.5 h later in her postpartum room. The available evidence was consistent with a programming error wherein morphine 1 mg/mL was entered instead of 5 mg/mL, thereby causing the pump to deliver a demand dose of 10 mg instead of 2 mg. Based on a search of the FDA Medical Device Reporting database and other sources and on a denominator of 22,000,000 PCA uses provided by the PCA device manufacturer, the authors estimated that mortality from user programming errors with this device is a small likelihood event (ranging from 1 in 33,000 to 1 in 338,800) but that it is relatively numerous in absolute terms (ranging from 65-667 deaths in the history of the use of the device). Clearly, mishaps with IV-PCA, mostly resulting from human error, remain a problem. To minimize the occurrence of these hazards, hospitals need to incorporate standard safety features into practice. Nursing staff on every ward must be trained in the safe use of PCA pumps and recognition and management of complications. Initial programming and setup of the pump and changes in programming require great care to prevent errors. It is common practice in most hospitals for a second nurse to witness and verify the initial programming and any changes in programming. Hospital pharmacies should formulate standard solutions of drug and send only those standard solutions to the wards. Patient and family education is important for safety, particularly instruction that only the patient should activate the PCA button", see REVIEW ARTICLE Grass J A, Patient-Controlled Analgesia. ANESTH ANALG 2005; 101:S44-S61.

Presently, patients are almost always placed on supplemental oxygen due to concerns that they may hypoventilate due to respiratory depression induced by opioids. They are almost always placed on a pulse oximeter to measure oxygen saturation, and recently, some hospitals have used capnography with or without pulse oximetry. Unfortunately, oxygen desaturation, which may occur with opioid use (respiratory depression), is severely blunted by the use of supplemental oxygen, and it has been shown that end-tidal carbon dioxide measurements are unreliable in spontaneously breathing patients when a nasal canula or similar device is used for monitoring.

Accordingly, there is an instant and pressing unmet need by the medical community for a monitoring system which automatically integrates all the factors previously discussed that determine proper opioid dosing, which can reliably detect cardiorespiratory changes in real-time and provide a means to discontinue continuous (e.g., intravenous or epidural) infusions until a healthcare worker (HCW) can be alerted to impending cardiorespiratory failure and alleviate the situation. This system would significantly reduce or even eliminate both "patient/disease related" and "technique/equipment" related morbidity and mortality in the setting of infused therapy with opioids and other types of medications such as local anesthetics (e.g., epidural).

Attempts have been made in the art to address the needs outlined herein above with respect to this aspect of the invention. Thus, for example, U.S. Pat. No. 6,165,151 to Weiner, provides an Apparatus and Methods for Control of Intravenous Sedation. The Weiner system essentially provides a controller unit which receives a pulse oximetry signal from a subject and, based on that signal, controls a flow restrictor in contact with an IV line from a gravity fed medication source to a subject. As will be appreciated from a review of the complete disclosure which follows, the present system is designed to make a PCA pump safer by preventing a patient from overdosing with an opioid through their own volition, error or the like. Additionally, it provides a "safety net" should a healthcare worker accidently input the wrong infusion rate or give the wrong concentration of medication. The Weiner device is designed to go on a free flowing IV system which is inherently dangerous, and in any event, is a closed-loop system for medication delivery, which is distinguishable from at least one aspect of the present invention, which is a stand-alone safety device which can be used agnostically with any infusion pump or medication delivery system for delivery of medication to a subject from an external source. Furthermore, while the Weiner system uses a pulse oximeter for a feedback loop, this is also used in several PCA pumps such as the Alaris® system from CareFusion. The present system, as will be seen below, does not utilize pulse oximetry as the major means of monitoring, for example, opioid effects on a patient, since, as expanded upon below, pulse oximetry is notoriously a late signal to use for feedback (e.g. patients receiving oxygen can exhibit dangerously high $CO_2$ levels resulting in respiratory depression or complete apnea without any change in oxygen saturation). Instead, in a preferred embodiment, the present invention, as disclosed below, utilizes a Single Point of Contact (SPOC) probe, preferably comprising a combination of Photoplethysmography (PPG) plus nasal airway pressure/flow and an accelerometer to detect early deleterious effects of, e.g. opioids (changes in I:E ratio [inspiratory to expiratory time], length of expiratory time, respiratory rate, etc.) none of which can be detected with a pulse oximeter.

In a variant to the Weiner U.S. Pat. No. 6,165,151 patent disclosure, Weiner also, in a subsequent patent publication, US2005/0027237, disclosed substantially the same system as disclosed in the '151 patent, but in use with a blood pressure monitoring system to assist in treating patients suffering potentially catastrophic blood and/or fluid loss. The same or similar considerations as noted above apply to this publication as well. Blood pressure monitoring is of little value in determining when to discontinue an opioid infusion, as changes in blood pressure are a late sign and respiratory not cardiovascular effects predominate. In the setting of catastrophic blood loss, an ideal closed-loop system would maximize fluid delivery, but depending on the medication being infused this could, in itself, lead to catastrophic outcomes if, for instance, a medication to lower blood pressure was being infused. Finally, in most circumstances blood pressure is a late finding during blood loss, while the instant invention uses sensing technology that detects impending hypovolemic shock rather than shock after it has occurred.

In WO2007/033025, and in related US2009/0177146 to Nesbitt et al., a system substantially similar to the Weiner system was disclosed as a closed-loop system for controlling a pump-delivered medication to a subject whose vital signs from physiological monitors attached to a patient. That system includes an occlusion sensor, and in relation to the Weiner system, confirms our observations above, that the device of Weiner "fails to monitor many patient vital signs such as blood pressure, temperature, respiration rate, and capnography readings . . . . A lone pulse oximetry device may not be able to accurately assess the true condition of the patient, leaving the patient vulnerable to improper controller adjustments of fluid flow rate." To cure these acknowledged defects in the Weiner system, Nesbitt et al., propose a system in which, in addition to or in place of a pulse oximeter, there is included a breath analyzer, for analyzing, for example, propofol in the breath of a subject, according to US20050022811 (Kiesele et al), for analyzing $CO_2$, $O_2$ volume flow, temperature sensor, an ECG electrode and a photo-plethysmography (PPG) device to generate Pulse Transit Time (PTT), and the like. This system too, while on first inspection appears similar to an aspect of the system we describe herein, is likewise distinguishable as it requires careful integration of the physiological sensors connected to the patient with the fluid delivery system—in a closed-loop or advisor controlled medication delivery system. Accordingly, the Nesbitt et al., solution is not an agnostic solution which can be utilized as a "bolt-on" safety device for use with any existing fluid infusion system.

Finally, it is worth noting that Hickle et al., US2003/0040700, likewise discloses a highly complex, closed-loop infusion system for a patient which is likewise dependent on careful integration of patient physiologic monitors with the infusion system, and thus suffers from the same issues noted above in connection with the Nesbitt et al., system. By contrast, the present system is simple and focuses on one problem—shutting off flow from the medication source if there is a trend towards cardiorespiratory depression, without having to integrate a number of vital sign parameters into an infusion device, which would be highly complex and require a great deal of skill to be exercised by the user even if algorithms are written to control the pump.

Accordingly, in the present patent disclosure, we provide a system for use of photoplethysmography (PPG) and/or other cardiorespiratory signals (nasal airway pressure [NAP] or flow [NAF]) and the addition of an accelerometer, preferably at a single point of contact (SPOC), preferably the nasal alae, to monitor cardiorespiratory function during infusion therapy. Furthermore, we provide an improvement to such a system wherein the improvement includes, in addition to the monitoring system, a small device (pneumatic, mechanical or otherwise actuated) that is connected to intravenous (or epidural/intrathecal) tubing running between an infusion pump and a patient to "pinch" the tubing, thus disrupting the flow of the opioid (or other medication or fluids) until a HCW intervenes, without requiring any other (e.g. electronic) integration with the fluid/medication delivery system. With this approach, we propose an "infusion pump agnostic" solution to this pressing medical need which does not require imposing design and regulatory burdens on infusion pump manufacturers. We further believe that the FDA will embrace a straightforward solution that can be implemented on all infusion pumps in a timely manner.

In addition to the various aspects of this invention discussed above, and how these aspects differ from reports in the patent or technical literature, this patent disclosure provides a medication agnostic safety system which, in various embodiments, can control the level of medication infusion into a subject, based on real-time or as near to real-time as possible measurement of subject physiological condition, and which, in the same or different embodiments, can initiate supplemental safety measures, including, for example, reduction in or cessation of medication delivery, and, as appropriate, initiation of positive airway pressure or similar forms of ventilation, when such is called for. Accordingly, this invention provides a solution to the long-felt need for a safe system, either in an advisory capacity for trained staff or in a control capacity, to improve the safety of medication administration.

SUMMARY OF THE INVENTION

This invention provides a system, apparatus and method for enhancing the safety of subjects in a wide variety of scenarios where medication and/or fluids is or need to be delivered to a subject. A common feature in various aspects and embodiments of this invention is the utilization of signals obtained or obtainable from photoplethysmography (PPG) devices affixed to a subject, preferably emplaced on a subject at at least one Central Source/Sensing Site (CSS), defined as a site above the neck of the subject, and preferably at the nasal alae. In another embodiment, the nasal alar PPG sensor is combined with at least one, a combination of or all of the following additional apparatuses: (a) a second site PPG sensor, preferably at a peripheral site, such as a finger or a toe, or both; (b) an infusion pump and at least one reservoir of at least one pharmaceutically active agent, (a medication or a drug); (c) an occlusion apparatus which, on receipt of a signal from a PPG sensor or a controller to which the PPG sensor is operatively coupled, partially or completely occludes a conduit from a medication reservoir to a subject; (d) a controller which receives a signal or signals from one or more PPG or other sensors operatively coupled to a subject and which outputs signals based on the signals received by the controller and algorithms programmed into the controller for producing output signals based on signals received from the sensors; (e) sensors other than PPG sensors, selected from the group consisting of ECG, pulse oximeters, capnometers, and the like, well known in the art; (f) ventilation means for applying positive ventilation pressure to said subject upon receipt by the ventilation means of control signals to initiate, increase or decrease ventilation; (g) SMART medication system for providing confirmation that a given medication has been taken or been administered, that it has been taken or administered at the correct dosage and at the correct time.

Accordingly, it is an object of this invention to provide a system, method, and apparatus for safe administration of fluid and/or at least one pharmaceutically active agent to a subject along with means for increasing, decreasing or terminating the administration of the pharmaceutically active agent.

It is a further object of this invention to provide a method, apparatus and system which utilizes PPG monitoring of a subject at one or more sites to control or provide trained staff with improved information on the need for control of the delivery of pharmaceutically active agents.

It is a further object of this invention to utilize pharmacodynamics (PD), pharmacokinetic (PK) or both PD and PK data acquired from an individual to control or advise trained staff in the control of administration of pharmaceutically active agents and ventilation.

Other objects, advantages and embodiments according to this invention will be apparent to the skilled artisan on review of the entire disclosure provided herein, including the appended claims.

BRIEF DESCRIPTION OF THE DRAWINGS

FIG. 18: The left panel shows the correlation between respiratory rate as determined by nasal pressure (NAP) and PPG ($r^2$=0.83) in one minute regions across 35 patients. The bland-altman is shown in the right panel.

DETAILED DISCLOSURE OF THE INVENTION AND ITS PREFERRED EMBODIMENTS

Introduction and Definitions

Figure 1:
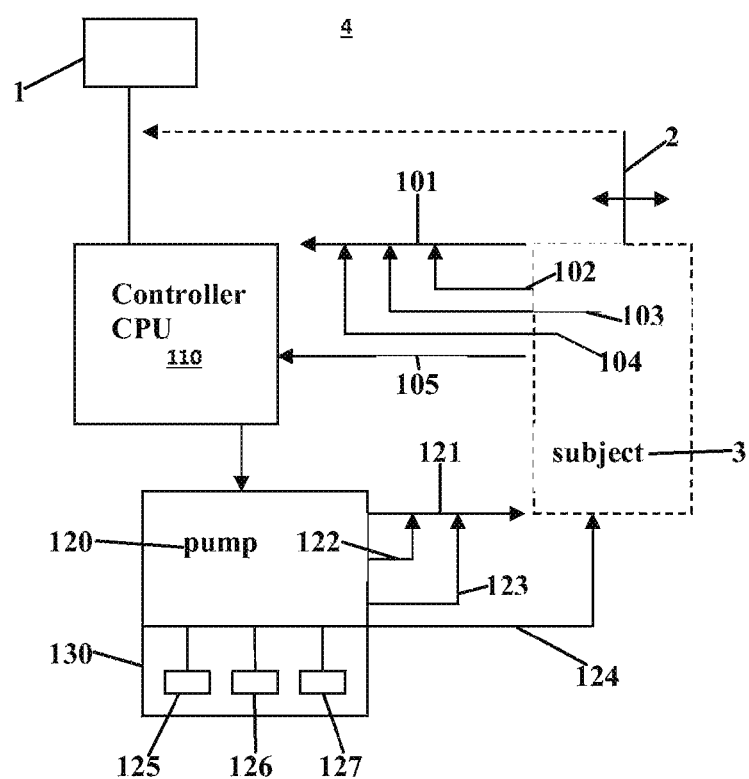
FIG. 1 provides a schematic representation of an apparatus of this invention, working as an integrated system to implement the method of this invention, whereby 1) PD parameters (biological responses, including but not limited to respiratory, hemodynamic, and movement responses, as defined above, to different blood concentrations of active pharmaceutical ingredients [APIs] such as opiates, propofol, etc) using PPG/ECG signals, are measured, 2) PK parameters (drug levels of APIs in blood such as opiates, propofol, etc. are measured using various biological matrices including but not limited to breath and blood), or 3) PD+PK parameters and other relevant signals are obtained from a subject and relayed to a controller which processes the incoming information from the subject to control at least one infusion pump which provides fluids and/or drugs to the subject at increased or decreased rates depending on the signals provided to it by the controller.

This invention provides a system, method and apparatus for acquiring patient physiological data, acquired at a central source (or sensing) site of a patient, and utilizing information derivable from that signal in the control of delivery of medication or fluids to a subject in need of such treatment.

Various modes for utilizing this invention and specific embodiments of this invention exemplify the comprehensive medication delivery and enhanced safety solution of this invention.

For example, this invention provides a photoplesmythographic solution, referred to for convenience herein as PPGcare™, whereby, during delivery of anesthetic agent to a subject, a first signal is acquired at a central source site of the subject and is monitored for evidence derivable from the first signal which is known to be indicative of hypoventilation. On detection of evidence of hypoventilation, a second signal is generated which is sent to a controller to (i) alert staff of the identified hypoventilation; (ii) to automatically initiate positive pressure ventilation of the subject; and, if the positive pressure ventilation does not produce evidence of resolution of hypoventilation in the subject, to (iii) decrease or stop delivery of anesthetic agent. In a sophisticated embodiment implementing this exemplary application, a central controller extracts the information required from the central source site photoplethysmography signal to acquire the venous impedance signal from which evidence of increased breathing effort or decreased breathing rate or regularity is extracted. The controller, then, based on the evidence, and in a preferred embodiment, after confirming that no contradictory signal is being acquired from any other sensor, limits or turns off delivery of the anesthetic agent unless/until the evidence of hypoventilation is resolved or trained personnel intervene.

This example is mentioned in this introduction to point out that, while the particular application outlined is an important medical application, it is not co-extensive with the PPGcare™ invention. This can easily now be apprehended but considering that, in the above example, if instead of acquiring a signal from which evidence of hypoventilation can be extracted, instead a signal is acquired from which evidence of hypovolemia is derived, the application of the invention to a medical scenario where renal replacement therapy by hemodialysis or hemofiltration becomes apparent.

By appropriately emplacing a photoplethysmography sensor at a central source or sensing site (CSS) and obtaining and appropriately processing the signal from the CSS sensor, a control signal can be generated for provision to a medication and/or fluid controller to, at least in part based on the signal from the CSS, initiate, terminate, increase and/or decrease provision of pharmacologically active agents and/or fluid. In fact, as will become apparent from a review of the entire disclosure, there is at least one proposed product awaiting FDA approval for which this application filing provides a key safety feature and which, upon integration into such proposed product, could meet with approval not only of the FDA but also by the American Society of Anesthesiologicts (ASA).

Definitionally, it will be understood from the present disclosure that the term SPOC refers to Single Point Of Contact sensor(s) that can measure: oxygen saturation, PPG, nasal airway pressure, nasal airway flow, humidity, temperature, ECG, derived parameters (PTT), etc, and deliver drugs, all at a single point of contact with the physiognomy of a subject in need of such treatment.

The nasal alae, septum, cheek, lip, preauricular and post-auricular sites are all central sensing or source sites (CSS) for signals obtained by an SPOC or CSS sensor.

The fingers, toes, etc. are peripheral sensing site (PSS).

The present patent disclosure provides a comprehensive safety solution to the armamentarium of medical practitioners and other individuals in a number of contexts for which there have heretofore been inadequate solutions. The apparatus, system and method of the present invention, referred to for convenience herein as PPGcare™, is relevant to at least the following contexts, each of which are addressed in detail herein below. It will be appreciated that these scenarios are not limiting and are provided for purposes of fully describing and enabling this invention. However, other scenarios and applications will be apparent to those skilled in the art upon review of the entire disclosure and appended claims:

Scenario A: Isolated Individuals in Need of Medical Attention

In situations where an individual is in an isolated environment, e.g. hiking, mountain climbing, aircraft piloting, to mention a few, where medical care is not readily at hand and where a life-threatening condition arises—PPGcare™ provides an interim, substantially automated solution for evaluation of a plethora of pharmacodynamic (PD), pharmacokinetic (PK) or both PD and PK parameters of the individual and is able, based on processing of signals acquired, at least in part by a photoplethysmography apparatus, and, preferably, additional monitors and sensors, to initiate emergency delivery of appropriate medications, fluids and the like, until trained medical personnel can reach the individual and intervene if necessary.

Scenario B. PPG+SMART—PK/PD and Compliance Monitoring

In situations where it is necessary to not only acquire PD, PK or both PD and PK parameters of a subject, but to also confirm delivery of the correct medication at the correct dosage within appropriate time frames, the PPGcare™ system includes the use of medications which include Self Monitoring and Reporting Technology (SMART), which permits, at a minimum, not only acquisition of PD, PK, or both PD and PK parameters of the individual, but also an independent means for confirming that fluctuations in these parameters correlate with the administration of the SMART medications.

Scenario C: Infusion-Pump Agnostic PPG-Based Safety Over-Ride of Medication Infusion In situations where a medication is being delivered to a subject via an infusion pump, whether in an open-loop or closed-loop context, and an adverse individual parameter is detected from monitoring the total PK, PD, or both PK and PD parameters, (including specific parameters discussed in detail herein below), of the individual undergoing infusion, the PPGcare™ system in one embodiment includes an infusion pump agnostic component to reduce or terminate the infusion and to alert appropriate healthcare professionals that the individual is in need of attention.

Scenario D: Enhanced Safety in Delivery of Medications which can or do Depress Respiration or Increase Respiratory Effort In situations where close monitoring of anesthetic agents, opioids or like compounds and combinations of compounds, is required, (which is always, of course, the case, but in certain contexts, particularly, for example, in the context of the need for maintaining minimal sedation e.g. for colonoscopies or esophagoduodenoscopy (EGD) procedures, it has been proposed that in the delivery of "conscious sedation" by non-anesthesiologists or in the delivery of opioids and other drugs that cause respiratory depression, often in combination e.g. opioids and benzodiazepines), especially during patient controlled analgesia (PCA) administration), whether trained anesthesiologists are present or not, the PPGcare™ system of this invention provides a critical safety system and advisory outputs, such that in the event of detecting respiratory depression, elevation in respiratory effort, elevation in blood $CO_2$, decrease in blood $O_2$, saturation, or any other indicator of hypoventilation, PPGcare™ optionally includes for such circumstances appropriate sensors and means for delivery of positive ventilation to maintain airway patency, means for reducing or terminating delivery of opioids or other medications, and alarms to alert appropriate professionals that the subject is in need of attention.

Those skilled in the art will appreciate that the particular elements of the PPGcare™ system relevant to one scenario or context may be combined with other elements relevant to another context, and that the above listing of particular contexts in which PPGcare™ may be applied to enhance patient safety is not intended to be exhaustive. Other applications and contexts will occur to those skilled in the art from a review of the entire disclosure provided herein and the appended claims.

The detailed disclosure which follows describes in detail and enables each of the various elements of PPGcare™ and provides examples of particular contexts in which particular combinations of the elements and embodiments of the system are applicable.

Before, however, proceeding with the detailed disclosure of the various embodiments and iterations of the present system, method and apparatus, it is considered relevant to set the stage by summarizing some salient features of a central unifying technology which has, heretofore, received inadequate attention in medicine generally, and which in at least one aspect of the present invention, provides a central unifying feature of various embodiments and iterations of this invention, namely, plethysmography, and, specifically photoelectric plethysmography or photoplethysmography, referred to herein as PPG.

PPG is a deceptively simple method whereby a source of radiation, usually light at a particular wavelength (e.g. a light emitting diode, LED, typically at 940 nm, or 660 nm), is coupled with a light detector (e.g. a photo diode, the photodetector) such that light is either detected as it passes through a tissue (transmission PPG) or is reflected from the tissue (reflective PPG). The amount of light that is absorbed (transmission PPG) or scattered/absorbed (reflective PPG) is detected by the photodetector. The familiar Beer Lambert law ($A_{total}=E_1C_1L_1+E_2C_2L_2+ \ldots E_nC_nL_n$, wherein $A_{total}$=absorption at a given wavelength, $E_n$=extinction coefficient (absorbency), $C_n$=concentration, and $L_n$=light path), is employed to convert the light detected by the photodetector into an output waveform. This is where the apparent simplicity begins to devolve into complexity for a number of reasons.

The first of these reasons is that early in the development of PPG technology, it was appreciated that by using light at two different wavelengths (usually 650-670 nm and 880-940 nm, and thereby harnessing the different extinction coefficients of hemoglobin with and without bound oxygen) the pulsatile waveform output by the photodetector could be used to measure arterial oxygen saturation, and, as a result, pulse-oximetry became a staple patient monitoring device. This mode of using PPG eclipsed all other uses to the point where in commercial devices using the essentials of the PPG technology described above, it has become almost impossible to obtain raw signals which are not pre-processed, auto-gained, averaged etc. (see, for a review of the history of development of pulse oximeters and the built-in processing that has occurred which now eclipses other uses, "Photoplethysmography: Beyond the Calculation of Arterial Oxygen Saturation and Heart Rate", Kirk H. Shelley, Anesthesia & Analgesia, 2007, 105, No. 6, S31-S36). This history notwithstanding, however, certain of the inventors in the present patent disclosure have advanced the field in a number of areas and respects, mining the PPG signal to produce solutions in a number of previously unmet technical and clinical areas. All of the following patent documents are referred to in this regard, and certain of the details in the patent documents listed are relevant to implementation of specific aspects and embodiments of the present invention:

U.S. Pat. No. 6,909,912, provided a "Non-invasive perfusion monitor and system, specifically configured oximeter probes, methods of using same, and covers for probes". This patented technology advanced the field by showing that analysis of signals acquired from at least two pulse oximeter probes, one positioned at a Central Source Site (CSS, which is any highly perfused site in the head), and comparing the signals with those obtained from a Peripheral Site (PS, e.g. a finger, toe, etc), changes in perfusion at the peripheral site as compared to the central site and changes in vascular resistance (based on difference in pulse transit times measured at the two sites) could assist in evaluating the degree of perfusion at the peripheral site and changes in perfusion between the two sites. In a particular embodiment, where the oximeter probe is adhered to the nasal alar CSS, there is also provided an embodiment in which provides oxygen to the subject through channels provided in the structure of the probe.

U.S. Pat. Nos. 7,127,278 and 7,024,235, provide specially configured lip/cheek pulse oximeter/photoplethysmography probes, selectively with sampler for capnography, and covering sleeves for same.

U.S. Pat. No. 7,785,262 provides a method, apparatus and system for diagnosing respiratory disorders and determining the degree of exacerbations, and, in particular, a signal processing method for separating out pulsatile, arterial, heart-beat derived (AC) components and vascular impedance (DC), breath-based components in the PPG signal derived from a Central Source Site (CSS) in the head of a subject. This technology is useful for detecting increases in subject breathing effort, decreases in breathing rate, and occurrences of breathing disturbances, and respiratory effort, such as in sleep apnea.

U.S. Pat. No. 7,887,502 provides a method for using PPG to optimize fluid removal during renal replacement therapy by hemodialysis or hemofiltration. By obtaining and appropriately processing PPG signals secure at a CSS or CSS and PSS, it was shown that the system could be used to monitor and prevent hypovolemic states in patients undergoing either fluid removal or hemofiltration and to maintain appropriate fluid balance in such subjects.

In light of these advances, it can be seen that significant advances have been made in utilizing the PPG signal to derive a range of significant parameters with respect to the status of a subject's perfusion state, state of fluid balance, and respiration status.

In the present disclosure, not only are these advances superseded from an diagnostics perspective, but the power of the PPG signal, particularly when derived from a CSS such as the nasal alae, alone or in combination with monitoring at a second, peripheral site, provides the opportunity for significantly enhancing the safety of various procedures in which fluids or medications are being administered to subjects. The power of the CSS PPG signal is harnessed herein by being utilized either in an advisory capacity, and in certain specific embodiments, in a control capacity, in a wide array of scenarios, as outlined above and as described and enabled in detail herein below.

Scenario A: Isolated Individuals in Need of Medical Attention

In situations where an individual is in an isolated environment, e.g. hiking, mountain climbing, aircraft piloting, to mention a few, where medical care is not readily at hand and where a life-threatening condition arises—PPGcare™ provides an interim, substantially automated solution for evaluation of a plethora of pharmacodynamic (PD), pharmacokinetic (PK) or both PD and PK parameters of the individual and is able, based on processing of signals acquired, at least in part by a photoplethysmography apparatus, and, preferably, additional monitors and sensors, to initiate emergency delivery of appropriate medications, fluids and the like, until trained medical personnel can reach the individual and intervene if necessary.

A.I. Summary of this Aspect of the Invention:

A pharmacodynamic (PD), pharmacokinetic (PK), or both PD and PK guided infusion device, system and method optimizes the safety and efficacy of various forms of treatment or therapy (e.g., drug and/or fluid) in a variety of health-care and other settings.

The system of this aspect of the invention involves linking an apparatus or series of apparatuses which can reliably and rapidly (i.e. in as close to real time as possible) measure relevant PD, PK, or both PD and PK parameters of a subject, process the relevant PD, PK or PD+PK measurements and, on that basis, control one or more infusion pumps for closed-loop or open-loop delivery of opioids and other drugs or fluids to a subject. Such linkage is typically via a control system which implements appropriate algorithms as described herein for interpreting the PD, PK and any other relevant data, to control the rate of infusion of a particular therapeutic agent to appropriate delivery sites in the subject, including, but not limited to, intravenously, intraperitoneally, intranasally (whether in the form of a fluid, a mist, an aerosol, and/or a non-aerosol fluid delivery system and whether including or not including pharmacologically active compounds), as appropriate in a given context. For intranasal delivery, the therapeutic agents could be stored in various locations of the system, including near (or in) the nose or at sites more distant from the nose (e.g., adjacent to ear or forehead).

By so doing, it is possible, for example, to safely deliver opioids and other drugs to hospice or other patients with chronic pain, or in environments where the effective management of acute pain with narcotics is required (e.g., post-operative pain relief in hospitals). By monitoring their respiration, for example by implementing a device or system such as that described in the '506 publication, the danger of over-medication is reduced or eliminated.

The system, method and device of this aspect of the invention may be optimized for use in civilian inpatient, outpatient or in medical contexts, as described in detail below.

Accordingly, it is an object of this aspect of the invention to provide a medication and/or fluid delivery and control system, method and apparatus which includes at least one apparatus for measuring at least one relevant pharmacodynamic (PD) parameter or at least one pharmacokinetic (PK) parameter or both at least one PD and at least one PK parameter in a subject; an infusion device with a rate of infusion which is increased, decreased, or maintained at a given level of infusion based on the at least one PD, PK, or at least one PD and at least one PK parameter; and a controller for receiving the at least one PD, at least one PK or at least one PD and at least one PK parameters and, based on the relevant parameters and hardware and software (including algorithms appropriate to the particular subject, context and treatment modality), increasing, decreasing or maintaining the rate of infusion of the infusion device(s).

It is a further object of this aspect of the invention that in such a system, method and apparatus, the medication delivery and control system may be a closed-loop or an open-loop system.

It is a further object of this aspect of the invention to provide appropriate algorithms, guidance and considerations relevant to a wide array of subjects and treatment regimens so that the advantages of the present system may be widely implemented and used for the added safety of subjects.

Other objects and advantages of this aspect of the invention will become apparent from a review of the entire disclosure herein and from the appended claims and their equivalents.

A.II. The Delivery System of this Aspect of the Invention:

The present invention provides a means to control a fluid delivery device, such as an infusion pump, solenoids for release of pressurized gasses, aerosols and the like, or any other appropriate or equivalent fluid delivery device known in the art, for infusion of opioids, other drugs, fluids or any other composition which has a respiratory, hemodynamic or other pharmacologic effect in a subject. By coupling the infusion pump to a control system which receives and analyzes signals from one or more systems which measure appropriate pharmacodynamic (PD), pharmacokinetic (PK), or both PD and PK parameters of a subject, the infusion to the subject is then appropriately monitored and controlled by the control system.

Pharmacodynamic parameters involve those relating to how a drug acts on a living organism, including the pharmacologic response and the duration and magnitude of response observed relative to the concentration of the drug at an active site in the organism. Pharmacokinetic parameters involves those relating to how a drug is interacting within a body, including but not limited to, mechanisms of drug liberation, absorption, distribution, metabolism, and excretion, onset of action, duration of effect, biotransformation, and effects and routes of excretion of the metabolites of a drug.

As noted above, there are many known systems for measuring various PD and/or PK parameters in subjects. This invention provides a novel and unique system, method and apparatus for coupling known or novel (including those disclosed herein and which hereafter come to be known) PD and/or PK measurement systems to infusion apparatuses so that measurement of appropriate PD and/or PK parameters is conducted concurrent with or substantially concurrent with (i.e. there may be a slight delay of a few seconds or milliseconds between receipt of signals from the subject, processing of the signals and changes in the rate of infusion to the subject; delays in the signals are related to physiology and filtering—if, for example, the respiratory rate is 10-15 bpm, then detecting a change in the respiratory rate will take at least 10 seconds to ensure a single breath artifact does not indicate a false change in breath rate; therefore, it could take up to several seconds to detect a change in a slow physiologic signal—accordingly, the term "substantially concurrent with" is intended to mean a time of between about 0.1 millisecond and about 20 seconds, or between 1 millisecond and 15 seconds, or between 10 milliseconds and 10 seconds, or between 0.1 second and 1 second, as appropriate to the needs of a given situation) supply of medications, fluids or both. Based on instantaneous or substantially instantaneous (i.e. within a few seconds or milliseconds from the acquisition of signals from the subject) and/or trending of relevant PD and/or PK parameters, and based on appropriate algorithms (appropriate to a give subject, to a given subject type, to a given condition, to a given condition type), a control system is able to receive the PD and/or PK signals throughout an infusion or similar treatment process and to either increase, decrease or maintain the rate of infusion of one or more drugs and/or fluids to the subject. This substantially enhances the safety of such treatments for subjects in a wide variety of contexts (e.g. for hospital inpatients, for hospice patients, for subjects residing at home or alternative health care facilities, in old age homes or the like, and, e.g. in acute care, in chronic care, in the field for medical personnel etc).

This invention provides an optimized device, system and method for medical therapy whereby pharmacodynamic (PD, e.g. respiratory and cardiovascular responses) and/or pharmacokinetic (PK, e.g. blood level, breath level—see, for example, US20040081587—drug marker breath detection, US20080059226—drug marker breath detection, US20080045825—glucose breath detection, and U.S. Pat. Nos. 7,104,963 and 6,981,947—propofol breath detection, all of which are herein incorporated by reference) measurements are utilized to guide infusion devices using closed and/or open control loop systems. By monitoring cardiorespiratory-based PD parameters, with or without measurement of PK parameters, the device, system and method of this invention non-invasively integrates a variety of factors, including but not limited to exogenous drug administration, attempts to resuscitate, and the like at the level of the cardiorespiratory system, in a manner that allows optimal regulation and titration of infusion rates of various drugs and fluid volumes. This technology substantially enhances such treatments by not only optimizing their efficiency, but also substantially enhancing the safety of such procedures, particularly in clinical settings where a manpower force multiplier is badly needed (e.g., trauma zones, hospices, hospitals, etc).

It should be noted that by combining measurements of selected PD parameters, including but not limited to respiratory rate and consistency (e.g. low Respiratory Disturbance Indices, RDI's=the number of 10 second pauses per hour, with mild being considered to be 5-15 such events per hour, moderate being 15-30 and severe being anything above 30 per hour), cardiac output (e.g. by ECG measurement or plethysmography signal processing to obtain AC/DC components, as described in detail in, for example US2010192952, herein incorporated by reference for this purpose), nasal pressure fluctuations (which permit accurate measures of breathing rate to be determined even when breathing via the mouth—nasal pressure waveform shapes also indicate characteristics of the breathing, such as the gradual increase in occlusion or resistance during exhalation or inhalation, increase in respiratory effort, and the like, all of which information is accessible and useable in various embodiments of this invention, as appropriate to a given situation), it is possible to obtain total "snapshots" of the physical status of the subject at any given time, summing up the influences of all external effects (e.g. gravity, low oxygen, high smoke or pollution, fluid or blood loss or other types of injury), and internal parameters (hypovolemia, anemia, any drugs operating in the metabolic pathways of the subject, etc), and provide appropriate pharmacologic intervention.

It should be noted that while the term "snapshot" implies an instantaneous reading, "trends" and detection of changes in trends are also amenable to analysis and manipulation according to this invention. Trend analysis may be particularly important for plethysmography signal analysis, since plethysmography data requires calibration and therefore following trends provides clear benefits in this regard.

Coupling analysis if PD parameters, whether at particular instances or over periods of time to monitor trends, with PK parameter acquisition (e.g. by measurements of blood concentrations of pharmaceutically active compounds or their metabolites, or by measuring the concentrations of markers on the breath of the subject, whether such markers are the compounds themselves, surrogates for these compounds or metabolites thereof), permits a total picture for the subject to be accessed at any given time, and integrated into the pharmacologic response. Such responses, per one embodiment of this system, method and apparatus of this invention, is entirely autonomous and self-contained—all signal acquisition, processing and infusion responses are integrated into a system which the subject incorporates into their attire (whether as part of a helmet, belt, probes affixed to appropriate physiological aspects—nasal alae, ears, cheek, and whether PPG probes, nasal pressure probes, ECG probes or the like).

Alternatively, or in addition, via appropriate telemetry, wired or wireless technology (whether using GPS signals, internet, 3G, 4G, infrared, ultrasound, or any other electromagnetic radiation means, now known or hereinafter developed), the system may communicate with and optionally be under the control of external analysis and control. This latter option provides for force-multipliers to come into operation, allowing a central person or teams of persons to analyze data relevant to one or multiple individuals and to over-ride autonomous operation and provide even more appropriate interventions then are possible under completely autonomous operation of the system, method or apparatus of this invention.

A.III. Drug Delivery Modes:

Although the preferred embodiment of this aspect of the invention includes one or more infusion devices, a number of other drug delivery modes, used alone or in combination, can be utilized with this invention. They include but are not limited to:

Continuous drug and fluid administration: Introduction of a medication (or fluid) into the body in a continuous (dosing rate may vary however) manner. Although in this scenario most applications would include the administration of intravenous drugs or fluids, it could also entail, for example, transdermal skin patches that continuously deliver drugs through the skin, subcutaneous, rectal, intraosseous and intranasal administration.

Intermittent drug administration: Introduction of a medication (or fluid) into the body in an intermittent manner. Examples here include but are not limited to intermittent dosing with oral, eye, intravenous, subcutaneous, intranasal, intraosseous or inhalational drugs.

The delivery of fluids and/or gasses may be via appropriate pumps, or, in a preferred embodiment, pressurized vessels containing appropriate fluids, drugs, nutrients (e.g. glucose) and the like, are released in pre-metered doses on actuation of a release mechanism (a valve, servo, septum or the like). Each time a particular pressurized vessel is instructed by the system to release a pre-metered dose, an appropriate dose is delivered to the subject. By sending multiple instructions, multiple doses may be applied to the subject to simulate almost continuous infusion until a reduce delivery signal or a cease delivery signal is applied to prevent further infusion of the particular agent or agents to the subject.

A.IV: Site of Drug Administration:

Using different types of drug (or fluid) delivery modes, a wide variety of drug administration sites exist, including but not limited to the following: intravascular (intravenous or intraarterial), subcutaneous, oral, intranasal, intraosseous, transdermal (e.g., iontophoretic or non-iontophoretic-based), intramuscular, intravaginal, sublingual, rectal, intraosseous, transocular (eye) or intraocular, intraotic, pulmonary or intrapulmonary (transtracheal, or via metered dose inhalers [MDIs]), epidural, intrathecal, neuraxial (central nerves, peripheral nerves), and intracerebral. In a particularly preferred embodiment, because of the high rate of bioavailability, absorption and low time for effect, delivery to the nasal epithelium is utilized. Delivery may be by application of a fluid, an aerosol, a non-aerosol, or the like, with or without permeability enhancing compounds.

A.V. Examples of Medical Therapies:

Any medical therapy (e.g., drug and/or fluids) that modulates cardiorespiratory function (stimulates and/or depresses) in vivo, particularly those centers in the brain (e.g., brainstem) that regulate the respiratory and cardiovascular systems, can be controlled with the current invention in a manner that will substantially improve outcomes in terms of improved drug safety and efficacy, and reduce morbidity and mortality. In addition to the PD control of drug delivery described above, PK based strategies, used alone, or in combination with PD can be devised. Examples of medical therapies which can be controlled in this manner include:

Conscious sedation or general anesthesia
Pain relief
Attention Deficit Hyperactivity Disorder (ADHD)
Treatment of cardiovascular disorders, including trauma
Migraine headaches A.VI. Drug Treatments:

Narcotics (e.g., sufentanil, morphine, fentanyl, alfentanil, oxycodone, methadone, oxymorphone, Remifentanil),
Anesthetics and anesthetic adjuncts (e.g., inhalational anesthetics [sevoflurane, xenon, isoflurane, desflurane], intravenous anesthetic agents [propofol, ketamine, dexmedetomidine, benzodiazepines], and local anesthetics [lidocaine, bupivacaine, ropivacaine]).
ADHD treatment (e.g., short and long acting CNS stimulants including but not limited to methylphenidate, amphetamine, methamphetamine).
Migraine headaches (e.g., dehydroepiandrosterone [DHEA], lidocaine, serotonin receptor modulators, such as triptans)
Weight loss medications (e.g., phenteramine)
Cardiovascular drugs (e.g., dopamine, dobutamine, ephedrine, vasopressin, epinephrine, norepinephrine, beta and alpha receptor agonists and antagonists, phosphordiesterase inhibitors, etc.)

A.VII. Non-Drug Treatments:

Fluids, including volume expanders, nutrients, e.g. glucose, given via the intravascular route, including intravenously, intraarterially and intraosseously
Efficacy of cardiovascular assist devices (e.g., automated chest compressors, manual cardiopulmonary resuscitation, intraortic balloon pumps).

A.VIII. PD-Based Sensor Locations:

Number—1) single (nasal ala; ear, finger; etc), and 2) multiple (e.g., nasal alae+finger; nasal ala+finger+toe); Location: central (e.g., ala, lip, cheek, tongue) versus peripheral (e.g., toe, finger, ear) photoplethysmograph (PPG) sensors.

A.IX. Types of Sensors that Guide Therapy:

PD (cardiorespiratory information used to determine drug effects): photoplethysmograph (PPG), capnograph (IR, etc), nasal pressure, nasal flow, electrocardiogram (ECG), chest wall and abdominal impedance, any parameter measurable using polysomnography or combinations thereof; PK (drug blood levels) information: nanosensors for breath; others for other biological media, etc.; integrated sensors that integrate PD and PK information.

A.X. Basis of Control Loop:

Pharmacodynamic-based, Pharmacokinetic-based, or a combination of the two.

1. Output of PD-based sensors: Numerical parameters indicating cardiorespiratory function, including but not limited to heart rate, respiratory rate, $ET_{CO2}$, blood oxygenation, respiratory effort (work of breathing [WOB]), pulse transit time (PTT), evidence of hypovolemia using process signaling of PPG signal with single or multiple probe approach that will provide the degree of respiratory-based variation in the PPG signal.
2. Output of PK-based sensors: Measurement of drug levels in various biological media (e.g., breath, saliva, skin, tears, sweat, blood, urine) to guide treatment.

Note: The PD and PK data used to control medical therapy uses computer unprocessed and/or processed data derived from the sensors. In addition, this invention claims the utility of regulatory drug therapy using open loop control systems, where the information does not regulate the drug output from an infusion device but rather informs a health care worker, family member, or the patient that his/her dose requires change or no change, and provides information on the well being of the patient during therapy.

A.XI. Anatomical Location of Infusion Device:

A. Internal—within the body (e.g., subcutaneous, intravascular, intracerebral, intraocular, intrathecal); B. External—Transdermal patches, rectal, vaginal, sublingual.

A.XII. Care Environments:

Hospitals, Hospices, Homes, Nursing Homes, Skilled Nursing Facilities, Surgery Centers, Medical Trauma settings (trauma zones, hospitals, medevac settings and the like), hiking, mountaineering, aeronautical, outer space or subaquatic environments.

General Description of Single Point of Contact (SPOC) Diagnostic System of this invention and Signal Processing Algorithms and Procedures Relevant to Practicing this Invention:

Please see Example 13 below. As can be seen, the conclusion reached in that Example is that the SPOC system "appears to be robust to differences in patient population and performs well relative to other systems on the market. The system uses a unique combination of nasal pressure, saturation, and plethysmography parameters (AC and DC components) and each of the 4 parameters contributes unique information that is utilized by the system. Although there were a few outliers in the validation set that produced a lower than expected correlation with RDI, these outliers are largely caused by two factors: (1) the difference between sleep time and valid data time (our surrogate for sleep), and (2) our focus on correctly discriminating mild and moderate patients. The largest outliers were limited to the very high RDI patients (RDI>80) and the RDI correlation for patients with RDI<80 was 0.96. Even with the sleep-time induced underestimates, the White/Westbrook diagnostic agreement was 93%. With compensation for this sleep time disparity, the diagnostic agreement was 100%."

Thus, utilizing the details, methodology and analysis discussed in Example 13, those skilled in the art are enabled to reproduce the SPOC analysis and outputs relevant to both civilian and medical applications outlined in further detail above and in the additional examples provided below. These outputs permit the selection of appropriate interventions using a closed loop system in which the PD parameters are continually monitored and pharmacologic closed-loop or open-loop interventions are initiated. Thus, as a result of determining that a subject as an unacceptably high RDI for example, whether in a sleep apnea context or in the context of a subject who is not breathing as they should, appropriate medication can be administered by the system, the impact of which is monitored by the subsequent PD parameters of the individual. This results in the system adapting the intervention to match the subsequent state of the subject, either by increasing, decreasing or ceasing the particular intervention. Of course, however, the parameters that may be monitored extend well beyond the RDI measurements to which the information in Example 13 is primarily directed. Examples 1-10 herein below provide further detailed disclosure regarding this aspect of the invention, including, in Example 8, detailed descriptive text for understanding what is shown in FIGS. 1-7.

Scenario B. PPG+SMART—PK/PD and Compliance Monitoring

In situations where it is necessary to not only acquire PD, PK or both PD and PK parameters of a subject, but to also confirm delivery of the correct medication at the correct dosage within appropriate time frames, the PPGcare™ system includes the use of medications which include Self Monitoring and Reporting Technology (SMART), which permits, at a minimum, not only acquisition of PD, PK, or both PD and PK parameters of the individual, but also an independent means for confirming that fluctuations in these parameters correlate with the administration of the SMART medications.

B.I. Summary of this Aspect of the Invention:

In a system for concurrent pharmacokinetic (PK) and/or pharmacodynamic (PD) and adherence monitoring, there is provided an apparatus and method including a photoplethysmograph integrated with Self Monitoring and Reporting Therapeutics (SMART) medication technology, termed, herein PPG$^+$+SMART.

In a system for concurrent pharmacokinetic (PK) and/or pharmacodynamic (PD) and adherence monitoring, there is provided an apparatus and method including a photoplethysmograph integrated with Self Monitoring and Reporting Therapeutics (SMART) medication technology, termed, herein PPG$^+$+SMART.

Accordingly, it is an object of this aspect of the invention to provide a combined adherence monitoring and photoplethysmography plus (PPG+) system, apparatus and method, termed, herein PPG$^+$+SMART.

Another object of this aspect of the invention is to provide a method for integrating SMART (Self Monitoring and Reporting Therapeutics) with PPG in an integrated apparatus, a system and a method, that is, "an integrated tool", which (a) accurately measures the adherence to a regimen for at least one specific drug with (b) technology that can measure in near real-time the pharmacodynamic (biological) effect of the at least one specific drug, criteria which, of course, serve as the basis of defining the efficacy and safety of the at least one specific drug (and indeed, drugs in general).

Another object of this aspect of the invention is to provide a system and method for "complete picture" acquisition for subject(s) [subject(s) and patient(s) are used interchangeably in this invention; where sometimes the term subject(s) is restricted to individuals participating in a clinical trial] undergoing medical treatments, making it possible, for the first time in a self-contained, integrated and fully joined up fashion, to achieve optimized medical management at multiple levels.

Other objects and advantages of this aspect of the invention will be apparent to this skilled in the art upon review of the entire disclosure provided herein and the appended claims.

B.II. Detailed Description of the PPG+SMART Aspect of the Invention:

This embodiment of the invention provides a combined adherence monitoring and photoplethysmography plus (PPG+) system.

SMART (Self Monitoring and Reporting Therapeutics) adherence monitoring is a valuable "personalized medicine tool" that can be used to not only improve the quality of data (safety and efficacy) derived from clinical trials, but also to significantly improve the medical management of a wide variety of disease states. Incorporated herein by reference are the disclosures of aspects of this element of the current invention from the patent disclosures listed in the BACKGROUND OF THE INVENTION section of this disclosure.

This aspect of the present invention extends the SMART system, which is adept at tracking the adherence rate of subjects in a prescribed medication regimen. The extension provided by this patent disclosure comprises concurrent or near concurrent acquisition of pharmacokinetic (PK) and/or pharmacodynamic (PD) parameters. This facilitates the more complete understanding of the biological effects of a medication. This, therefore, permits clinicians, regulatory agencies, doctors, other health care providers, and, in at least one embodiment of this invention, subjects (patients themselves), to make optimal clinical decisions.

This embodiment of the invention comprises an apparatus, a system and a method, that is, "an integrated tool", which (a) accurately measures the adherence to a regimen for at least one specific drug with (b) technology that can measure in near real-time the pharmacodynamic (biological) effect of the at least one specific drug, criteria which, of course, serve as the basis of defining the efficacy and safety of the at least one specific drug (and indeed, drugs in general).

One way to achieve this goal is to "marry" SMART adherence and photoplethysmography (PPG), preferably enhanced by additional technologies (e.g., accelerometer acquired data, including but not limited to motion detection; acquisition of nasal respiratory flow rates or pressure). Such enhanced PPG is termed, herein, "PPG+". The integrated system, method, and apparatus according to this invention, which integrates "PPG+" with SMART technology, is, for convenience, termed herein "PPG++SMART".

PPG+, in a preferred embodiment is located (by the subject, by health care providers, clinicians or the like, depending on the context of its use and emplacement), on the nose (e.g., nasal ala, nasal septum if the patient is on oxygen therapy) or other "central" locations such as the cheek, lip and pre- or postauricular (in front of or behind the ear). Such emplacement provides a Single Point of Contact ("SPOC"), and enables the acquisition of comprehensive and near real time assessment of, among other possible physiological parameters, cardiorespiratory function.

PPG++SMART, as disclosed herein, facilitates "complete picture" acquisition for subject(s). This makes possible, for the first time in a self-contained, integrated and fully joined up fashion, optimized medical management at multiple levels, including but not limited to:

1) Accurate and real-time or near real-time acquisition of data tracking or the rate of adherence of subject(s) to prescribed medication regimens via the SMART components of the system;

2) Measurement of biological (pharmacodynamics and/or pharmacokinetic) effects of drugs underlying key safety and/or vitality parameters via the PPG+ components of the system, including but not limited to, measurement of:
  a. deleterious or adverse cardiac states including, but not limited to, orthostatic hypotension, impaired sympathovagal balance to heart, ventricular tachyarrhythmias such as torsade de pointes, impaired cardiac output such as indicators of congestive heart failure;
  b. respiratory states, including, but not limited to impaired ventilation and oxygenation secondary to various conditions such as asthma/bronchospasm, pulmonary edema, heart failure, and the like;
  c. locomotor activity, including but not limited to sedentary actions, sedation, seizure activity, tremor, general hyperactivity;
  d. key biological indicators of toxicities associated with drug overdosing or normal doses, known as adverse drug reactions (ADRs), which are frequently caused by drug-drug interactions (DDIs) due to pharmacokinetic and/or pharmacodynamic drug interactions, are rapidly diagnosed, monitored, and managed.

3) Measurement of biological effects of drugs that underlie key efficacy parameters, including but not limited to, beneficial cardiac (e.g., antihypertensive agents lowering blood pressure and reducing heart rate via various mechanisms such as blunting sympathetic input to the heart, inhibition of angiotensin-converting enzyme, blockade of angiotensin receptors, and/or by direct vasodilatory effects on blood vessels, etc.), respiratory (e.g., drugs to treat lung dysfunction associated with asthma, COPD, bronchitis, lung infections, bronchiectasis, and/or pulmonary hypertension, etc.), and locomotor activity (e.g., improved ambulation with antidepressants, relief of negative symptoms and less sedation in schizophrenics treated with antipsychotics, less tremor and improved ambulation with anti-Parkinsonism meds, less motor activity in ADHD patients treated with ADHD meds, etc.) actions.

4) Identification of underlying clinical status in a wide variety of diseases (e.g., metabolic syndrome, diabetes, hypertension, COPD, asthma, CHF, etc.).

By utilizing the PPG++SMART system according to this invention, medical decision making is markedly improved in both the clinical trials and disease management settings, because, for the first time, in an integrated and joined-up system, all of the above factors can now be acquired, integrated and presented to/reviewed by the relevant clinical personnel.

Incorporated herein by reference are elements of a substantial portfolio of patent disclosures, listed in the BACKGROUND OF THE INVENTION portion of this disclosure, covering both presumptive and definitive adherence monitoring strategies utilizing the SMART technology, as well as PPG-based technology when used in the context of open and/or closed-loop medication delivery and monitoring. The present patent disclosure provides a combined system with the addition to several new embodiments, for use in an integrated PPG++SMART system.

The key overarching conceptual basis of the instant "combined" PPG++SMART system, including, optionally, acquisition of supplementary/confirmatory cardiorespiratory parameters via additional modalities, provides the only practical system (outside of closed research units) from which a healthcare provider, pharmaceutical company, or clinical researcher can have at their disposal in near real-time all of the information required to make informed decisions regarding drug therapy based on biological response (pharmacodynamic) data/profile.

In various embodiments of the combined PPG++SMART apparatus of the present system, key components for inclusion are enumerated below. It will be appreciated by those skilled in the art and by instrument manufacturers following the guidance provided in the present disclosure, that, depending on the particular context in which the PPG++SMART system is deployed, some or all of the following components are included or eliminated, to ensure optimum operability, minimal complexity for a given context, and optimum responsiveness:

An accelerometer—in addition to determining patient/subject position in order to correct the PPG signal amplitude, inclusion of an accelerometer facilitates:
  Determination of the degree of locomotion (level of sedentary status) in particular patients, including but not limited to those suffering from depression or schizophrenia. For example, drug-induced relief of the negative symptoms of schizophrenia or improvement in depression should manifest as increased locomotion (reduced sedentary lifestyle).
  Determination of whether a patient is making meaningful movements (thus providing a watchdog function, if PPG fails, e.g. sensor falls off during the night or if a patient falls, etc.)
  Determination, in conjunction with PPG, of sleep staging (often referred to as "actigraphy")
  Determination of presence of seizure activity Assessment of the efficacy of a drug used for a movement disorder such as Parkinson's disease (decrease in tremor)

Detection of falls or sudden changes in position

Assessment of the effect of position on cardiorespiratory parameters (e.g. orthostasis, postural hypotension: common with antihypertensive agents, antipsychotics, Parkinsonism medications)

A Photoplethysmograph (PPG), or equivalent, which, in addition to the core data obtainable from standard pulse oximetry systems, permits acquisition of additional derived variables from the PPG signal, including, but not limited to:

Heart Rate Variability (HRV). By providing a measure of sympathetic and parasympathetic (termed sympathovagal) balance and input to the heart, it has long been known that HRV is an important diagnostic tool for a number of diseases, in particular cardiovascular disease. Changes in HRV are strong predictors of mortality after myocardial infarction and ischemic events. In addition HRV can be used in the evaluation of congestive heart failure, diabetes, SIDS and survival in premature infants. In order to use HRV clinically, the heart rate must be corrected for respiratory excursions, because respiration alters autonomic tone (e.g., vagal) input to the heart, which independently alters SA node function and therefore heart rate. PPG can provide both heart rate and respiratory rate and therefore is a unique parameter that can be used to calculate HRV without the need for other devices (e.g. ECG, chest bands, abdominal bands, transthoracic impedance) to determine respiratory rate. Acquisition of these parameters also makes analysis of the data easier and more robust. The technology described herein allows HRV analyses to be accurately done for the first time using a single point of contact (SPOC) sensor, preferably located on the nose (e.g., nasal ala).

HRV also provides a window into autonomic nervous system function as both the sympathetic and parasympathetic nervous systems affect the PPG signal. As stated by Acharya et. al. "HRV analysis is the ability to assess overall cardiac health and the state of the autonomic nervous system (ANS) responsible for regulating cardiac activity . . . . The ANS have sympathetic and parasympathetic components. Sympathetic stimulation, occurring in response to stress, exercise and heart disease, causes an increase in HR by increasing the firing rate of pacemaker cells in the heart's sino-atrial node. Parasympathetic activity, primarily resulting from the function of internal organs, trauma, allergic reactions and the inhalation of irritants, decreases the firing rate of pacemaker cells and the HR, providing a regulatory balance in physiological autonomic function. The separate rhythmic contributions from sympathetic and parasympathetic autonomic activity modulate the heart rate (RR) intervals of the QRS complex in the electrocardiogram (ECG), at distinct frequencies. Sympathetic activity is associated with the low frequency range (0.04-0.15 Hz) while parasympathetic activity is associated with the higher frequency range (0.15-0.4 Hz) of modulation frequencies of the HR. This difference in frequency ranges allows HRV analysis to separate sympathetic and parasympathetic contributions evident. This should enable preventive intervention at an early stage when it is most beneficial." (Acharya U R, et. al. Heart rate variability: a review. Med Bio Eng Comput (2006) 44:1031-1051).

A number of other derived parameters include, but are not limited to, acquisition in an integrated system according to this invention:

Pulse Transit Time—wide application in sleep and other disease diagnostics

Pulses Wave Velocity

Endothelial Dysfunction

Arterial Pressure Wave Shape and Amplitude

Ankle-Brachial Index

Peripheral Artery Occlusion

Arrhythmias

Breath-based medication adherence monitor (presumptive and definitive) using "taggants", utilizing components of the SMART technology.

B.III. Self Monitoring and Reporting Therapeutics (SMART):

A great deal of information about the SMART system components of the present combined PPG⁺+SMART system of this invention is available at, and is herein incorporated by reference from, http://www.xhale.com/smart/index.asp The following information is provided herein to further enable those skilled in the art to understand, implement and practice this aspect of the invention:

B.IV. About SMART™ Drugs

Self-Monitoring And Reporting Therapeutics (SMART™) technology enables the creation of a breath-detectable version of any pharmaceutical drug. SMART™ drugs release unique markers in the breath within minutes of ingestion, which can then be detected in the breath by using a small hand-held SMART monitor. SMART system is the only existing technology which can definitively document patient adherence to a prescribed medication dosing regimen.

Market applications for SMART drugs include:

Disease Management: SMART versions of drugs targeted at patients where compliance is critical and challenging, such as antipsychotic drugs and therapeutics for Alzheimer's and other cognitive impairment diseases, would provide an advantage to patients, physicians and family caregivers.

Managed Care: One type of disease management care setting which deserves special mention is managed care. SMART versions of drugs targeted at large patient subpopulations where improved patient adherence, tied to positive patient reward systems, can save money while providing better outcomes.

Pharmaceutical Clinical Trials: SMART versions of clinical trial medications will provide the only accurate and definitive means for tracking and recording patient adherence to the clinical trial dosing protocol.

While the first SMART drugs report via the breath on patient adherence, later generations will report on patient metabolism and therapeutic blood levels of the active pharmaceutical ingredient (API).

SMART has the potential to markedly improve the safety and efficacy of existing drugs while simultaneously providing market exclusivity from patent protection on SMART technology.

B.V. How SMART™ Works

A SMART drug incorporates a taggant (marker) that makes the drug breath-detectable via a small electronic exhalation monitor. Capsules containing the taggants are available under license from Xhale, Inc. through established capsule manufacturers, or the taggants can be incorporated into coatings. The presence of the taggants does not change the way the active pharmaceutical ingredient (API) is manufactured by the drug company, and has no impact on the PK/PD of the API.

The SMART breath monitor serves as an electronic medication reminder for the patient, reminding them to take the medication. The patient ingests the drug, pushes a button on the monitor, and a few minutes later the monitor reminds the patient to blow into the breath collection tube of the monitor. The monitor then detects the metabolite of the marker on the patient's breath, proving definitively that the medication was actually ingested. The time and date of the dose is recorded and transmitted for use by the healthcare provider, organization or trial center involved.

B.VI. Critical Need for Adherence

According to the National Council on Patient Information and Education (NCPIE), approximately 50% of patients are not taking their medications as prescribed. Lack of medication adherence leads to unnecessary disease progression, disease complications, reduced functional abilities, a lower quality of life, and even death. But one of the most serious results of poor medication adherence is the emergence of drug resistant strains in diseases such as tuberculosis and HIV/AIDS.

The ramifications of poor prescription medication adherence affect virtually every aspect of the health care system with a cost of approximately $177 billion annually to the U.S. economy. Besides an estimated $47 billion each year for drug-related hospitalizations, not taking medications as prescribed has been associated with as many as 40% of admissions to nursing homes and with an additional $2,000 a year per patient in medical costs for visits to physicians' offices.

One serious example is Tuberculosis (TB): Nearly 2 billion persons—about one third of the world's population—are infected by TB. In 2008 an estimated 9 million people will develop TB and 2 million people will die from this contagious disease. TB is caused by *Mycobacterium tuberculosis* bacteria that are spread in airborne droplets when people with active TB sneeze or cough. TB can be cured by taking several strong antibiotics daily for at least six months, but studies show that nearly half of patients fail to follow their medications regimen due to unpleasant side-effects, complex treatment regimens and a belief that they can stop treatment when they start to feel better. Poor medication adherence causes people to remain infectious longer, increasing the threat to public health, but also contributes to the emergence of multidrug-resistant TB (MDR-TB). MDR-TB takes longer to treat with medications that have more side-effects are much more expensive.

The breath-based medication adherence system is the only technology on the market today that can verify that the right person took the right dose of the right medication via the right route at the right time.

B.VII. SMART™ in Disease Management

SMART drugs have numerous applications in Disease Management. Early candidates for SMART drugs are conditions where behavioral challenges make patient adherence especially critical, including management of cognitive impairment (Alzheimer's and related diseases), seizure disorders and certain psychiatric disorders.

Psychiatric Disorders—A SMART version of an antipsychotic drug would provide an unparalleled method for monitoring patient adherence, providing definitive proof of medication adherence and fool-proof reporting of non-compliance.

Cognitive Impairment—Management of Alzheimer's and similar cognitive impairment diseases would benefit from a SMART version of treatment drugs which would report via the breath on patient adherence, with the SMART system providing notification to caregivers or family in the event of non-compliance.

Other diseases where SMART drugs can benefit patients include diabetes, CHF, COPD, stroke and neurological diseases, where measuring patient adherence can be a key tool in determining efficacy of therapeutic agents.

| Therapeutic Area | Product Rationale |
|---|---|
| Alzheimer's | Greater convenience for caregiver and patient |
| Epilepsy | Product would and document dose timing for physician management |
| Oncology | New generation of LT oral meds requires full adherence to work. SMART version will allow ADR monitoring, justify reimbursement. |
| Depression | Adherence will help clarify and separate any correlation between dose timing and AEs<br>Morning dosing vs. night dosing recommendation needs to be followed (to activate drug action)<br>Notable food effects mean dose ingestion must be carefully managed with respect to meals |
| Psychosis | "Perfect" adherence: Optimize dose, improve patient management<br>Safer: self-reporting metabolic or CYP 450 impairments for ADR "warning flag"<br>Provide definitive documentation of dosing for insurers, caregivers, trialists → enable positive incentives in intermittent compliers |
| Asthma/COPD | Confirm that a full dose was received, metabolized<br>Monitor for negative CYP450 conditions<br>Increase efficacy through better dosing |

B.VIII. SMART™ in Managed Care

As the health benefits industry moves increasing toward consumer-focused products and processes, Managed Care Organizations (MCOs) will be able to offer their members SMART drugs to better manage their health.

SMART drugs can reduce healthcare costs by empowering the MCO members through effective medication reminder/reward systems while empowering the organization through creation of patient adherence records. A definitive record of patient adherence will allow the physician to provide better care and make more informed decisions, and it will allow the MCO to integrate the SMART system into reward programs for patients who comply with their medication regimen.

MCOs can provide SMART versions of drugs for large subpopulations of patients such as diabetes management and hypertension, tying definitive reporting on patient adherence to positive patient rewards.

Physicians caring for patients who are who are unresponsive to a medication regimen can utilize a SMART version of a drug, measuring patient adherence before increasing dosage or adding another drug to the regimen.

A mental health specialty practice group managing many outpatient clients on anti-psychotic medications can utilize a SMART version of the medication to monitor outpatient compliance, and to receive a warning notification if a patient becomes non-compliant.

B.IX. Next Generation SMART™

The current generation of SMART drugs report on patient adherence via the breath, but Xhale, Inc. is developing versions that will report on patient metabolism and therapeutic blood levels of the active pharmaceutical ingredient (API).

A future SMART drug that reported on therapeutic blood levels of the API would allow real-time, onsite therapeutic drug monitoring (TDM). This in turn would provide an opportunity for certain drugs with well established efficacy but which have issues of toxicity which require blood level monitoring.

Future SMART drugs that report via the breath on patient metabolism would provide measures of drug pharmacokinetics that are important to patient safety and to the correct analysis of data in clinical trials.

In addition to working on advances in SMART drugs, Xhale, Inc. is continuing development of future generations of the monitors that sample the breath and detect the drug and related markers. Future generations of these monitors will be smaller, more portable and more integrated with other electronics the patient carries, increasing the ease of use and convenience of the system.

B.X. SMART™ in Clinical Trials

Billions of dollars are spent each year on drug development, and the data generated in the clinical trials of those drugs is entirely dependent upon the trial participants taking the medication as prescribed. There is currently no way other than direct observation to ensure that trial participants are taking the trial medication as prescribed, and direct observation is prohibitive for many reasons.

Estimates of the number of patients enrolled in clinical trials who do not take the study drug as prescribed range from 15% to 50%. Trial participants not taking the study drug as prescribed confounds results, which drives an increase in enrollment by as much as 40%. This in turn brings increases the cost of clinical trials, and unnecessarily lengthens trial duration.

A drug at any stage of development can easily be converted into a SMART version by incorporation of a capsule or coating with the SMART taggants, making it breath-detectable. Phase II and Phase II clinical trials can then include adherence monitoring with the SMART system, producing reliable and definitive data which can help in analysis.

Because the SMART taggants can remain part of the approved drug, the approved drug may include the taggants when it is launched into the marketplace. Even if the pharmaceutical sponsor does not wish to pursue a label claim for breath-detectable monitoring for the drug, the inclusion of the taggants makes Phase IV post-marketing surveillance monitoring feasible.

The SMART system is the only existing technology of which the present applicants are aware which can definitively document patient adherence to a prescribed medication dosing regimen.

B.XI. Product Life Management

Therapeutic drugs take years to develop and gain regulatory approval, and often have less than 10 years of patent life remaining by the time they reach market. Some drugs can be made safer and more efficacious by developing a breath-detectable SMART version that reports on patient adherence, or by incorporating future SMART capabilities such as reporting on blood concentration (therapeutic drug monitoring) or metabolic capacity. For opportunities such as these, pharmaceutical companies can enhance their brand investment by introducing a SMART version of the drug, which will derive additional patent protection from the underlying SMART patents.

The SMART version of the drug will have improved safety and efficacy (e.g., an Alzheimer's drug that reports to a family caregiver if the patient misses a scheduled dose of the drug, or an anti-depressant that confirms adolescent patients did not skip a dose), and as a result of the underlying Xhale, Inc. patents the SMART drug version will enjoy additional market exclusivity.

Initial SMART designs for leading drugs in many therapeutic categories (including asthma, epilepsy, psychosis, depression, pain, coagulation, cancer and Alzheimer's disease) have been designed where a leading drug on the market has limited remaining patent life, yet could be made more efficacious via a SMART version.

B.XII. PPG$^+$ for Integration with Self Monitoring and Reporting Therapeutics (SMART):

About PPGcare™

Introducing PPGcare™

PPGcare™ provides real-time monitoring and assessment of the total pharmacodynamic (PD) impact of drug delivery on the patient's well-being. The system monitors the physiological effects of a patient's drug regimen on their cardiopulmonary status. In addition to the commonly monitored vital signs such as heart rate and oxygen saturation, PPGcare™ measures respiratory rate and analyzes photoplethysmography (PPG) signals for hypopnea, central and obstructive apnea, and trends these values to determine the degree of respiratory depression and respiratory "effort". Because these measurements are obtained from sensors at a "single point of contact" (SPOC) on the nasal ala, surrogates for cerebral blood flow and venous capacitance can be measured.

From the central alar source, the PPGcare™ provides real-time heart rate, oxygen saturation, respiration rate, respiratory effort, and respiratory obstruction index. The system directly monitors the PD effects of all the factors that may contribute to hypopnea and apnea, and monitors the combined effects of hypoxemia, opioids, other drugs, and the patient's physiological state. PPGcare™ ensures the safest pain medication infusion based on a robust and accurate PD assessment of the patient's respiratory and cardiovascular status.

PPGcare™ alerts a healthcare professional immediately if a patient is trending towards respiratory distress or depression, allowing early intervention to prevent respiratory arrest, and it can discontinue medication infusion until a healthcare professional intervenes.

How it Works

PPGcare™ Technology Utilizes Photoplethysmography (PPG)

PPGcare™ technology utilizes photoplethysmography (PPG), a measurement that can be obtained from pulse oximeters. Instead of using a sensor on an extremity, like a fingertip, the PPGcare™ system uses a tiny, comfortable SPOC sensor array that attaches to the ala of the patient (or if the patient is on nasal oxygen, from the nasal septum). Unlike a pulse oximeter located on an extremity, the source of the signal for the PPGcare™ is the arterial plexus (Kiesselbach's plexus on the nasal septum/equivalent on the nasal alae) fed by the last branch of the external and first branch of the internal carotid arteries. The result is a magnitude higher signal with markedly improved signal to noise ratio, and measurement of a wide range of physiologic parameters that are input into proprietary algorithms to provide early warning of respiratory and cardiovascular changes.

From the central alar source, the PPGcare™ provides real-time heart rate, oxygen saturation, respiration rate, respiratory effort, and respiratory obstruction index. The system directly monitors the PD effects of all the factors that may contribute to hypopnea and apnea, and monitors the combined effects of hypoxemia, opioids, other drugs, and the patient's physiological state.

Use in Infusion Pump Monitoring

Introducing PPGcare™

PPG provides real-time monitoring and assessment of the total pharmacodynamic (PD) impact of drug delivery on the patient's well-being. The system monitors the physiological effects of a patient's drug regimen on their cardiopulmonary status. In addition to the commonly monitored vital signs such as heart rate and oxygen saturation, PPGcare™ measures respiratory rate and analyzes photoplethysmography (PPG) signals for hypopnea, central and obstructive apnea, and trends these values to determine the degree of respiratory depression and respiratory "effort". Because these measurements are obtained from sensors at a "single point of contact" (SPOC) on the nasal ala, surrogates for cerebral blood flow and venous capacitance can be measured. PPGcare™ alerts a healthcare professional immediately if a patient is trending towards respiratory distress or depression, allowing early intervention to prevent respiratory arrest, and it can discontinue medication infusion until a healthcare professional intervenes.

PPGcare™—Complete Pharmacodynamic Monitoring

Today, pulse oximeters are relied upon to provide oxygen saturation and heart rate. But the distal location of the sensors, usually the patient's fingertip, significantly limits the information that can be obtained. While fingertip placement is sufficient for these measurements, the fingertip source is too remote from the carotid artery to provide other valuable information, and peripheral blood flow can be adversely affected by a wide range of medications and physiologic states that make measurements unreliable. Capnography, a mandated safety measure for patients receiving anesthesia, can measure end-tidal carbon dioxide and alert to impending respiratory failure, but is only reliable in intubated patients, and is unsuited for use on general hospital wards. End-tidal carbon dioxide measurements are prone to numerous conditions which can lead to faulty data and interpretation.

From the central alar source, the PPGcare™ provides real-time heart rate, oxygen saturation, respiration rate, respiratory effort, and respiratory obstruction index. The system directly monitors the PD effects of all the factors that may contribute to hypopnea and apnea, and monitors the combined effects of hypoxemia, opioids, other drugs, and the patient's physiological state. PPGcare™ ensures the safest pain medication infusion based on a robust and accurate PD assessment of the patient's respiratory and cardiovascular status.

Opportunities

The Need for New Technology

Infusion pump manufacturers are subject to challenging regulatory pressures, in large part as the result of safety concerns. With the FDA's Infusion Pump Improvement Initiative, focus on the industry will intensify. As Jeffrey Shuren, M.D., Director of the FDA's Center for Devices and Radiological Health, said upon the new initiative's announcement, "These pumps often provide critical fluids to high-risk patients, so failures have significant implications. It is time for a more comprehensive approach than we've taken to date." PPGcare™ technology addresses issues discussed in this initiative by introducing a comprehensive level of safety to new and existing infusion pump platforms.

Between 2005 and 2009, 56,000 adverse events involving infusion pumps were reported to the FDA. Pumps can be mis-programmed, malfunction, and not respond to a patient's physiological responses to medications and underlying medical conditions. Whatever the cause, healthcare professionals need an innovative solution that will immediately alert them when dangerous events occur, especially in instances where the patient's medical condition deteriorates rapidly.

An Innovative Solution for Infusion Pump Safety

The PPGcare™ technology is now in a prototype stage, and is being readied for human trials. The first generation is being designed to monitor and alert healthcare professionals before adverse events occur and could automatically slow or stop drug infusion. It could be a stand-alone monitor for any existing infusion pump system, or it could be incorporated into a third party's next-generation infusion pumps.

Future generations of the technology could offer further features in correlating patient vital signs data to pump infusion rates, offering increased patient care and pump safety advancements for the healthcare professional.

Figure 8:
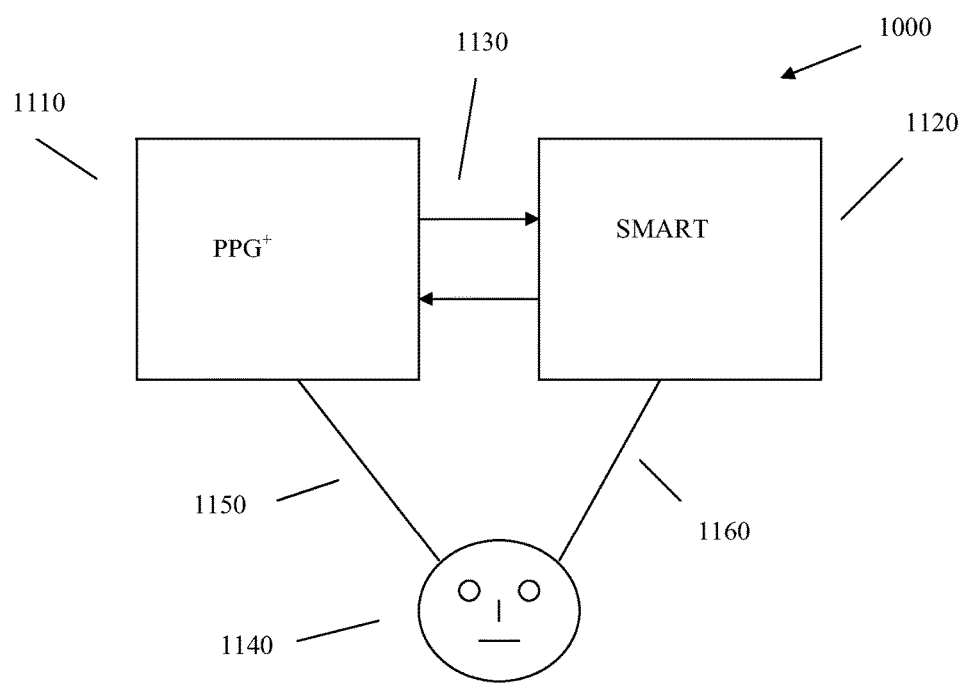
FIG. 8 shows an integrated PPG$^+$+SMART system according to this invention.

B.XIII. The Combined PPG$^+$+SMART System According to this Invention:

With reference now to FIG. 8, there is provided a PPG$^+$+SMART system 1000 according to this invention comprising:

The PPG$^+$ component 1110 of the system, the SMART component 1120 of the system, between which there is a two-way communication channel 1130 so that data acquired by the PPG$^+$ component 1110 of the system is available to the SMART component 1120 of the system, and vice-versa. The PPG$^+$ component 1110 of the system is operatively connected to a subject 1140 via communication channel(s) 1150, and the SMART component 1120 of the system is operatively connected to a subject 1140 via communication channel(s) 1160.

In this manner, there is provided an integrated PPG$^+$+SMART system according to this invention. All of the data acquisition elements of PPG operative interface with subjects and signal processing and data mining acquired via this interface may be treated in ways disclosed in the patent documents herein incorporated by reference, and which hereafter become known. In addition, as disclosed in Example 13, there is provided details of a closed-loop or open-loop PPG controlled system for medication administration. By combining the SMART component of this invention, with the PPG component of that system, there is provided a novel, integrated, and optionally self-contained and portable system which may be worn by subjects in a wide variety of contexts, including, but not limited to, in in-patient contexts, in field exploration contexts, where the subject may encounter challenging conditions and may experience injury, in which case, the subject's potential for survival is maximally enhanced by a self-contained system which administers appropriate medications while at the same time monitoring key PD and/or PK parameters. In the context of clinical trials, the integration of the SMART component of this invention permits presumptive and/or definitive monitoring of subject(s) rate of adherence in taking the medication(s) being tested in the prescribed regimen. In this way, as PD and/or PK parameters are measured, in an integrated way, the appropriate personnel will be concurrently armed with adherence data. This permits the clinicians to determine with a much higher degree than has heretofore been possible, the correlation between such PD and/or PK parameters with the timing, dosage and adherence to the prescribed drug regimen.

It will be appreciated that the specifics provided herein to enable those skilled in the art to make and use the invention disclosed herein, are non-limiting, and are provided to ensure an adequate written description, including of the best mode, for practicing the herein disclosed invention. Equivalents, modifications and the like of the system, method and apparatus disclosed herein, to the extent that those skilled in the art will appreciate, from the present disclosure, the ability to interchange such equivalents with elements disclosed herein, are likewise included within the scope of the invention disclosed herein. The scope of the invention disclosed herein may be apprehended by reference to the appended claims.

Scenario C: Infusion-Pump Agnostic PPG-Based Safety Over-Ride of Medication Infusion In situations where a medication is being delivered to a subject via an infusion pump, whether in an open-loop or closed-loop context, and an adverse individual parameter is detected from monitoring the total PK, PD, or both PK and PD parameters, (including specific parameters discussed in detail herein below), of the individual undergoing infusion, the PPGcare™ system in one embodiment includes an infusion pump agnostic component to reduce or terminate the infusion and to alert appropriate healthcare professionals that the individual is in need of attention.

C.I. Summary of this Aspect of the Invention

A novel monitoring system to improve infusion pump safety, preferably using a single point of contact (SPOC) sensor and an infusion pump tubing occlusion device.

This aspect of the invention provides a novel monitoring system to improve infusion pump safety using, preferably, a single point of contact (SPOC) sensor and an infusion pump tubing occlusion device is provided which facilitates improved safety in use of infusion pump delivery of medications. The system monitors critical parameters of a subject undergoing such treatment, and, depending on select subject Pharmacodynamic (PD) and/or Pharmacokinetic parameters (PK), as monitored via an SPOC sensor, a tubing occlusion device is actuated to limit or shut-off delivery of medications by the pump.

Accordingly, it is a first object of this aspect of the invention to provide a novel safety system for use with existing infusion pumps for increased safety in the delivery of medications to subjects.

A further object of this aspect of the invention is to provide a device for occlusion of tubing running from an infusion pump to a subject when relevant physiological parameters of the subject indicate that such occlusion is required for the safety of the subject.

Further objects, advantages and embodiments of this aspect of the invention will be apparent to those skilled in the art from a review of the entire disclosure provided herein and the appended claims.

C.II. Detailed Description of this Aspect of the Invention

Information on PPG, SPOC and the cardiorespiratory parameters that are available for collection, processing and analysis appear in multiple invention disclosures/patent applications and patents filed by certain of the inventors of the present patent disclosure, and such disclosures are herein incorporated by reference to the extent needed to practice this aspect of the invention to the full scope as herein disclosed and claimed.

The PPG+ technology described herein for improving the safety of infusion pump controlled medication delivery to a subject is covered by at least the following patent documents, each of which is herein incorporated by reference, including, as appropriate, pending and issued international and national equivalents thereof:

U.S. Pat. No. 6,909,912, Non-Invasive Perfusion Monitor and System, Specially Configured Oximeter Probes, Methods of Using Same, and Covers for Probes; WO/2004/000114, Perfusion Monitor and System, Including Specifically Configured Oximeter Probes and Covers for Oximeter Probes; U.S. Pat. No. 7,127,278, and U.S. Pat. No. 7,024,235, Novel Specially Configured Lip/Cheek Pulse Oximeter/Photoplethysmography Probes, Selectively With Sampler for Capnography and Covering Sleeves for Same; US 2007-0027375 A1, Optimized Gas Supply Using Photoplethysmography; WO/2005/065540, Novel Specially Configured Nasal Pulse Oximeter; WO/2006/086010, METHODS AND DEVICES FOR COUNTERING GRAVITY INDUCED LOSS OF CONSCIOUSNESS AND NOVEL PULSE OXIMETER PROBES; WO/2006/116469 METHOD AND APPARATUS FOR DIAGNOSING RESPIRATORY DISORDERS AND DETERMINING THE DEGREE OF EXACERBATIONS; US 2008-0067132 A1, Method for Using Photoplethysmography to Optimize Fluid Removal During Renal Replacement Therapy by Hemodialysis or Hemofiltration; (WO/2008/020845) METHODS AND DEVICES FOR CENTRAL PHOTOPLETHYSMOGRAPHIC MONITORING METHODS Features/parameters can be monitored by "SPOC plus" (including a means for terminating flow from an infusion pump), according to this invention, include:

An accelerometer—in addition to determining patient/subject position in order to correct the PPG signal amplitude, an accelerometer provides valuable data to permit appropriate personnel or a subject to:
  Determine the degree of locomotion (level of being sedentary) in particular patients, including but not limited to those suffering from depression, schizophrenia, and/or attention deficit hyperactivity disorder (ADHD). For example, drug-induced relief of depression and ADHD should manifest as increased and decreased locomotor activity, respectively.
  Whether a patient is making meaningful movements (a watchdog function if PPG fails, e.g. sensor falls off during the night or if a patient falls, etc.)
  Can be used in conjunction with PPG for staging sleep (often referred to as "actigraphy"), and determining the beneficial and detrimental effects of drugs on sleep
  Can be used to determine presence of seizure activity
  Can be used to assess the efficacy of a drug used for a movement disorder such as Parkinson's disease (decrease in tremor)
  Can detect falls or sudden changes in position
  Can be used to assess the effect of position on cardiorespiratory parameters (e.g. Orthostasis, postural hypotension: common with antihypertensive agents, antipsychotics, Parkinsonism medications)
Additional derived variables from the PPG signal
  An important derived variable is Heart Rate Variability (HRV). By providing a measure of sympathetic and parasympathetic (termed sympathovagal) balance and input to the heart, it has long been known that HRV is an important diagnostic tool for a number of diseases, in particular cardiovascular disease. Changes in HRV are strong predictors of mortality after myocardial infarction and ischemic events. In addition HRV can be used in the evaluation of congestive heart failure, diabetes, SIDS and survival in premature infants. In order to use HRV clinically, the heart rate must be corrected for respiratory excursions, because respiration alters autonomic tone (e.g., vagal) input to the heart, which independently alters SA node function and therefore heart rate. PPG can provide both heart rate and respiratory rate and therefore is a unique parameter that can be used to calculate HRV without the need for other devices (e.g. ECG, chest bands, abdominal bands, transthoracic impedance) to determine respiratory rate. These also make analysis of the data easier and more robust.

The technology described herein allows HRV analyses to be accurately done for the first time using, preferably, a single point of contact (SPOC) sensor, preferably located on the nose (e.g., nasal ala). It will be appreciated by those skilled in the art reading the instant disclosure that the present invention may, of course, be practiced without limiting the practice thereof to the use of an SPOC sensor. Multiple points of contact may be used, and multiple different sensors may be used, without departing from the heart of the present invention. However, for purposes of ease of use, portability, integration, reliability and accuracy of data acquired, we have found that using SPOC sensor technology in combination with the infusion pump tubing occlusion device according to this invention provides a safe, effective and easily implemented system.

With regard to parameters acquired, whether via a SPOC sensor or via multiple points of subject contact using multiple different sensors, it is noted that HRV also provides a window into autonomic nervous system function, as both sympathetic and parasympathetic nervous system affect the PPG. As stated by Acharya et. al. "HRV analysis is the ability to assess overall cardiac health and the state of the autonomic nervous system (ANS) responsible for regulating cardiac activity." See Acharya U R, et. al. Heart rate variability: a review. Med Bio Eng Comput (2006) 44:1031-1051, which further states: "The ANS have sympathetic and parasympathetic components. Sympathetic stimulation, occurring in response to stress, exercise and heart disease, causes an increase in HR by increasing the firing rate of pacemaker cells in the heart's sinoatrial (SA) node.

Parasympathetic activity, primarily resulting from the function of internal organs, trauma, allergic reactions and the inhalation of irritants, decreases the firing rate of pacemaker cells and the HR, providing a regulatory balance in physiological autonomic function. The separate rhythmic contributions from sympathetic and parasympathetic autonomic activity modulate the heart rate (RR) intervals of the QRS complex in the electrocardiogram (ECG), at distinct frequencies. Sympathetic activity is associated with the low frequency range (0.04-0.15 Hz) while parasympathetic activity is associated with the higher frequency range (0.15-0.4 Hz) of modulation frequencies of the HR. This difference in frequency ranges allows HRV analysis to separate sympathetic and parasympathetic contributions evident. This should enable preventive intervention at an early stage when it is most beneficial."

A number of other derived parameters are listed in the several additional patent documents listed and hereby incorporated by reference herein, but descriptions and use in an integrated manner can be further elucidated. Examples include:

Pulse Transit Time—wide application in sleep and other disease diagnostics
Pulses Wave Velocity
Endothelial Dysfunction
Arterial Pressure Wave Shape and Amplitude
Ankle-Brachial index
Peripheral Artery Occlusion
Arrhythmias The effects of opioids on cardiorespiratory function have been studied and modeled. Opioids induce cardiorespiratory changes by acting on the brainstem (and to a more limited extent on the cerebral cortex). The effects of opioids alone, or in combination with other medications are summarized by Pattinson: "*Measuring opioid effects on breathing in humans*—In humans, opioids cause respiration to slow and become irregular, leading to hypercapnia and hypoxia. Although single measurements of $Pa_{CO2}$ are unhelpful in predicting impending respiratory depression, the techniques described below have helped interpret opioid-induced changes in respiratory control in humans from a mechanistic point of view. Modeling has successfully explained pharmacodynamic and pharmacokinetic interactions between $CO_2$ and opioids on breathing. With a gradual increase in opioid levels, for example, with a constant rate infusion, progressive respiratory depression causes gradual hypercapnia that contributes to the maintenance of respiration. On the other hand, a fast rise in opioid receptor occupancy resulting from an IV bolus would lead to apnea until the $Pa_{CO2}$ rises to its steady-state value. This explains why drugs with slower receptor binding (e.g., morphine) may be safer than those that bind more quickly (e.g., alfentanil and remifentanil), despite equianalgesic effects. Although reduced ventilatory frequency and pattern is well described with opioids, currently no human studies have fully investigated the subtle effects of opioids on respiratory rhythm. 'Quantal' breathing has not been investigated. Modeling approaches have been used to examine the interaction between respiratory variability and chemo reflex responsiveness, but have not as yet been used to investigate drug effects on breathing. Using such approaches, it could be possible to simultaneously identify drug effects on chemoreception and pattern generation, in human volunteers and patients. The closed nature of the chemoreflex loop means that changes in breathing will affect $Pa_{O2}$ and $Pa_{CO2}$, and vice versa. As breathing is also modulated by many factors other than chemoreflexes, opening the chemoreflex loop by delivering hypoxic and hypercapnic challenges allows straightforward estimation of chemoreflex gain. Specialized experimental protocols and equipment allow dissection of the peripheral and central components of the respiratory chemoreflex feedback loop. Opioids profoundly depress the HRV and HCVR through depression of central and peripheral chemoreception, as described above. The degree of respiratory depression appears to vary between drugs, even at equianalgesic levels, but there are currently no opioids available that are devoid of respiratory side-effects.

Although the HRV is mediated by the peripheral chemoreceptors (which express opioid receptors), Bailey and colleagues demonstrated, in healthy human volunteers, that morphine is likely to exert its depressant effect on HRV by direct action in the brainstem. They compared HRV between a group that received intrathecal morphine with a group that received an approximately equianalgesic dose of IV morphine. In the intrathecal morphine group, they observed a substantial reduction in the HRV, despite extremely low plasma levels. The authors concluded that opioids depress the HRV through central mechanisms, but did not propose a mechanism or site of action. As more recent evidence suggests that MOP agonists inhibit activity in the dorsolateral and medial parts of the NTS, an area which contains chemoreceptive neurons and is the location of the afferent inputs from the carotid body, we can hypothesize that opioids affect the peripheral chemoreflex pathway by interrupting it where impulses synapse in the brainstem factors. These include interspecies differences and by the fact that drug interactions, sleep, pain, genetic differences, and the stress response may also have important contributions to the ultimate respiratory output." See Pattinson KTS, Opioids and the control of respiration. Br j Anaesth 2008; 100:747-758.

Figure 9:
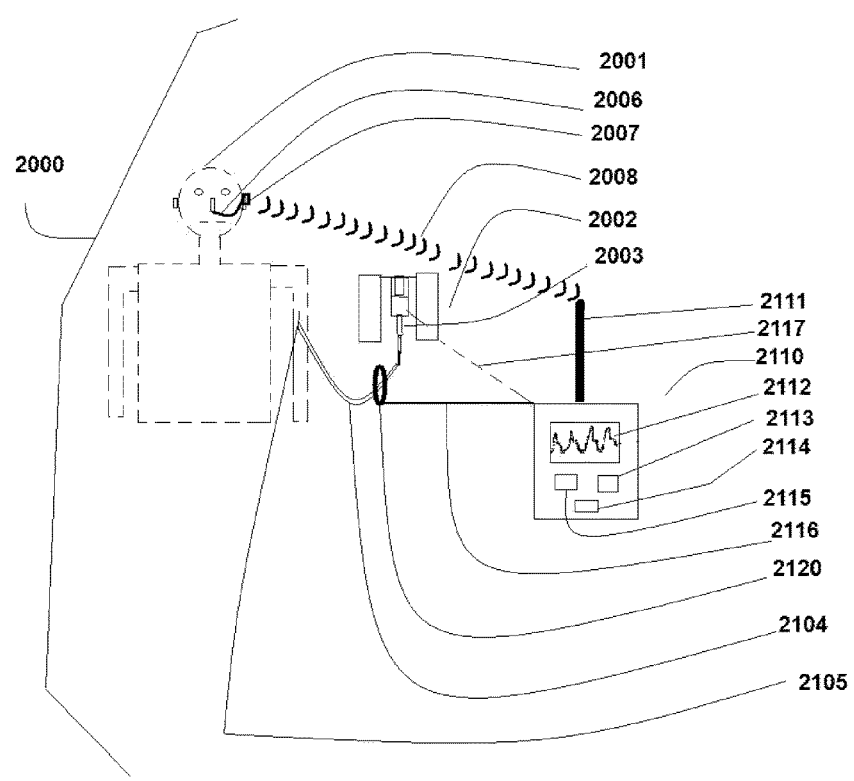
FIG. 9 provides an overall view of one embodiment of the monitoring system to improve infusion pump safety using, preferably, a single point of contact (SPOC) sensor and an infusion pump tubing occlusion device according to this invention.

This aspect of the patent disclosure provides the use of PPG and NAP/NAF along with an accelerometer to monitor the subtle cardiorespiratory changes that occur in the early stages of opioid induced respiratory depression (FIG. 9). When certain parameters are reached (e.g., increase in expiratory phase of respiration, slowing of the respiratory rate, decrease in movement, increasing respiratory effort indicating airway obstruction) a small device deployed on the IV tubing is mechanically, pneumatically or by like means, actuated to pinch the tubing shut. Simultaneously the monitor containing the software algorithms sounds an alarm. Depending on the particular infusion pump in use, this too, as a result, may sound an "occlusion" alarm.

According to one embodiment of this invention, complete occlusion of the IV tubing is preferred. However, in other embodiments, the tubing is only partially occluded to control the infusion rate and a closed-loop system deployable on any infusion device implemented according to this invention. In further embodiments according to this invention, the system described herein is incorporated into a module attached to an infusion pump, in which case the closed-loop system eliminates the need to occlude the IV tubing as the rate of infusion is, in that case, controlled directly by the infusion pump.

The key features of this aspect of the instant invention include: the use of PPG, other cardiorespiratory parameters and an accelerometer to monitor the pharmacodynamic (biological) effects of opioids (and other drugs) given IV (or via a non-IV route such as epidural or intrathecal routes, or the like) and to intervene before these changes lead to morbidity and mortality. Unlike the use of capnography to monitor end-tidal carbon dioxide and pulse oximetry to monitor oxygen saturation, the instant technology is not fraught with the problems of using those technologies in patients who are not in the ICU or OR settings, where capnography and pulse oximetry are practical and reliable, primarily because many ICU and OR patients are intubated (where it is easy to sample breath for an alveolar sample to determine $ET_{CO2}$) and are relatively still (and thus there is little motion occurring which could otherwise cause sensor artifact(s)).

By using the invention as herein described to measure the net pharmacodynamic effect of opioids and other medications, and thereby incorporating and integrating all the relevant factors (e.g., concomitant medications and disease states) that regulate the key biological effects of opioids and other medications, (including any possible cross-reactions between such medications), which in turn are direct determinants of patient morbidity and mortality, a highly reliable and reproducible means is provided to prevent opioid (and other medications) overdosing across all drug infusion platforms in a cost-effective manner.

Thus, while numerous means are known in the art for shutting off flow through infusion tubing, it will be appreciated by those skilled in the art upon reading this patent disclosure that it is preferable to have a device that shuts off flow by pinching the tubing compared to an in-line solution as there is virtually no chance of contaminating the system with an external shut off mechanism. Several examples of an appropriate shut-off valve for this purpose, according the present invention, are shown in FIG. 10 (A-C).

In light of the foregoing disclosure, it will be appreciated that a product according to the present invention, in one embodiment thereof, is a safety system designed especially for infusion pumps. In a preferred embodiment according to this invention, the system is so adapted and is so adaptable and, ideally, modular, that it can be used with any pump as interaction with the pump, while not excluded, is not required for the system to operate. Safety alarms in the pump system will alert appropriate personnel that the pump system requires attention. In any event, much better that the IV line, or the like, bursts, than that the subject continue to receive what has become a dangerous infusion of active agents. In any event, all pumps known in the market today include an occlusion sensor which sounds an alarm and shuts of the pump. In other words, the present system causes the pump occlusion sensor to operate by creating an occlusion.

It will further be appreciated that present technologies have been shown to be ineffective in detecting effects of opioids and other medications on the cardiorespiratory system. The instant invention will markedly improve the safety of infusion therapy and the system according to the present invention is applicable to pulse oximeters, capnography devices and the like, produced by Masimo, Nellcor, Philips, Oridion among others.

Referring now, in detail, to the elements of FIG. 9, there is shown the system 2000 according to this invention in place with a subject 2001 undergoing infusion via an infusion system 2002 of a medication 2003 via, in the embodiment shown in this figure, an intravenous tubing 2104 into a vein 2105 of the subject 2001. The subject 2001 is preferably fitted, per one embodiment according to the invention, with a Single Point of Contact (SPOC) probe 2006, which in the embodiment shown in this figure is a nasal alar probe, for acquisition of appropriate signals, as disclosed in the references referred to herein and which are herein incorporated by reference for this purpose. The SPOC probe 2006 includes a communication wire running to, and for being affixed to the head of the subject 2001, by any appropriate means, including, but not limited to, for example, an over ear retention system 2007, to which the which the communication wire from 2006 runs. In this embodiment, 2007 preferably also includes appropriate local electronics, including, but not necessarily limited to, an accelerometer, wired or wireless communications systems well known in the art. The probe 2006 preferably acquires signal from the nasal alae, or like SPOC position on the subject 2001, and relays such signals as are thus acquired to the over ear system 2007 for communication 2008 by that system to, either wirelessly for receipt by an antenna/receiver 2111, or via a wired connection, to an external system 2110. The external system 2110, is preferably a PPG monitoring system, able to extract from the signal 2008 received from the SPOC prove 2006 via the retention and communication system 2007, any desired signals for processing and analysis as herein described. The system 2110, for example, extracts heart rate 2113, respiratory rate 2114, and the subject's blood oxygen saturation level 2115. The external system 2110 is appropriately programmed and configured to develop from the signal 2108 acquired from the SPOC probe 2006 a series of Pharmacodynamic (PD) and/or Pharmacokinetic (PK) parameters are determined, (including, but not limited, for example, parameters discussed herein above, e.g. patient/subject position (in order to correct the PPG signal amplitude), via the accelerometer; Heart Rate Variability (HRV); measures of sympathovagal balance and input to the heart; heart rate and respiratory rate; autonomic nervous system function; other derived parameters, including but not limited to: Pulse Transit Time (PTT), Pulses Wave Velocity, Endothelial Dysfunction, Arterial Pressure Wave Shape and Amplitude, Ankle-Brachial index, Peripheral Artery Occlusion, Arrhythmias, NIBP (Noninvasive Blood Pressure); PPG and NAP/NAF).

Critically, for this invention, when certain pre-defined parameters are approached or reached (e.g., increase in expiratory phase of respiration, slowing of the respiratory rate, decrease in movement, increasing respiratory effort indicating airway obstruction) the system 2110 sends a signal via channel 2116 to a small device 2120 deployed on the IV tubing 2104. Depending on the nature of the signal conveyed via channel 2116 the device 2120 is mechanically, pneumatically or by like means, actuated to pinch the tubing, thereby occluding flow, either partially or completely.

Preferably, simultaneous or near simultaneous to the signal for occlusion being sent from device 2110 via channel 2116 to the device 2120, the monitor 2110 containing appropriate software algorithms for detecting approach to or arrival at a parameter defined for this purpose, sounds an alarm. Depending on the particular infusion pump in use, this too, as a result, may sound an "occlusion" alarm. In one preferred embodiment according to this invention, in addition to sending the signal via channel 2116 to the device 120 to occlude or partially occlude the tubing 2104, the system according to this invention also may be integrated with the pump system 2002 to send a signal to said pump system to either turn off or slow down its rate of medication delivery. This, of course, is only possible in the subset of instances where the external PPG monitor 2110 and the pump system 2002 "understand each other" by virtue of having compatible hardware, software, and signals between the two which permits this direct control of the pump 2002 via the PPG system 2110. As there already exist a large number of infusion pumps in use in a wide variety of medical care contexts, it would be a major undertaking to put in place appropriate external monitors, such as the PPG monitor 2110 according to this invention to achieve adequate and reliable communication with all the different varieties of such pumps 2002. It is largely for this reason that the present inventors have developed the present "agnostic" system, which permits the system according to this invention to be very quickly put into use in the field, in a wide variety of health-care contexts where such pumps are already in use, and to thereby provide an enhanced safety system by, on detection of an alarm condition, simply occluding or partially occluding the feed line 2104 from the pump to the subject 2001.

Figure 10A:
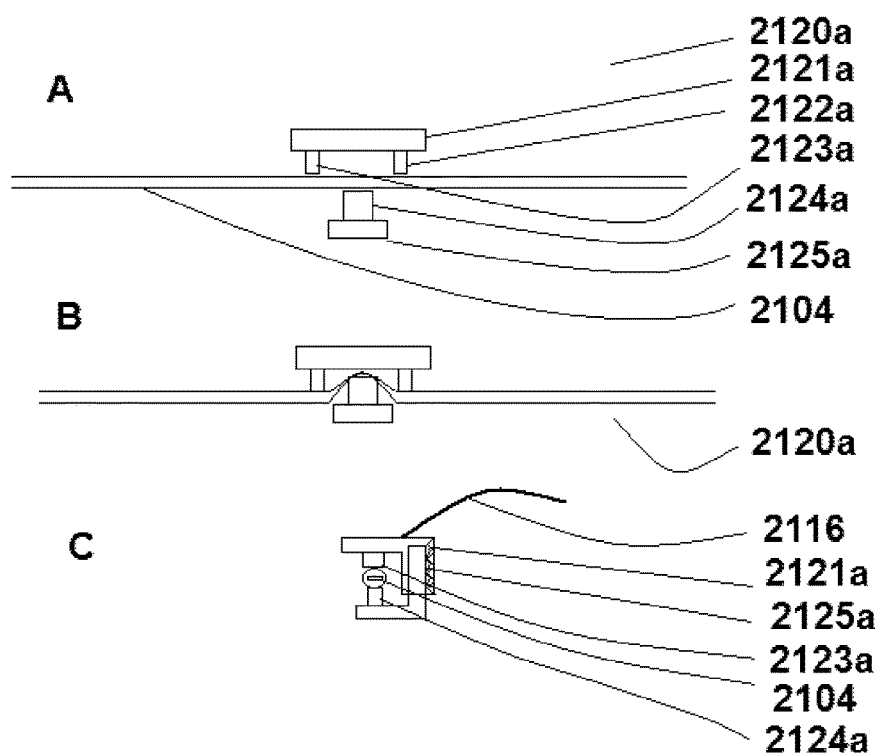
FIGS. 10A, 10B and 10C show different embodiments of the occlusion device according to this invention.

Referring now to FIG. 10, there are provided a series of alternate exemplary embodiments of the device, herein referred to as "the occlusion device", 2120 for use according to the system of this invention. In FIG. 10a, there is provided an occlusion device 2120a, comprising an upper occlusion member 2121a, and a lower occlusion member 2125a. The upper occlusion member 2121a comprises two tubing 2104 impingement members, 2122a and 2123a, and the lower occlusion member 2125a comprises a single tubing 2104 impingement member 2124a. In panel A of FIG. 10a, the occlusion device 2120a is shown in an open configuration, with the tubing 2104 running unimpeded between the occlusion members 2122a, 2123a and 2125a. In panel B, the same arrangement is shown with occlusion member 2125a impinging from below and occlusion members 2122a and 2123a impinging from above, thereby occluding the tubing 2104 as between these occlusion members. In panel C, there is shown a side view down the long axis of the tubing 2104, in the occluded state shown in panel B, with lumen of the tubing 2104 shown as being almost entirely occluded (i.e. the inner lumen of the tubing 2104 is not shown as a circular lumen but rather as a flattened lumen through which very little fluid may pass. This panel C view also shows the line 2116 through which the signal has been sent to occlusion device 2120a to actuate the impingement members 2122a, 2123a, and 2124a to be drawn close enough together to either completely or almost completely occlude the lumen of tubing 2104. Those skilled in the art are well aware of many different mechanical and/or pneumatic means for bringing these occlusion members into and to release these members from having been brought into sufficient proximity to each other to thereby occlude the tubing 2104. As an example, in this figure, it is shown that the rear element of upper occlusion member 2121a and the rear element of lower occlusion member 2125a are so arranged that the rear element of lower occlusion member 2125a rides within the rear element of upper occlusion member 2121a, and these elements are shown with intermeshed teeth, so that upon actuation, lower occlusion member 125a is drawn upward by intermeshment of the teeth on the rear of its member with the teeth provided for this purpose on the rear of upper occlusion member 2121a. Of course, in the event that any signal detected at controller 2110 no longer adheres, then these two members may, again, be actuated to spread apart, thereby once again opening the lumen of tubing 2104 to once again permit fluid to flow through the tube from the pump to the subject.

Figure 10B:
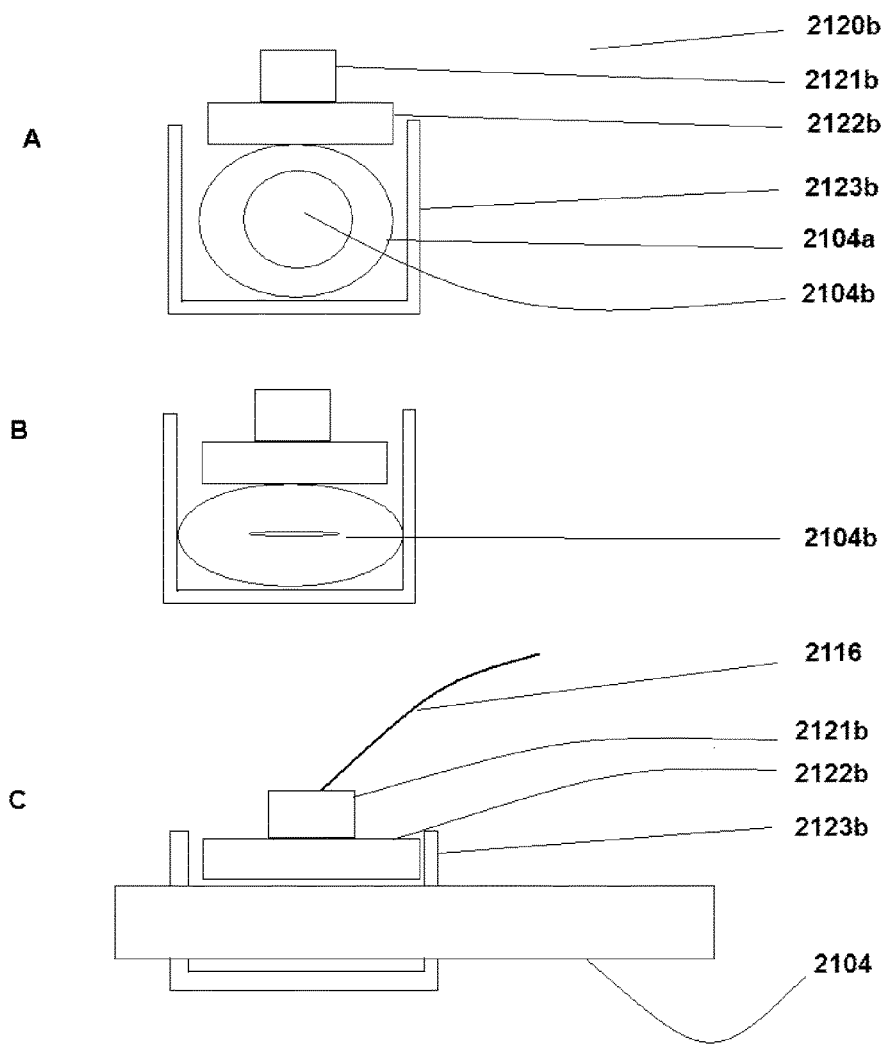

In FIG. 10b, there is provided another exemplary embodiment of the occlusion device 2120 according to this invention. In this embodiment, in panel A, there is shown a view down the long axis of the tubing 2104, housed inside an occlusion device 2120b according to this invention. Occlusion device 2120b comprises an upper occlusion member 2121b which is part of a pneumatic system (not shown, but such systems are well known in the art), whereby an upper impingement member 2122b is brought downward to impinge upon tubing 2104 which sits below the upper impingement member 2122b and is held in place by a lower containment vessel 2123b. In this figure, the lumen 2104b of the tubing 2104 can be seen to be wide open, thereby allowing fluid to pass through the lumen 2104b unimpeded.

In panel B of this figure, it can be seen that the upper impingement member 2122b has been pneumatically driven down upon the tubing 2104, thereby occluding the inner lumen 2104b to such an extent that little or no fluid may pass therethrough.

In panel C of this figure, there is shown a side view of the tubing 2104b which runs through occlusion device 2120b, such that upper occlusion member 2121b is actuated via an appropriate signal transmitted via communication channel 2116 to cause upper impingement member 2122b to be driven pneumatically to impinge upon the tubing 2104. In so doing, upper impingement member 2122b rides downward within containment chamber 2123b thereby squeezing the tubing 2104 and occluding its inner lumen 2104b as shown in panel B.

Figure 10C:
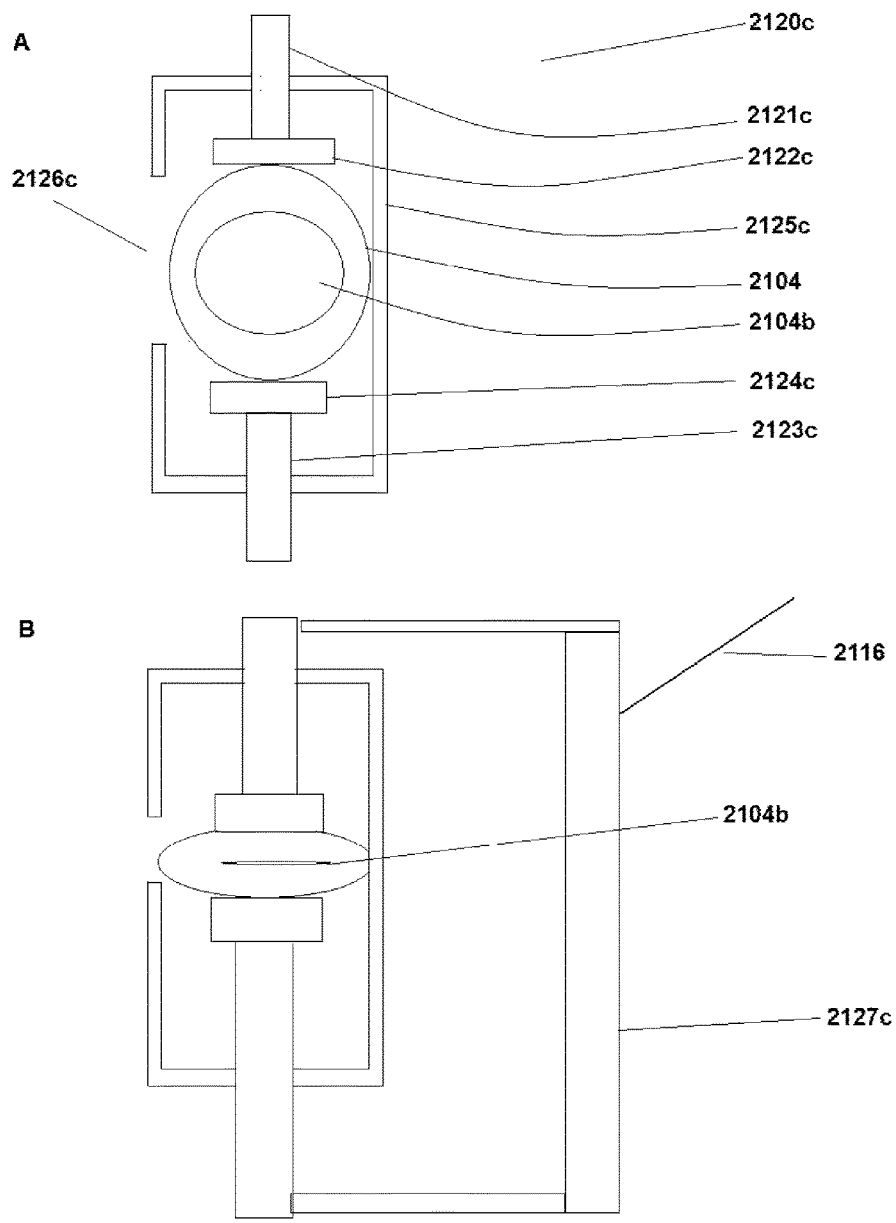

In FIG. 10c, in a further exemplary embodiment of the occlusion device 2120 according to the invention, there is provided an occlusion device 2120c, comprising upper and lower piston members 2121c and 2123c, each of which terminates with an impingement member 2122c and 2124c, respectively, which make contact with tubing 104 arranged there between. The tubing 2104, as well as upper and lower piston members 2121c and 123c are all housed in housing 2125c, which keeps the tubing 2104 in place and aligns pistons 2121c and 2123c. An opening 2126c is provided in the housing 2125c to facilitate introduction and removal of the tubing 2104 from the housing 2125c. In panel A, the tubing 2104 is shown un-occluded, while in panel B, the pistons 2121c and 2123c which are integral to a larger pneumatic actuation assembly 2127c, are shown in a position such that the tubing 2104 is occluded, such that its lumen 2104b is so narrow that essentially no fluid whatsoever may pass therethrough. As with the other embodiments of the occlusion device shown in FIGS. 10a and 10b, the signal for actuation of the pistons 2121c and 2123c is transmitted via communication channel 2116 from external control apparatus 2110.

Of course, it will be appreciated by those skilled in the art that, adopting this aspect of the present invention for use with any existing fluid line occlusion device, when integrated with appropriate physiological monitors according to the present disclosure, would come within the scope of the present invention. Thus, for example, utilizing the correct physiological monitors, as taught herein, the fluid constriction system disclosed in Weiner U.S. Pat. No. 6,165,151 and/or US2005/0027237, may be adapted for use to the present purposes, and those disclosures are herein incorporated by reference for this purpose. Likewise, for example, there is a Control Device and Process for a Pumping Device disclosed in U.S. Pat. No. 6,558,347 to Jhuboo et al., which permits an infusion tube to be blocked downstream of a pump may likewise be adapted for inclusion in the present system, while at the same time relieving the pump manufacturers of the required adaptations of their infusion devices that would otherwise be required to utilize the Jhuboo system. Furthermore, and also non-exclusively herein incorporated by reference for this purpose, there is disclosed by Mabry et al., in U.S. Pat. No. 7,661,440, a Device for Selectively Regulating the Flow Rate of a Fluid, which may likewise be adapted for inclusion in the present system, again without the need for integration to/with an existing fluid infusion system. Other fluid flow restrictors known in the art may likewise be utilized for this purpose when appropriately adapted for inclusion in the system of the present invention.

Scenario D: Enhanced Safety in Delivery of Medications which can or do Depress Respiration or Increase Respiratory Effort In situations where close monitoring of anesthetic agents, opioids or like compounds and combinations of compounds, is required, (which is always, of course, the case, but in certain contexts, particularly, for example, in the context of the need for maintaining minimal sedation e.g. for colonoscopies or esophagoduodenoscopy (EGD) procedures, it has been proposed that in the delivery of "conscious sedation" by non-anesthesiologists or in the delivery of opioids and other drugs that cause respiratory depression, often in combination e.g. opioids and benzodiazepines), especially during patient controlled analgesia (PCA) administration), whether trained anesthesiologists are present or not, the PPGcare™ system of this invention provides a critical safety system and advisory outputs, such that in the event of detecting respiratory depression, elevation in respiratory effort, elevation in blood $CO_2$, decrease in blood $O_2$, saturation, or any other indicator of hypoventilation, PPGcare™ optionally includes for such circumstances appropriate sensors and means for delivery of positive ventilation to maintain airway patency, means for reducing or terminating delivery of opioids or other medications, and alarms to alert appropriate professionals that the subject is in need of attention.

D.I. Summary of this Aspect of the Invention:

The system, apparatus and method of this invention comprises one, some, combinations of or all of the following features:

Improved monitoring including photoplethysmography (PPG) which provides accurate respiratory effort as well as respiratory rate;

Use of "nasal pillows" (commonly used with home CPAP [continuous positive airway pressure]) or the like means (tightly sealed masks and similar devices) to administer CPAP and other forms of "noninvasive positive pressure ventilation" and to accurately monitor end tidal carbon dioxide so that support can be provided to patients with diminished drive to breath spontaneously and/or who develop airway compromise. Capnometry, the means by which end tidal carbon dioxide is measured, has been shown to be unreliable in nonintubated patients: "The accuracy of the $ETCO_2$ (end tidal carbon dioxide) reading, however, cannot be relied upon because it has been shown to correlate with alveolar $ETCO_2$ only upon a full vital capacity breath, which rarely occurs in our setting. Thus, its value may lie in trend analysis." Overdyk F J, et. al. Anesth Analg 2007; 105:412-418. However, if CPAP is applied to patients, the airway is "stented" open and accurate end tidal carbon dioxide measurements are possible;

Novel nasal pillow designs for use in hospitalized patients and during conscious sedation;

Means to provide noninvasive ventilation (CPAP, BiPAP (Bilevel Positive Airway Pressure), adaptive servo-ventilation) when monitoring determines a patient is having increased effort to breath (via PPG) or reduced respiratory rate or respiratory drive;

Means to terminate or reduce the rate of administration of drugs that cause respiratory depression, including development of algorithms for closed loop medication administration, when monitoring according to this invention indicates such termination or reduction is called for based on increased respiratory effort or reduced respiratory rate or both;

For some applications, monitoring with an accelerometer to determine the activity status of a patient, such that the level of surveillance of the monitored parameters are reduced, for example, including reduced concern about movement and other artifacts that might otherwise trigger false alarms when the accelerometer indicates that the patient is active.

The system, apparatus and method according to this aspect of the invention comprises enhanced monitoring and means for "rescuing" patients using noninvasive ventilation so that conscious sedation and PCA delivery can be delivered safely. The system according to this aspect of the invention is also amenable for use to monitor and, where necessary, provide noninvasive ventilation and reduce medication delivery in any scenario where the level of care is less than that in an intensive care unit (ICU) or step-down unit, including: means (e.g. in the case of PCA and other drug infusions) for notifying healthcare or other workers that the patient requires immediate attention.

Accordingly, it is an object of this aspect of the invention to provide a comprehensive safety solution for conscious sedation, administration of opioid and other respiratory depression causing drugs.

It is a further object of this aspect of the invention to provide systems and methods for safe monitoring of patients receiving opioids and other medications that can induce respiratory depression throughout the hospital and during conscious sedation procedures in any medical environment.

A further object of this aspect of the invention is the production of a closed-loop system which includes algorithms to maintain adequate oxygenation/ventilation and for reducing the rate of delivery of opioid or other medications to maintain adequate analgesia while maintaining adequate cardiorespiratory parameters, to markedly improve patient safety and reduce the number of false alarms that cause healthcare workers to disable or ignore them. Alternatively, a "clinical advisor" system can be developed wherein a healthcare worker is notified and prompted to make appropriate changes. Thus, this is similar to a closed-loop system with algorithms analyzing the inputs from the patient and controlling the outputs from devices such as infusion pumps and non-invasive positive pressure ventilation, but rather than "closing the loop", it alerts a healthcare worker to make the appropriate changes.

A further object of this aspect of the invention is to provide a system and method to monitor for impending shock from almost any cause, including hypovolemia.

Further objects and advantages of this aspect of the present invention will be apparent to those skilled in the art from a review of the entire disclosure and the appended claims.

D.II. Detailed Description of this Aspect of the Invention

At least two clinical scenarios which leave patients at considerable risk of untoward events, including significant morbidity and death, have been repeatedly identified. These are: 1) the delivery of "conscious sedation" by non-anesthesiologists, and 2) the delivery of opioids and other drugs that cause respiratory depression, often in combination (e.g. opioids and benzodiazepines), especially during patient controlled analgesia (PCA) administration. Despite years of efforts to decrease untoward effects from these interventions, little has changed in terms of patient safety.

The first scenario occurs predominantly during endoscopy and other short procedures in the endoscopy suite, the Emergency Department or a physician's office. In order to perform endoscopy expeditiously and safely, it is generally important to have the patient relaxed and deeply sedated (as opposed to "conscious sedation") to prevent untoward complications such as perforation of the colon or unexpected movement during critical portions of a procedure. Unfortunately, the "lines" between conscious sedation, deep sedation and the early stage of general anesthesia are fine ones and reports of deaths and serious morbidity can occur when conscious sedation progresses to deep sedation/anesthesia, events that are, using currently available methods, not infrequent.

The medication of choice for conscious sedation is propofol (2,6-diisopropylphenol) because of its rapid onset and offset of action and favorable side effect profile. However, propofol is an anesthetic and has no analgesic properties. Therefore when used for conscious sedation, during painful portions of a procedure, the patient may be stimulated and start to move, causing the healthcare provider to administer more propofol which would take the patient to an unintended plane of deep sedation/anesthesia or worse add an opioid which would cause worsening respiratory depression.

One attempt to address the problems associated with conscious sedation is the SEDASYS® System marketed by JOHNSON & JOHNSON. Unfortunately, this system requires that the patient respond to auditory clicks and therefore does not allow a sufficiently deep level of sedation/ anesthesia to perform endoscopy and other procedures safely in many instances. This device has not been approved by the FDA for sale in the United States due to this and other limitations. Since many institutions require the presence of a trained anesthesia provider (e.g., anesthesiologist) to administer propofol, as it is considered an anesthetic, combinations of opioids and benzodiazepines are frequently used in lieu of propofol. The combination of an opioid and benzodiazepine requires just as much vigilance as does propofol, but physicians are allowed to administer this combination in the absence of an anesthesiologist. Unfortunately, since the SEDASYS® system is designed specifically for use with propofol, it does not provide a safety solution for use of the combination of opioids and benzodiazepines.

The absence of an anesthesiologist is particularly troubling as the most likely effect of propofol or opioid/analgesic dosing to achieve a level of deep sedation necessary to perform many procedures is respiratory depression. Neither SEDASYS® nor other systems described below provide any means to "rescue" a patient experiencing respiratory compromise. Further, with limited personnel and in the absence of an anesthesiologist, the ability to obtain and secure an adequate airway is severely compromised, placing patients in danger of morbidity and mortality.

Because of the limitations associated with known systems, as discussed above, there is a pressing need for a system that allows the safe administration of propofol, either alone or in combination with other medications, or for that matter the use of medication combinations excluding propofol, such as opioid plus benzodiazepine combinations.

In the second scenario, exemplified by PCA infusions, opioids alone, or in combination with other medications, are administered to patients in settings in the hospital where minimal to no monitoring is performed (it should be noted in this context that the SEDASYS® system provides significant vital signs monitoring capabilities—thus the irony of a greater level of monitoring in patients with a significant number of healthcare workers present verses a scenario where almost no monitoring is present and healthcare personnel are only remotely available).

PCA pumps allow patients to self-administer opioids at preset intervals and doses by pressing a button which provides feedback to the pump to administer the predetermined dose of medication. The problem with such a system is that it is extremely difficult to accurately assess the amount of opioid that is safe to administer to a specific patient, since opioids act on the brain to not only reduce the perception of pain, but to suppress the respiratory drive at centers in the brainstem. Individual sensitivity to opioids and other medications that can suppress respiratory drive can be due to concomitant administration of other medications (drug-drug interactions), differing rates of drug metabolism, age, physical condition and underlying diseases (obesity, cardiorespiratory disease, obstructive or central sleep apnea).

Presently, during conscious sedation, patients are monitored with ECG, blood pressure, pulse oximetry and a means to detect respiratory rate, such as capnography, which is unreliable for the detection of end tidal carbon dioxide in the absence of endotracheal intubation. In addition, patients are usually administered low flow oxygen, which negates the value of pulse oximetry as an early indicator of hypoventilation as detected by hypoxemia, thereby confounding the existing efforts to safely monitor patients undergoing conscious sedation.

Given all of these impediments to the safe delivery of opioids, propofol, benzodiazepines, and other medications, alone or in combination, while having to address the real need to provide adequate pain control or sedation to perform procedures safely, there is a pressing need for a new paradigm in patient monitoring and respiratory support.

The present disclosure addresses the above mentioned needs in the art by providing a system which includes means for securing accurate subject respiratory effort and respiratory rate combined with means for responding to dangerous depressions in such status. It is believed that the system, apparatus and method herein described provides a revolutionary improvement in patient monitoring and safety which meets the needs discussed herein.

In the description which follows, it will be understood that the term "nasal pillows" are soft, preferably resilient inserts for insertion into the nares so as to form a comfortable but tight seal. Materials including, but not limited to, cotton, wool, silicone, latex, foam, and the like may form the nasal insert portion of the "nasal pillows", in a fashion analogous to what is commonly utilized for in-ear headphones. For hospital applications, the nasal pillows are preferably built into a lightweight frame, similar to athletic glasses or the like, with an adjustable band for retaining the pillows in place by placing the band around the rear of the head of the subject, as in FIG. 26, with an adjustable fastening means at the back or at another appropriate location, to keep the frame properly positioned on the subject. For conscious sedation applications, nasal pillow headsets commonly used with CPAP systems can be used, as could tightly sealed masks, if applied immediately after sedation is commenced.

For conscious sedation, the system operates as follows:
1. Prior to administration of propofol or combination drugs to induce conscious sedation, monitors including, but not limited to, ECG and pulse oximetry (as part of PPG monitoring) are operatively attached to the subject;
2. The patient is fitted with a "nasal pillow" system incorporating PPG and capnography to facilitate monitoring at the nasal septum, nasal alae, or both, to acquire combinations of the following parameters: oxygen saturation, respiratory rate, respiratory effort, capnography, venous capacitance and a surrogate for cerebral blood flow determined from the AC component of the PPG or the raw PPG signal obtained from a nasal alae or septum, with additional parameters derived from the PPG and other measurements optionally also being collected, analyzed and displayed, as discussed herein above;
3. Once medication administration commences, a low level of CPAP sufficient to allow reliable end tidal carbon dioxide measurement is provided (in the range of 3-6 cmH$_2$O; adequate CPAP will be determined by analysis of the capnogram waveform), the system continuously monitors the subject for signs of respiratory depression, cardiorespiratory instability, or both, such that, should evidence of respiratory compromise be detected, the system automatically begins to titrate CPAP to maintain a patent airway and to improve oxygenation and gas exchange, with, optionally, alarms being set off to alert healthcare workers of early compromise and algorithms included in the system "advise" the proper action with prompts on the monitor screen;
4. If the addition of low levels of CPAP (<6 cmH$_2$O) corrects the respiratory compromise and the other monitored parameters remain stable, the procedure and administration of medications is permitted to continue;
5. If the addition of low level CPAP is inadequate to reverse the early signs of respiratory compromise, the system begins the administration of BiPAP or adaptive servo-ventilation;
6. Simultaneously, healthcare workers receive further prompts on proper intervention and the system automatically reduces the infusion rate or shuts off the infusion pump, depending on the degree of respiratory compromise.

For the administration of PCA or other infusions which could cause respiratory depression and airway compromise, the system operates as follows:
1. At the time of initiation of a PCA infusion, the patient is fitted with a "nasal pillow" system incorporating PPG and capnography to facilitate monitoring at the nasal septum, nasal alae, or both, to acquire combinations of the following parameters: oxygen saturation, respiratory rate, respiratory effort, capnography, venous capacitance and a surrogate for cerebral blood flow determined from the AC component of the PPG obtained from a nasal alae or septum, with additional parameters derived from the PPG and other measurements optionally also being collected, analyzed and displayed, as discussed herein above;
2. The nasal pillow system also incorporates or is operatively interfaced with an accelerometer or like motion sensing means for monitoring the level of activity of the subject, such that, as long as the subject is active, the system remains in a "surveillance" mode designed to markedly reduce the number of false alarms which lead to "alarm fatigue, but, when the patient is inactive, a "high alert" mode is initiated and the system monitors all parameters at a higher degree of scrutiny;
3. The system continues to monitor the subject, continuously or at a pre-set intermittent rate, and at the earliest signs of respiratory distress (airway obstruction/increased effort, hypoxemia, hypercapnia) the system initiates CPAP;
4. If low pressure CPAP corrects the problem, the system continues to monitor the patient, but if low pressure CPAP is inadequate to reverse the early symptoms of respiratory depression/airway obstruction, a higher level of CPAP or BiPAP/adaptive servo-ventilator, is initiated, healthcare workers are alerted, and the rate of infusion on the PCA pump is reduced or the infusion is terminated.

Figure 11:
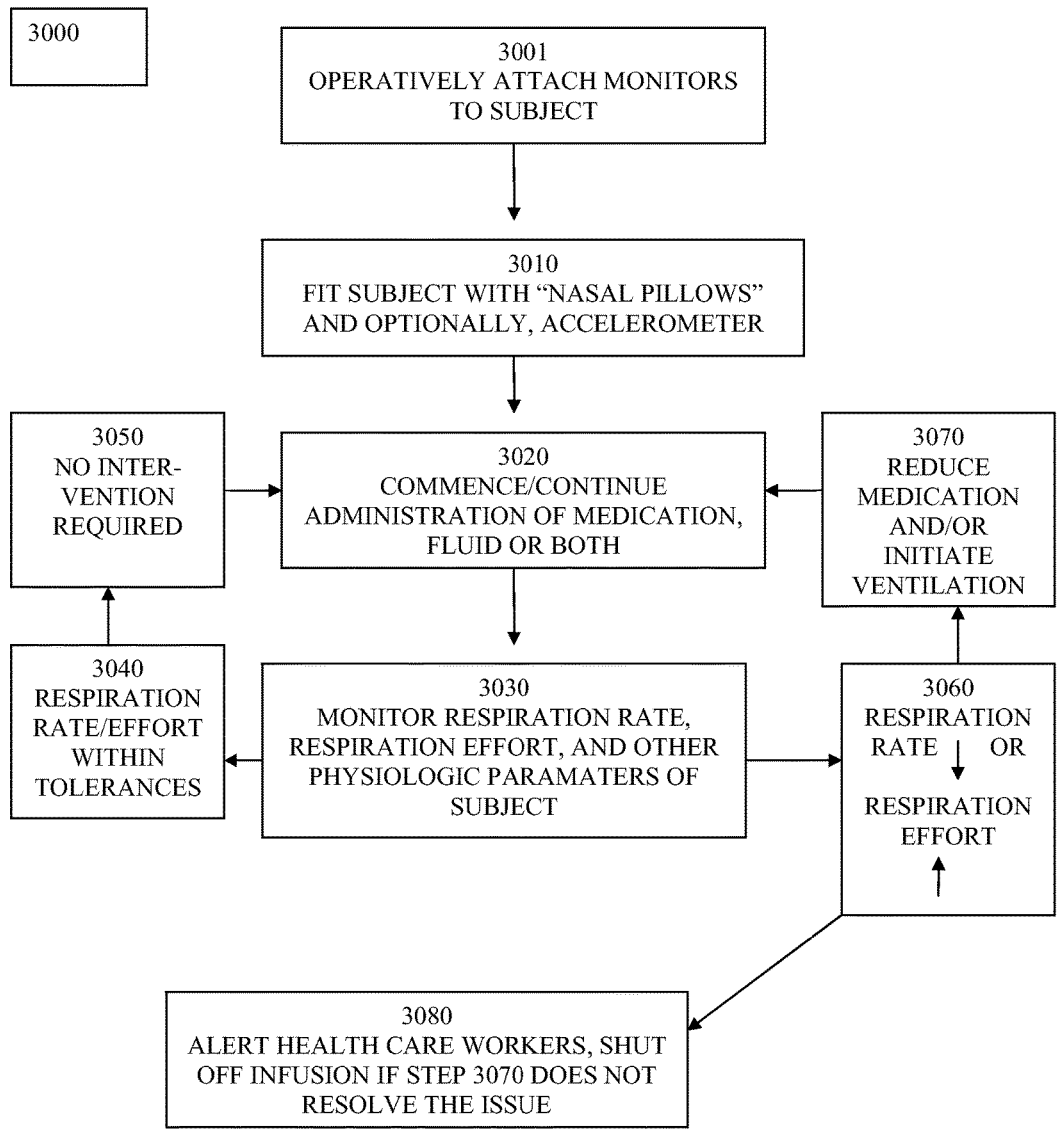
FIG. 11 is a flow-chart showing the steps of a method implemented according to the system or apparatus of the invention to monitor a subject's breathing rate, breathing effort or both (plus other parameters such as oxygen saturation, end tidal carbon dioxide, heart rate, etc.), and interventions automatically implemented on detection of reduced breathing rate, increased breathing effort or both.

FIG. 11 provides a flow-chart showing the steps of a method implemented according to the system or apparatus of the invention to monitor a subject's breathing rate, breathing effort or both (plus other parameters such as oxygen saturation, end tidal carbon dioxide, heart rate, etc.), and interventions automatically implemented on detection of reduced breathing rate, increased breathing effort or both.

Figure 12:
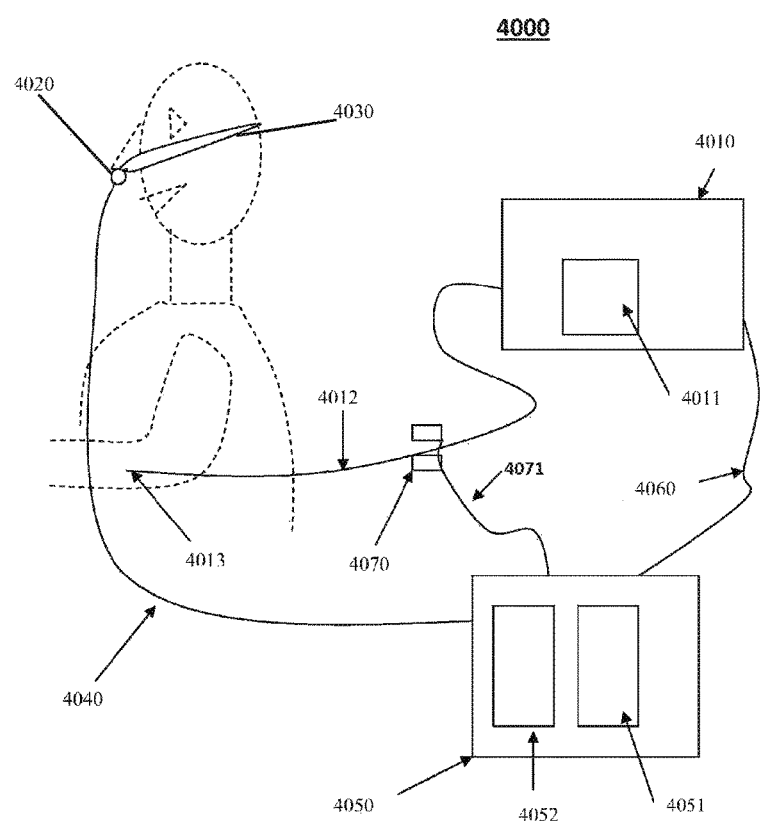
FIG. 12 provides a schematic representation of one embodiment of a system according to this invention for automatically providing ventilation to a subject on detection of reduced breathing rate, increased breathing effort or both, (plus other parameters such as oxygen saturation, end tidal carbon dioxide, heart rate, etc).

FIG. 12 provides a schematic representation of one embodiment of a system according to this invention for automatically providing ventilation to a subject on detection of reduced breathing rate, increased breathing effort or both, (plus other parameters such as oxygen saturation, end tidal carbon dioxide, heart rate, etc).

Referring in detail, now to the flow-chart shown in FIG. 11, which shows one embodiment of an algorithm 3000 for implementing this aspect of the invention as outlined above, it can be seen that appropriate monitors are attached to a subject at 3001. At a minimum, the appropriate monitors include affixation of a Central Source/Sensing Site (CSS) PPG monitor, preferably emplaced on the subject at the nasal alar region. In addition, of course, any or all sensors typically utilized for monitoring a subject may be included. Monitors utilized in conducting polysomnography (PSG) are known in the art and any or all of such sensors my be utilized. Those skilled in the art know that a polysomnogram (PSG) will typically record a minimum of twelve channels requiring a minimum of 22 wire attachments to the patient. So long as no contradictory information is received from any or all of these additional monitors, the CSS PPG signal disclosed in detail in this patent disclosure may be utilized as a primary control signal to initiate, terminate, increase or decrease infusion of a medication, provided an appropriate physiologic parameter obtainable from the PPG signal indicates that a critical monitored parameter, e.g. hypoventilation, hypovolemia and the like calls for such intervention.

To ensure that those skilled in the art reading this patent disclosure are aware of the additional monitoring that may be conducted, in combination with the CSS PPG monitoring, and which may be included in a given implementation of the PPGcare™ technology disclosed herein, it will be appreciated that the PSG channels vary in every lab and may be adapted to meet the needs of the trained personnel or subject for the given medical procedure. In standard PSG, there is a minimum of three channels for the EEG, one or two measure airflow, one or two are for chin muscle tone, one or more for leg movements, two for eye movements (EGG), one or two for heart rate and rhythm, one for oxygen saturation and one each for the belts which measure chest wall movement and upper abdominal wall movement. The movement of the belts is typically measured with piezoelectric sensors or respiratory inductance plethysmography. This movement is equated to effort and produces a low-frequency sinusoidal waveform as the patient inhales and exhales. Because movement is equated to effort, this system of measurement can produce false positives. It is possible, especially during obstructive apneas, for effort to be made without measurable movement. PPGcare™ addresses this limitation by acquiring respiration signals from the CSS as disclosed herein. Wires for each channel of recorded data lead from the patient and converge into a central box, which in turn is connected to a computer system for recording, storing and displaying the data, and in the case of a PPGcare™ system, for control of infusion of medication and/or fluid.

PSG, when used during sleep, includes a computer monitor which can display multiple channels continuously. In addition, most labs have a small video camera in the room so the technician can observe the patient visually from an adjacent room. The electroencephalogram (EEG) will generally use six "exploring" electrodes and two "reference" electrodes, unless a seizure disorder is suspected, in which case more electrodes will be applied to document the appearance of seizure activity. The exploring electrodes are usually attached to the scalp near the frontal, central (top) and occipital (back) portions of the brain via a paste that will conduct electrical signals originating from the neurons of the cortex. These electrodes will provide a readout of the brain activity that can be "scored" into different stages of sleep (N1, N2, N3 which combined are referred to as NREM sleep, and Stage R which is rapid eye movement sleep or REM, and Wakefulness). The EEG electrodes are placed according to the International 10-20 system. The electrooculogram (EGG) uses two electrodes; one that is placed 1 cm above the outer canthus of the right eye and one that is placed 1 cm below the outer canthus of the left eye. These electrodes pick up the activity of the eyes in virtue of the electropotential difference between the cornea and the retina (the cornea is positively charged relative to the retina). This helps to determine when REM sleep occurs, of which rapid eye movements are characteristic, and also essentially aids in determining when sleep occurs. The electromyogram (EMG) typically uses four electrodes to measure muscle tension in the body as well as to monitor for an excessive amount of leg movements during sleep (which may be indicative of periodic limb movement disorder, PLMD). Two leads are placed on the chin with one above the jaw line and one below. This, like the EOG, helps determine when sleep occurs as well as REM sleep. Sleep generally includes relaxation and so a marked decrease in muscle tension occurs. A further decrease in skeletal muscle tension occurs in REM sleep. A person becomes partially paralyzed to make acting out of dreams impossible, although people that do not have this paralysis can suffer from REM behavior disorder. Finally, two more leads are placed on the anterior tibialis of each leg to measure leg movements. Though a typical electrocardiogram (ECG or EKG) would use ten electrodes, only two or three are used for a polysomnogram. They can either be placed under the collar bone on each side of the chest, or one under the collar bone and the other six inches above the waist on either side of the body. These electrodes measure the electrical activity of the heart as it contracts and expands, recording such features as the "P" wave, "QRS" complex, and "T" wave. These can be analyzed for any abnormalities that might be indicative of an underlying heart pathology. Nasal and oral airflow can be measured using pressure transducers, and/or a thermocouple, fitted in or near the nostrils; the pressure transducer is considered the more sensitive. This allows the clinician/researcher to measure the rate of respiration and identify interruptions in breathing. Respiratory effort is also measured in concert with nasal/oral airflow by the use of belts. These belts expand and contract upon breathing effort. However, this method of respiration may also produce false positives. Some patients will open and close their mouth while obstructive apneas occur. This forces air in and out of the mouth while no air enters the airway and lungs. Thus, the pressure transducer and thermocouple will detect this diminished airflow and the respiratory event may be falsely identified as a hypopnea, or a period of reduced airflow, instead of an obstructive apnea. Pulse oximetry determines changes in blood oxygen levels that often occur with sleep apnea and other respiratory problems. The pulse oximeter fits over a finger tip or an ear lobe. Snoring may be recorded with a sound probe over the neck, though more commonly the sleep technician will just note snoring as "mild", "moderate" or "loud" or give a numerical estimate on a scale of 1 to 10. Also, snoring indicates airflow and can be used during hypopneas to determine whether the hypopnea may be an obstructive apnea.

Once the monitors, including the CCS PPG monitor, are operatively in place on the subject, in a preferred embodiment according to this invention, the subject is also fitted with "nasal pillows" as described herein, and, optionally, an accelerometer or like device which can record movements of the subject 3010. At this point, administration of medication, fluid or both can be initiated or continued 3020. The subject's respiration rate, effort and other physiologic parameters are monitored 3030, and so long a these parameters remain within pre-programmed tolerances 3040 the medical procedure and infusion is permitted to proceed without intervention 3050. However, on detection of a respiration rate drop or a breathing effort increase, or other adverse indicia of subject physiologic condition, 3060, positive pressure ventilation may immediately be initiated and, if necessary, the delivery of medication can be reduced or terminated 3070. Once the adverse condition is resolved, medication/fluid infusion may be continued 3020, and ventilation can be continued or terminated as indicated by the respiration rate signals derived from the CSS PPG monitoring.

Referring now in detail to FIG. 12, there is shown a PPGcare™ system and apparatus 4000 in which there is provided an infusion pump 4010 comprising a source of fluid, medication or both 4011. The pump 4010 infuses the medication/fluid 4011 into a subject (shown in outline) via an infusion line 4012 and into, for example, the arm of the subject 4013. Operatively adhered to the subject is a CSS monitor 4020 which preferably also comprises means for delivery of gas and for measuring expired gas, (e.g. for ETCO2), as described in further detail, for example, in relation to the device shown in FIG. 26. Line 4040 comprises a plurality of separate leads and hoses, including power leads to power the CSS PPGcare™ monitor at the subject's nasal alae. It also comprises a hose for delivery of positive pressure ventilation where such intervention is initiated by detection of hypoventilation as described herein. Line 4040 also comprises signal carrying lines (or if the CSS PPG unit adhered to the subject has wireless transmission capabilities, such wired communication lines may not be required), to carry the acquired signal back to the control unit 4050. The control unit 4050 is operatively connected via lead 4060 to the infusion pump for control thereof to initiate, terminate, increase or decrease infusion, based on signals acquired from the subject, including from the CSS PPG monitor. If, however, the pump 4010 and the controller 4050 do not have compatible communication protocols, the control unit 4050 can, in any event, control infusion to the subject via the pump agnostic occluder, 4070, which, based on status of the subject, may be activated to occlude or de-occlude the line 4012 carrying infusate to the subject. Control unit 4050 comprises or controls a separate source of gas 4051 for providing positive pressure ventilation to the subject when this is determined to be required by a processor unit 4052 which is pre-programmed to process the signal from the CSS PPG sensor, and any other subject associated monitors. On determining that the subject is hypoventilating, the controller 4052 initiates the routine shown in FIG. 11. Because the CSS PPG monitor at the subject is acquiring signal from which evidence of hypoventilation is derivable, it is preferred to have the subject spontaneously breathing, without supplemental oxygen, for as much of the procedure as possible. In this manner, a PSS monitor, e.g. a PPG monitor and/or pulse oximeter, can acquire information relating to blood oxygen saturation levels, and this can provide separate information indicating desaturation or hypoventilation. If the subject is at all times being flushed with supplemental oxygen, however, then the value of the pulse oximetry signal is diminished. The CSS PPG signal, however, operates reliably, whether or not oxygen or other supplemental or positive pressure ventilation has been initiated.

EXAMPLES

While the foregoing disclosure generally describes this invention, the following examples are provided to further describe and enable this invention. It will be appreciated, however, that these examples and the specifics provided therein are non-limiting and those skilled in the art could vary or use equivalent methods, apparatuses and systems, without departing from the heart of the invention.

Example 1

In subjects receiving prescriptions for opioids and/or combinations of opioids with other medications, either prescribed or taken against medical advice (e.g. ethanol), which increase the potential for drug overdose/respiratory depression/arrhythmias (oxycodone, fentanyl TD, morphine ER, oxycontin, dextromethorphan in combination with others) for home use, adherence and well being are monitored using a cardiorespiratory-based PD sensor according to the invention.

For oral medication(s), the patient is provided with a small microprocessor/microcomputer that is worn on the belt (or over the ear similar to a hearing aid) and attaches (either directly or by communications such as Bluetooth) to a small sensor array which is attached at a single point of contact (SPOC) to one nasal ala. The SPOC array consists of one or more of the following: an extremely small pulse oximeter sensor (photodiodes [one or more LEDs] and a photodetector), a nasal pressure sensor, one of at least two ECG leads, a nasal flow sensor (thermistor or other). The SPOC is light weight and barely visible.

The SPOC array continuously monitors cardiorespiratory parameters such as ECG, SpO2, photoplethysmography (PPG) (from which respiratory rate, respiratory effort, arterial blood flow, venous capacitance and other parameters are derived), nasal pressure or flow (as a watchdog function for respiratory parameters derived from the PPG). The SPOC system optionally also includes an accelerometer to monitor the position of the patient.

When the patient is upright and moving, the microprocessor goes into a standby or sleep mode where it uses low power to monitor the accelerometer. If the patient reclines or motion decreases markedly, the microprocessor wakes-up and continuously monitors the patient.

The changes in brainstem function associated with respiratory depression from opioids are well documented. The association with multiple drugs and various disease states is more complicated, but since SPOC provides the microprocessor with a variety of physiologic signals, the algorithms access the combined effects of clinical interventions and a patient's underlying clinical condition on the cardiorespiratory systems.

In the instance where a patient begins to have diminished cognitive and/or brainstem function, the microprocessor determines, from the SPOC derived parameters that the patient is beginning to have diminished responsiveness based on the characteristic changes. These are seen in the respiratory pattern, rate and depth of breathing as well as in the cardiac system, where loss of pulse rate variability is often seen. Additionally, the accelerometer determines that the patient's activity has decreased substantially, indicating that the patient is sleeping and/or suffering the effects of brainstem depression. Algorithms based on SPOC derived data determine the differences between normal sleep and respiratory/cerebral depression.

When the microprocessor determines the decreased activity and/or the SPOC derived parameters indicate respiratory depression, an alert function, such as alarms, and messages sent to care givers, family members and healthcare professional including EMS, are activated. This alert can be sent by conventional telephone modem, wirelessly, by cable or other means (such as satellite) to provide the necessary support for the patient.

Example 2

Optimal sedation in patients undergoing colonoscopies using a combined PK (e.g. using breath analysis used to measure blood levels of propofol)-, and PD (e.g., using cardiorespiratory-derived parameters from PPG)-based system to control of an infuser device is used to safely deliver IV propofol. A PK+PD-based propofol infusion system that provides drug effects on respiratory and cardiovascular systems is therefore enabled and is easily implemented by those skilled in the art in light of the teachings provided herein.

In the case of propofol, it would be ideal to have a drug delivery system that would guide intravenous (IV) infusion rates based on a closed loop or "advisory" control system using both PK (relationship between propofol dose and propofol blood concentration) and PD (relationship between propofol blood concentration and biological response, namely effects of propofol on cardiorespiratory function predominantly via biological effects of propofol on the brainstem) inputs. When a drug such as propofol is given IV, the relationship between dose and pharmacological effect is interspersed by two important factors: PK (dose-concentration relationship) and PD (concentration-response relationship). In general, for most IV drugs, it appears that the variability between dose and pharmacological effect is approximately due to equal contributions from variabilities in PK and PD. However, this contribution can vary by drug (see below for propofol, where PK variability appears more important than PD variability). In general for controlling IV drug infusions, irrespective of PK versus PD contributions to variabilities in dose-response, it is preferable to guide drug dosing based on the biological effects of the drug, because it takes into account the multitude of factors that can alter PK and/or PD, and integrates them at the level of biological responsiveness, which in turn controls drug infusion rates, either in a closed loop (machine outputs automatically modifies drug infusion rates) or open loop (human takes system output and modifies drug infusion rate) configuration. In the case of propofol, during sedation (e.g., Levels 1 and 2) where the subjects are breathing spontaneously, the cardiorespiratory effects of propofol at various levels of anesthesia are well known, and SPOC-derived parameters (see Example 1) are well suited to guide drug infusion rates. In the current invention, the PK and PD information provided by the end tidal propofol breath and SPOC sensor, respectively, is complementary and allows optimal management of patients over a wide range of sedation depths (Level 1: minimal sedation; Level 2: moderate sedation; Level 3: deep sedation, and Level 4: general anesthesia). In other words, by knowing the blood levels of propofol in conjunction with key biological effects of propofol on cardiorespiratory function, key information such as the relative contributions of PK versus PD to the overall biological effect of this widely used IV anesthetic can be readily determined. In addition, other key safety information such as rapid detection of intravenous catheter infiltration delivering the propofol can be rapidly detected and corrected. In this case, with IV infiltration the anesthesia provider would observe rapid and marked reductions in breath propofol, indicating rapid and marked reductions in blood propofol levels, even prior to seeing a change in PD parameters (propofol washout in brain tissue is slower than that in the blood). Under these circumstances, the clinician would have time to correct the situation prior to the patient inadvertently emerging during the surgical procedure, and thus preventing intraoperative recall and even more serious sequelae such as PTSD. Likewise, during deeper levels of sedation (level 3) or general anesthesia (level 4), because the patient may and will need help, respectively, with their breathing, it will become problematic to measure end tidal breath values of propofol (unless intubated). In contrast, the SPOC sensor should continue to function. Taken together, the employment of a propofol breath sensor along with SPOC sensor allows optimal management of patients receiving propofol in a wide variety of clinical scenarios. Moreover, in this scenario, using PK (to determine blood levels of propofol using breath measurements) as well as PD, becomes important, because the anesthesia provider can use blood levels as an index of anesthetic depth in a given patient, particularly when they trend the blood levels of propofol with PD parameters. In this manner, PD and/or PK parameters are highly complementary management tools to guide drug infusion rates and to optimize drug safety and efficacy in most clinical scenarios that employ the use of propofol. The measurement of propofol levels in breath to estimate blood levels is an extension of what anesthesia providers currently use for volatile anesthetics (e.g., desflurane, isoflurane, sevoflurane, etc).

In this embodiment, it is technologically feasible to use breath levels of propofol to determine propofol PK in humans. Specifically, several independent groups around the world have conclusively demonstrated that propofol (the parent molecule that causes anesthesia, not a metabolite) appears in the exhaled breath of humans and that exhaled concentrations of propofol correlate to those found in the serum. The following table summarizes these findings:

| Instrument Used to Measure Breath Propofol | Correlation Coefficient (r2) | References |
| --- | --- | --- |
| SAW | N/A | Melker, R J et al, USPTO 7,104,963). Sep. 12, 2006. |
| PTR-MS | N/A | Harrison G R et al, Real-time breath monitoring of propofol and its volatile metabolites during surgery using a novel mass spectrometric technique: a feasibility study. Br. J. Anaesth. 2003; 91: 797-9 |
| IMR-MS | 0.85-0.96 | Hornuss C et al, Real-time monitoring of propofol in expired air in humans undergoing total intravenous anesthesia. Anesthesiology 2007; 106: 665-74 |
| PTR-MS | "High" | Takita A et al, On-line monitoring of end-tidal propofol concentration in anesthetized patients. Anesthesiology 2007; 106: 659-64 |
| HS-SPME-GC-MS | 0.85 | Miekisch W et al, Assessment of propofol concentrations in human breath and blood by means of HS-SPME-GC-MS. Clin. Chim. Acta 2008; 395: 32-7 |
| MCC-IMS | 0.73 | Perl T et al, Determination of serum propofol concentrations by breath analysis using ion mobility spectrometry. Br. J. Anaesth. 2009; 103: 822-7 |
| HS-SPME-GC-MS | 0.83 | Gong Y et al, Investigation of Propofol Concentrations in Human Breath by Solid-phase Microextraction Gas Chromatography-Mass Spectrometry. J. Int. Med. res. 2009; 37: 1465-71 |

Abbreviation Key: Although this table includes only human data, a large amount of non-human data also confirms this relationship. Abbreviations: SAW; surface acoustic wave; PTR-MS, proton transfer reaction-mass spectroscopy; IMR-MS, ion-molecule reactions coupled with quadrupole mass spectrometry; HS-SPME-GC-MS, headspace solid-phase microextraction gas chromatography-mass spectrometry; MCC-IMS, mobility spectrometer coupled to a multicapillary column for pre-separation.

Propofol: Importance of PK Versus PD in Drug Response:

The biological effect of every drug is influenced by variability in PK (relationship between dose and concentration) and PD (relationship between concentration and effect). The relative contribution of PK and PD variability of propofol on clinically determined end-points has been studied (Minto et al, Using the time of maximum effect site concentration to combine pharmacokinetics and pharmacodynamics. Anesthesiology. 2003; 99: 324-33). The concentrations of drugs can be used to determine (or at least estimate) the effects of drugs such as isoflurane, valproic acid, vancomycin, gentamycin, cyclosporine, and others. Although the exact nature of the relative contributions of PK and PD are not well specified for most agents that undergo therapeutic drug monitoring, many clinicians still measure (and insurance companies pay for) their concentrations and integrate this data into overall patient care. However, perhaps the best example of drugs where blood (and breath) concentrations can be readily used to determine biological effects is volatile anesthetics in the anesthetic arena. For example, similar to minimum alveolar concentration (MAC) values for volatile anesthetics currently measured in the OR such as sevoflurane, propofol demonstrates a concentration-response curve to cause various biological effects. Although reproduced many times, the original work of Schafer and colleagues from the 1980s demonstrates the relationship between propofol concentration and unconsciousness in human surgical patients (Shafer A et al, Pharmacokinetics and pharmacodynamics of propofol infusions during general anesthesia. Anesthesiology. 1988; 69: 348-56). The EC50 values for awakening and orientation were remarkably similar (1.07±0.13 and 0.95±0.19 µg/ml, respectively), and were independent of patient age, sex, weight, liver function test results, or type of surgery (Shafer A et al, Anesthesiology, 1988; 69: 348-56). Awakening and orientation are important values to anesthesiologists in order to facilitate operating room turnover and efficiency.

Moreover, the blood concentration of propofol was used by several groups to demonstrate that BIS actually measures anesthetic depth. That is, propofol concentrations were used as the "gold standard" of anesthetic depth when developing the bispectral index (BIS) monitoring system. In these studies of human surgical patients, the blood concentration of propofol was compared to the BIS value at various planes of anesthesia measured by many sedation scores (Iselin-Chaves I A et al, Changes in the auditory evoked potentials and the bispectral index following propofol or propofol and alfentanil. Anesthesiology. 2000; 92: 1300-10; Doi M et al, Relationship between calculated blood concentration of propofol and electrophysiological variables during emergence from anaesthesia: comparison of bispectral index, spectral edge frequency, median frequency and auditory evoked potential index. Br. J. Anaesth. 1997; 78: 180-4). Clearly, propofol concentrations correspond to anesthetic depth as determined not only by clinical endpoints, but also by BIS measurement. Taken together, these results collectively indicate that variability in PK is a more important predictor of changes in the biological effects of propofol than variability in PD (i.e., blood levels of propofol in humans reliably translate to predictable anesthetic responses whereas doses of propofol do not reliably translate to predictable blood levels of propofol). This finding is consistent with the failure of a targeted control infusion (TCI) system for propofol (Diprifusor™), which was designed to give predictable blood levels based on population PK parameters, to function well clinically (Frölich M A et al, Precision and bias of target controlled propofol infusion for sedation. Br. J. Anaesth. 2005; 94:434-7). 12 In other words, due to variability in PK parameters among humans, the TCI systems did not accurately predict blood levels of propofol in humans, because it is based on global PK parameters. Therefore, by removing PK variability "out of the equation", a system that measures breath propofol (and hence blood levels) would accurately assess the PD (anesthetic effects) of this important and widely used IV anesthetic, and thus be valuable in the management of patients undergoing propofol anesthesia.

Embodiment of Close Loop Propofol System in Example 2:

In the setting of sedation using propofol, the patient is provided with a small sensor array which is attached at a single point of contact (SPOC) to one nasal ala and a custom designed breath mask (or nasal pillows) to allow breath levels of propofol to be determined. A small microprocessor/microcomputer is placed near the head of the patient, either attached to the OR table/stretcher or a nearby IV pole. Communications between the SPOC and microprocessor will be via a direct connection or by wireless communications such as Bluetooth. The SPOC array consists of one or more of the following: a small pulse oximeter sensor (photodiodes [one or more LEDs] and a photodetector), a nasal pressure sensor, one of at least two ECG leads in the SPOC (or interfaced to ECG leads used by the conventional anesthesia monitoring system), a nasal flow sensor (thermistor or other). The SPOC is light weight. The breath levels of propofol will be measured using a sensor including but not limited to a surface acoustic waveform (SAW) technology, via either a side-stream analyzer or an in-line system attached to the breath mask. Measurements of the propofol will be gated to obtain end tidal samples according to the phase of ventilation using various respiratory parameters including but not limited to ETCO2, temperature, humidity and pressure. The SAW sensor output will be integrated into the SPOC-microprocessor system (either wirelessly or via direct connection) to provide near real-time measurements of propofol blood levels (via the SAW sensor) and the biological effects (via the SPOC system) of propofol. A weighted numerical scoring system, which takes into account the various PK and PD parameters, will be one method that is devised to control propofol infusion rates. Obviously, when apnea occurs, the propofol infusion will be guided by PK, whereas at lower levels of propofol anesthesia depth where spontaneous ventilation is present, PD will have a more important role. When the microprocessor determines the decreased activity and/or the SPOC derived parameters indicate respiratory depression, an alert function, such as alarms, and messages will be sent to the anesthesia provider as the system simultaneously modifies the infusion rate of propofol.

The SPOC array continuously monitors cardiorespiratory parameters such as ECG, SpO2, photoplethysmography (PPG) (from which respiratory rate, respiratory effort, arterial blood flow, venous capacitance and other parameters are derived), nasal pressure or flow (as a watchdog function for respiratory parameters derived from the PPG). The SPOC system optionally also includes an accelerometer to monitor the position of the patient during sedation and general anesthesia. When the patient is moving, the microprocessor notifies the anesthesia provider.

In summary, the cardiorespiratory changes caused by different concentrations of propofol on the cardiorespiratory centers of the brainstem are well documented. Because propofol has variable PK between humans and its PD effects can be markedly augmented by many factors including disease or the presence of other drugs (e.g., benzodiazepines, opioids), the use of SPOC to measure biological effects of propofol is desirable, because it takes into account and integrate all these factors at the level of propofol's effects on the cardiorespiratory systems. For example, if the anesthesia provider solely used propofol blood levels alone to guide propofol dosing, he/she may well overdose the patient, if midazolam (a benzodiazepine) and/or fentanyl (a potent narcotic) were administered, because they sensitive the brainstem to the respiratory effects of propofol but do not change the blood levels of this widely used IV anesthetic.

Example 3

Alcohol (e.g. ethanol) is detected (important during titration as well as chronic use) on breath during adherence testing for oxycontin. Subjects may be randomly called and requested to emplace the PD system on their nose, and/or to test for adherence, and/or to test for the presence of alcohol blood levels. A system used to monitor adherence to and/or to prevent diversion of oxycontin as well as automatically detect blood levels of ethanol (using breath) is incorporated into a PD-based system to measure the biological effect of oxycontin and any significant interaction with ethanol on cardiorespiratory function.

The diversion of prescription opioids for non-medical use is a national epidemic. In 2008 2.2 million Americans initiated nonmedical use of prescription opioids, and 1.24 million met DSM-IV criteria for opioid addiction (Substance Abuse and Mental Health Services Administration. (2009). Results from the 2008 National Survey on Drug Use and Health: National Findings (Office of Applied Studies, NSDUH Series H-36, HHS Publication No. SMA 09-4434). Rockville, Md. Available at: http://www.oas.samhsa.gov/NSDUH/2K8NSDUH/tabs/Sect5peTab14.pdf). Unfortunately, opioids frequently cause mortality, because it suffers from a major PD interaction with ethanol. Specifically, ethanol markedly sensitizes the cardiorespiratory centers of the brainstem to the depressant effects of opioids, frequently leading to apnea and death. This problem is not limited to opioids. There are at least 220 US approved drugs where specific warnings against ethanol intake are listed in the label. The potentially lethal interaction of ethanol with many drugs occurs almost exclusively at two levels: 1) PK: ethanol levels alter blood levels of active drug (e.g., abacavir), and/or 2) PD: ethanol alters the biological target sensitivity to the active drug but does not alter blood levels (e.g., opioid: Oxycontin [oxycodone]; benzodiazepine: Xanax [alprazolam]). Most significant interactions with ethanol occur with the latter mechanism.

In this embodiment, we (our patent references) are developing medication adherence systems that can monitor narcotic (opioid) adherence and prevent opioid diversion by analyzing "breathprints" of generally recognized as grass (GRAS) compounds, which are FDA approved compounds for use in foods (additives or natural). The sensor used to detect these unique chemical patterns in the breath, termed a miniature gas chromatograph-metallic oxide sensor (mGC-MOS), not only detects adherence to drugs, but also can be used to sensitively and specifically detect and quantitate ethanol in blood, even at very low concentrations. Thus, the use of the mGC-MOS has a dual benefit in this clinical scenario: 1) monitor adherence to opioids and prevent diversion, and 2) make opioid treatment safer, because it can be used to avoid the many PK and/or PD interactions with ethanol. This embodiment (assessing medication adherence along with regular or intermittent checks on blood ethanol levels using the breath) highlights it applicability to opioids (narcotics), but it is equally useful for many other drug classes with known PK/PD interactions with ethanol, including but not limited to: 1) alcoholism treatments (e.g., disulfuram), 2) antibiotics (e.g., isoniazid, rifampin, metronidazole), 3) anticoagulants (e.g., warfarin), 4) antidepressants (e.g., tricyclic antidepressants, selective serotonin reuptake inhibitors, SRNIs), 5) Antidiabetic medications (e.g., oral hypoglycaemic agents), 6) antihistamines (e.g., diphenhydramine), 7) antipsychotics (e.g., chlorpromazine), 8) antiseizure medications (e.g., phenyloin), 9) antiulcer medications (e.g., cimetidine), 10) cardiovascular medications (e.g., statins, beta blockers, nitroglycerin, hydralazine), 11) opioids (e.g., oxycodone, morphine, codeine, propoxyphene), 12) non-narcotic pain relievers (e.g., NSAIDs such as aspirin; non-NSAIDs such as acetaminophen), and 13) sedatives/hypnotics (e.g., benzodiazepines such as diazepam, alprazolam, lorazepam, flurazepam; barbiturates such as secobarbital, pentobarbital and phenobarbital).

Optimal safety and efficacy monitoring of a patient receiving oxycontin (during titration phase and chronic management) using PD-based safety monitoring to detect both opioid and opioid-ethanol interactions on cardiorespiratory function is achieved according to the method of the present invention, with medication adherence and ethanol monitoring, and with continuous (patient places SPOC on nasal alae with each oxycontin ingestion) or intermittent (patients places SPOC on nasal alae by random call request), as described above.

Example 4

Optimal pain therapy in patients suffering cancer or postop pain using PK (e.g. using breath analysis to measure blood levels of narcotic), PD (respiratory-derived parameters using PPG)-, or a combined PK/PD-guided control of an infusor device delivering IV narcotics (opioids). In light of the present disclosure, a PD-based narcotic infusion system that provides drug effects on respiratory and cardiovascular systems is enabled and easily implemented by those skilled in the art.

Example 5

Safety and efficacy monitoring of a chronic pain patient prescribed a 1 month supply of opioid (e.g., Oxycontin) using PD-based safety monitoring is achieved according to the method of the present invention, with or without medication adherence, and with or without ethanol monitoring, as described above.

Example 6

Safety and efficacy monitoring of a chronic pain patient given a transdermal fentanyl patch using PD-based safety monitoring (intermittent or continuous, linked to a monitoring station) is achieved according to the present invention, with or without medication adherence, and with or without ethanol monitoring, as described above.

Example 7

Optimal anesthesia using total intravenous anesthesia (TIVA) in patients undergoing procedures using PK (e.g. breath analysis used to measure blood levels of anesthetic agents)-, PD (e.g., effect of anesthetic agents on cardiorespiratory-derived parameters from PPG)-, and/or PK plus PD-based system to control an infusor device to safely deliver IV agents. Drugs in this example include but are not limited to propofol, ketamine, fentanyl, and combinations of these agents thereof. The IV anesthetics could be mixed in a single syringe and delivered as a "cocktail" as the preferred embodiment, but alternately, individual IV anesthetics could be placed in different syringes and multiple infusion systems controlled by the system. Likewise, the system would preferably operate in a closed loop mode, but could also operate in an open loop mode. Taken together, a PK-, PD-, and PK+PD-based propofol infusion system that provides drug effects on respiratory and cardiovascular systems is therefore enabled and is easily implemented by those skilled in the art in light of the teachings provided herein.

Example 8

Trauma Environment—where Fluid Therapy is Tethered to Drug Therapy

While the following example provides considerations and embodiments of this invention which are particularly applicable in the battlefield context, those skilled in the art will appreciate, based on the rest of the disclosure and that which is described in this example, that there are many additional contexts, including civilian contexts, in which the embodiments described here are equally applicable. Thus, for example, for pilots at risk of GLOC, in firefighters at risk from fume inhalation, in sports divers, e.g. SCUBA divers, experiencing underwater seizures, heart attacks, loss of consciousness and the like, all could benefit by inclusion in their equipment of closed-loop or open-loop components of what is described in detail here under the rubric of the trauma environment system. Not all components need to be present in all such systems. At a minimum, what is required are the following components: at least one sensor adapted to measure at least one PD, PK, or PD/PK parameter of a subject; at least one processing system adapted to process signals acquired from the at least one sensor and adapted, on the basis of such processing, to instruct delivery of an agent to the subject; and at least one agent delivery system adapted to deliver to the subject an amount of agent instructed by the processing system. In preferred embodiments, as described below, the entire system is autonomous and self-contained. In other embodiments, the system is a closed-loop or an open loop system. In other embodiments, the system is in communication with external devices or people and is subject to optional external controls. In a highly preferred embodiment, the system includes a PPG, a nasal pressure sensor, an ECG sensor, and an integrated or separately emplaced nasal delivery system for delivering active agents, including in the form of fluids, gasses, aerosols, and/or non-aerosols, to the subject's nasal epithelium. The active agents could be stored in a container located near (or in) the nose, or at a more distant site from the nose.

Under emergency conditions, there are often situations where patients are injured, but optimal trauma support is unavailable for extended periods of time.

Trauma Environment Treatment (TET) system, as disclosed herein, is a unique and novel system and is a particular embodiment of the PPGcare™ system for use in a hyper-mobile, self-contained system for applications where subjects may be travelling to remote or hostile environments where injury is possible and where access to the subject by trained medical personnel may not be available at all or in a sufficiently short amount of time to prevent morbidity or mortality. The TET system, method and apparatus that allows individuals and/or other treatment providers to begin administration of opioids, fluids and if necessary other medications to reduce blood loss, tolerate blood loss and/or decrease the extent of TBI and PTSD.

TET consists of some or all of the following elements Numerals in the following description reference a figure (first numeral) followed by a second numeral for a given element, separated by a slash. Thus, 1/1 references element 1 in FIG. 1, 1/3 references element 3 in FIG. 1, etc:

1. A battery pack or access to existing power in the TET ensemble 1/1.

Figure 2:
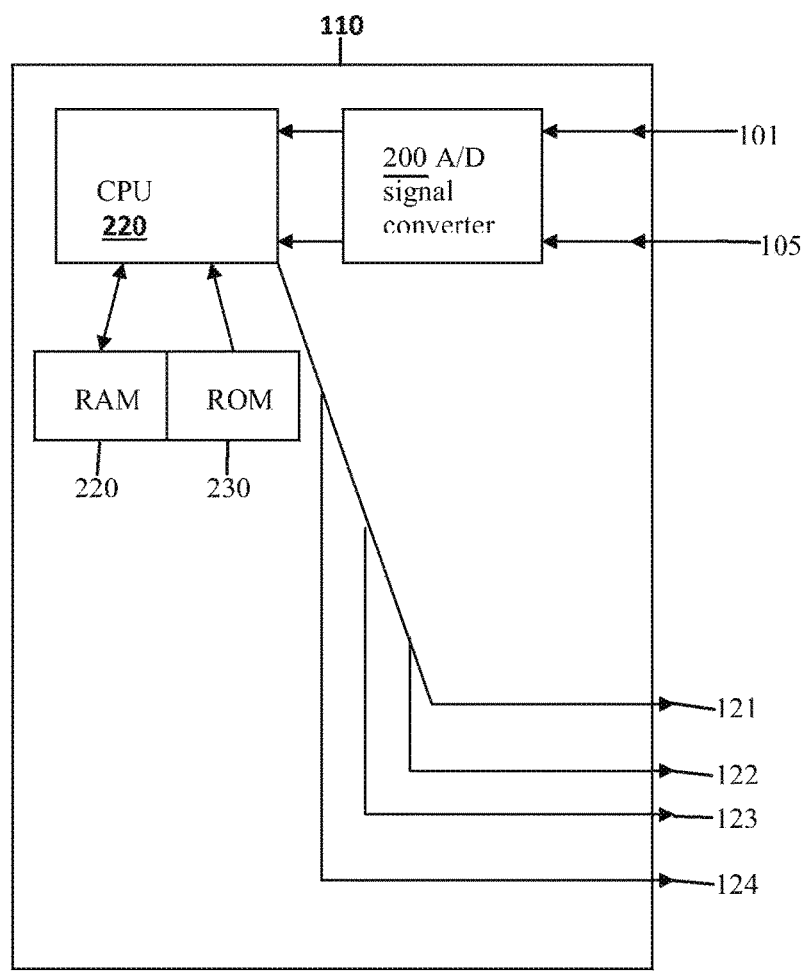
FIG. 2 provides an internal schematic representing PD, PK, or PD+PK and other relevant signals from the subject being converted into digital signals, if these are incoming as analog signals, and being processed via a central processing unit utilizing software implementing appropriate algorithms stored in Random Access Memory (RAM) or in Read Only Memory (ROM) or both, and then sending, via integrated or independent signal streams, controller information to the infusion pump.

2. An accelerometer or other motion (tilt, orientation, motion, elevation, or the like) sensing device 1/2 worn on the helmet of a subject 1/3 or other location on the head (e.g. behind the subject's ear) provides signals indicating whether a subject is actively moving or is inactive. This component is used primarily to "wake-up" the sensing system 1/4 so that it may remain in a standby status until needed. This reduces power consumption and the incidence of "false alarms". The accelerometer signal is a separate signal from PD and/or PK signals acquired by sensors for reading such parameters from the subject. Further, lack of movement by the subject especially in a recumbent (supine or prone) position may be indicative of a serious injury. The data from the accelerometer in conjunction with data from SPOC can be used assess whether a subject is injured or if the activity detected is very regular and vigorous, this may be indicative of seizure activity, as from a concussive head injury from an IED. Once wakened, the controller comprising a CPU 1/110 receives data 1/102, 1/102, 1/103, 1/104, 1/105 from the sensing device adhered to the subject 1/3, and, based on that acquired information, the controller/CPU 1/110, initiates delivery via a pump 1/120 of fluids and/or pharmacologically active agents 1/125, 1/126, 1/127, maintained in a secure compartment 1/130. These agents 1/125-1/127, for example, including but not limited to agents for providing analgesia, fluids and the like, are then infused via lines 1/122, 1/123, 1/124, optionally via a common line 1/121 (see discussion below where such a common line may be directed for delivery to the nasal septum). As shown in FIG. 2, the outputs via lines 1/101 and/or 1/105 are received by an analog to digital converter if necessary 2/200 which transmits the signals to the CPU 2/210, which has stored in RAM 2/220 and/or ROM 2/230 appropriate signal processing algorithms for interpretation of the incoming subject physiologic information 2/101, 2/105, for outputting instructions to initiate infusion to the subject of appropriate fluids and/or pharmacologically active agents, 2/121, 2/122, 2/123, 2/124.

Figure 3:
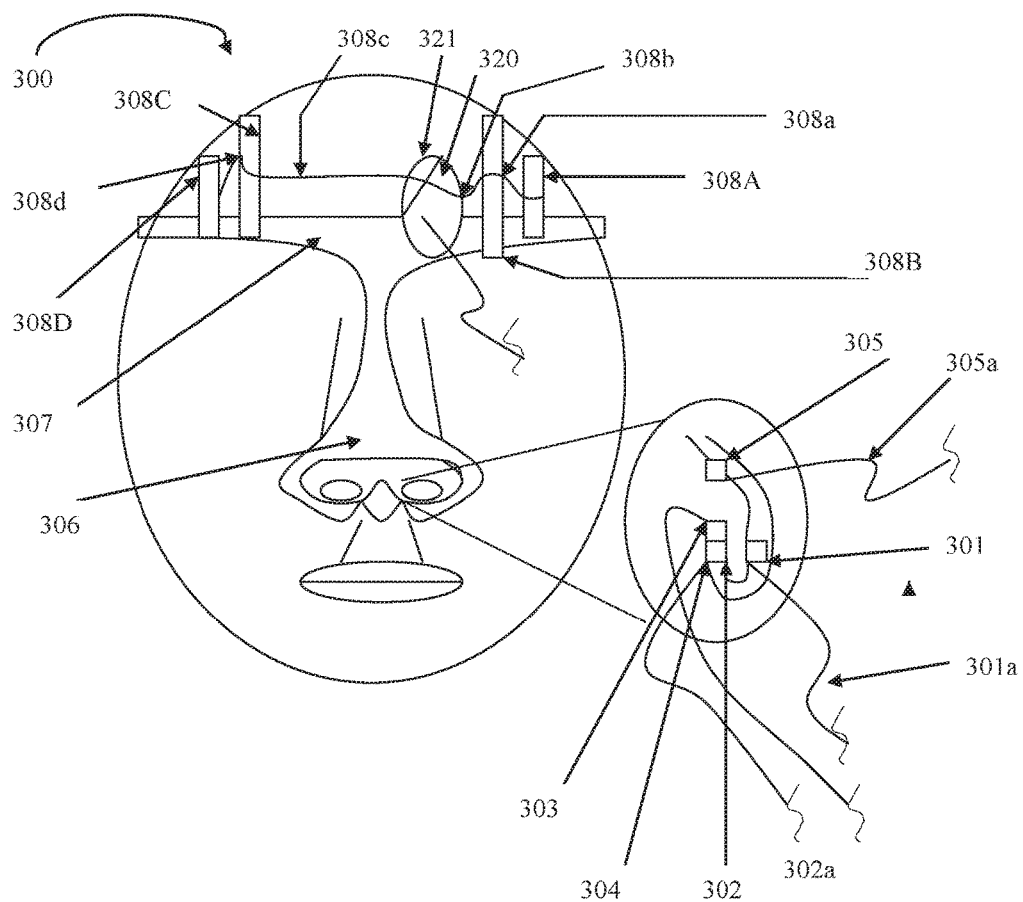
FIG. 3 provides a schematic representation of a preferred subject interface component of the system of the present invention whereby particular measurements of relevant PD, PK or PD+PK and other relevant signals are obtained from a Single Point of Contact (SPOC) on the subject (exemplified in the diagram by the nasal alae), and wherein, at the same time, fluids and drugs are delivered intranasally, e.g. to the mucosa of the nasal septum or nasal turbinates. This embodiment is particularly suited to the needs of subjects according to the TET embodiment of the invention, but may be utilized also in civilian contexts.

3. As shown in FIG. 3, at least one, and preferably two SPOC sensor assemblies 3/300 each containing pulse oximeter components (LED 3/301 and photodiode 3/302), nasal pressure sensors, 3/304, and in one embodiment, one of two ECG electrodes, 3/305 (the other to be placed in the undergarments or on the torso of the subject). Such components are known in the art, for example, for obstructive sleep apnea (OSA) monitoring. As shown in FIG. 3, one SPOC sensor assembly, 3/300, is affixed to each nasal ala and joins below the bridge of the nose to form a single device that can be easily emplaced by the subject or treatment provider. In alternate embodiments, SPOC units consist of a unit that is attached to single alae. However, the redundancy, improved fixation and additional access to the nasal epithelium makes a dual SPOC a preferred embodiment according to this aspect of the invention.

4. Means are provided to fix the SPOC sensors securely to the subject. For example, the sensor assembly may be affixed by a retainer device, 3/306, which fits over the bridge of the subject's nose and/or up to the helmet or other fixation point on the forehead, for example, using a headband, 3/307. The forehead band, 3/307, communications ensemble or the helmet optionally contain reservoirs of medications and or fluids, 3/308, (3/308A, 3/308B, 3/308C, 3/308D, represent separate reservoirs with same or different fluids/medications), each of which is linked (via communication lines 3/308*a*, 3/308*b*, 3/308*c*, 3/308*d* to and activated for release of fluid/medications by the computer/CPU 3/320 which controls the closed-loop system, and other components/sensors of the system. The computer/CPU, 3/320, receives signals, 3/321, from the PD, PK or PD+PK sensors 3/301, 3/302, 3/305, affixed to the subject via communication line(s) 3/301*a*, 3/302*a*, 3/305*a*.

5. In one preferred embodiment shown in FIGS. 3 and 4, a small tube, 3/303, is incorporated into the assembly and is placed inside the subject's nostril and is pointed toward the nasal septum (nasal epithelium/mucosa, especially Kiesselbach's plexus and/or to the nasal epithelium/mucosa of the nasal turbinates, which delivers aerosols or non-aerosolized fluids, preferably in pre-metered doses of medications (e.g. opioids, anxiolytics, steroids, vasoactive drugs, and the like) using appropriate fluid delivery systems known in the art which are adapted for particular target delivery modes as described herein. Thus, for an intranasal delivery site, e.g. for delivery to the nasal epithelium, as shown in the drawings, a fluid nozzle aimed at the nasal mucosa, is incorporated into a nasal alar attachment housing. For intravenous delivery, a tube with an IV needle, such as those known in the art, may be used. Based on the present disclosure, those skilled in the art may develop any number of equivalent delivery means to those described herein for delivery to any appropriate subject. Thus, in alternate configurations, the delivery device may be a needle or catheter which is to be inserted intravenously, intraperitoneally, intraosseously, intracardiacly, or the like, but the non-invasive assembly for intranasal delivery is preferred.

6. Where utilized, the intranasal tube, 3/303, is connected to a drug delivery system capable of providing medication through the nasal epithelium delivery tube using aerosolized- and/or non-aerosolized-based systems 3/303. The aerosolized and/or non-aerosolized medication(s) is/are optionally stored in pressurized canisters, 3/308, adapted to provide metered doses upon actuation of a valve or a small pump that delivers aerosolized and/or non-aerosolized doses from a given container, 3/308, via delivery line(s) 3/309 connected to said nasal epithelium delivery tube 3/303. The components of this device should be tamper-proof to prevent use of stored medications for other than intended purposes. Alternatively, the canisters 3/308 may be housed elsewhere on the subject, such as on a belt, which may also house the computer/CPU 3/320, pump if required 3/321 and communication lines and fluid delivery lines (3/308*a-d* and 3/309, respectively). The medication canisters or backup or replenishment containers are optionally carried independent of the other components of the system by a limited number of individuals responsible for the canisters and made available to personnel in need of the given medications. Medications in the canisters are optimized to maintain pharmacological potency under a wide range of temperature and atmospheric conditions, for example, by inclusion in the medication compositions appropriate preservatives and the like. Using SPOC parameters to determine inspiration, medications can be metered to optimize delivery to the nasal mucosa.

7. Optionally, nitric oxide, histamine, methacholine or the like is included in the medication delivery system, either as part of the medication compositions or as a separate feed to the nasal mucosa, to increase permeability of the nasal mucosa to the delivered medications.

8. Highly concentrated doses of opioids (fentanyl, sufentanyl, and the like); opioid antagonists (naltrexone/naloxone for "recovery" if too large a dose of opioids is delivered); vasoactive drugs, particularly vasopressin; steroids (dexamethasone and others); dissociative agents such as ketamine; anxiolytics (benzodiazepines, gabapentin, pregabalin) and the like, are included as single component compositions which are separately deliverable to a subject in need of such agents, based on measurements of their PD parameters. Such medications are provided via separate infusion lines to the subject or may be combined for delivery through a single line.

9. Canisters or containers for medications and fluids, 3/308, are preferably adapted so that they can be removably but securely inserted into the system (e.g. canisters or container that can be snapped into the system by engaging clips and holding compartments adapted for protection and engagement of such canisters or containers) so that different medication combinations can be provided. At least 2 drug or drug combinations are separately deliverable in an embodiment utilizing two SPOC sensors (one on each nasal alar).

10. A small central processing unit (CPU), 2/210, 3/320, including algorithms/software stored in RAM, 2/220, and/or ROM, 2/230 facilitate closed-loop (servo) delivery of medications and control of the medical devices (sensors and infusion mechanics).

11. Small infusion pumps (e.g. ambIT PCA pump, http://www.ambitpump.com), 3/321, deliver volume expanders (hypertonic saline; dextrans) via subcutaneous, intraosseous, or IV routes when available. This also extends the range of the TET to other levels (II-V) of medical care.

12. A second "peripheral" pulse oximeter sensor (fingers, toes, ear, etc) to provide information on volume status, or the status of an injured extremity. This is a standard finger/toe pulse oximeter probe/sensor which can be clipped (usually with a spring loaded design) to a finger or toe. The sensor usually contains to LED photodiodes (one emitting light in the IR range and one emitting red light). A photodetector evaluates the IR and red signals as well as the background signal sequentially and the pulse oximeter calculates the $SpO_2$ by calculations well known in the art. In the present application the sensor may be connected directly by a cable, or more advantageously by a Bluetooth or other wireless connection to the computer. The ability to simultaneously measure $SpO_2$ and PPG from 2 sites allows evaluation of volume status and/or status of a compromised extremity. See for instance U.S. Pat. No. 6,909,912 Non-invasive perfusion monitor and system, specially configured oximeter probes, methods of using same, and covers for probes.

13. Nasal pressure and/or flow sensors, 3/304, and/or PPG sensors, 3/301, 3/302, are utilized to detect phase of respiration and meter doses of medication only during the inspiratory phase.

14. Three levels of care provided in the trauma treatment environment prior to stabilization are provided by this system:
   a. Complete autonomous care by the subject.
   b. treatment providers in the surrounding zone may assist, for example, by emplacing the SPOC sensor assembly if the subject is unconscious or unable to apply the assembly to him/herself. The system is still "autonomous" as it is not being remotely controlled.
   c. Remote communication of the vital sign information and control of the TET once the SPOC is emplaced.

Figure 4:
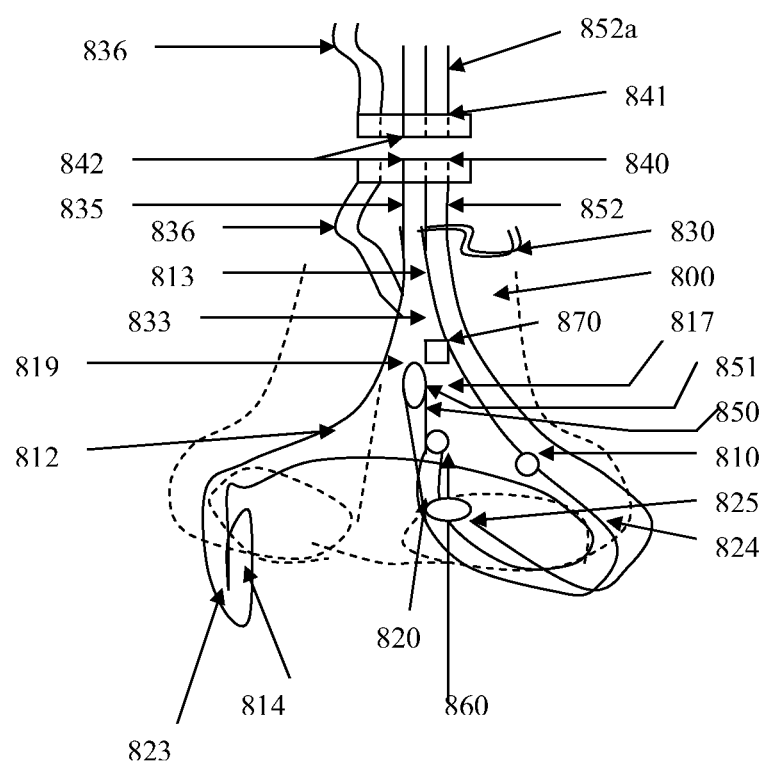
FIG. 4 provides a more detailed schematic representation of the subject interface at the nasal ala shown in FIG. 3 and a description of novel features of an SPOC probe embodiment according to this invention.

In FIG. 4, further details are provided for a preferred embodiment of the nasal SPOC system contemplated here, in which, integral with the acquisition of nasal pressure and PPG signals of the subject, the nasal sub-system is also adapted to delivery agents in fluid, gas, aerosol and/or non-aerosol form to the nasal epithelium. It should be noted, however, that the SPOC system may be adapted for emplacement, for example, on the ear of the subject, while the agent delivery subsystem is adapted for delivery to the nasal epithelium. That is to say, it is not necessary, and in some circumstances may be preferred, for the PD, PK or PD and PK signal acquisition site and the site of fluid or pharmacologic agent delivery to either be the same or different sites. Where fouling of the signal acquisition system by delivery of fluids, gases, aerosols and/or non-aerosols is a risk, it is preferred, of course, to separate the signal acquisition subsystems and the site of agent delivery of the agent delivery subsystems.

Turning to FIG. 4, a detail is provided for a novel nasal alar PD parameter measurement system which is integrated with a nasal epithelium agent delivery system. This subsystem is, for all intents and purposes, similar to the system 800 described in US2010/0192952, paragraphs 0056-0057, herein incorporated by reference, and, as modified below, specifically incorporated with respect to FIG. 4 herein.

A nasal probe embodiment 800 is configured for obtaining plethysmography readings and/or oxygen saturation readings from the user's nasal alar region. The nasal probe embodiment 800 comprises a base portion 813 which runs along the longitudinal ridge of the nose. At the distal end 833 of the base portion 813 is a bridge portion 819. The bridge portion 819 runs transversely across the nose and comprises a right flap portion 812 at one end and a left flap portion 817 at its left end. The right and left flap portions 812, 817, respectively, are positioned above the right and left nares of the user. The left flap 817 has attached thereto or integrated therewith at least one LED 810 or other light source. Extending down from the right and left flaps 812, 817 are a right extension 823 and a left extension 824. Attached to or integrated with the left extension 824 is a wing fold 820 that is configured to be inserted into the user's left nostril. The wing fold 820 has at its distal end a photodiode 825 attached thereto or integrated therewith. The wing fold 820 is designed to bend over and be inserted into the user's nostril such that the photodiode 825 is positioned directly across from the LED 810 located on the exterior of the user's' nose. Extension 823 comprises wing fold 814 which is designed to be inserted into the user's right nostril. The positioning of wing fold 814 in the user's right nostril provides a counter force to the wing fold 820 which would tend to pull the probe 800 towards the left. Thus, the right flap 812, right extension 823, and right wing fold 814 act together to assist in securing the nasal probe 800 in place. The nasal probe 800 is provided with an adhesive material 835 and a peel-back layer 830. Before use, the peel-back layer 830 is removed and the adhesive 835 assists in securing the nasal probe 800 to the skin of the user's nose. At the proximal end 834 of the base 813, a connector 840 is provided. Wires 836 are provided in the nasal probe embodiment and run from the LED 810 and photodiode 825 up to connector 840. Furthermore, a flex circuit may be attached to or integrated with the probe embodiment 800 so as to provide the necessary wiring to the LED 810 and photodiode 825.

The connector 840 is adapted to securely mate with connector 841 via clips 842 to thereby provide electrical continuity for wires 836 to wires 836*b* which connect to the processing elements of the system described elsewhere.

In addition to the elements known from US 20100192952 described above, the novel nasal alar sub-system of the present invention further includes additional key elements, novel to the invention disclosed herein.

A first novel key element shown in FIG. 4 is an agent (fluid, aerosol and/or non-aerosol or gas) delivery tube, 850, which runs along the nasal alar assembly into the nose and is oriented toward the intranasal epithelium at its distal end 851 (also shown in FIG. 3 as element 303). At its proximal end 852, the agent delivery tube 850 is integrated with connector 840 which, when coupled with connector 841, again via clips 842, to sealingly connect with extension 852*a* which runs to the agent reservoir(s) of the system described elsewhere, and which, on receiving instructions from the controller, also described elsewhere, results in administration to the subject of selected fluids and/or pharmacologically active agents. Of course, more than one separate tube line 840 may be provided, permitting more than one agent or more than one agent combination to be delivered to the subject at any given time. Ideally, the agent delivery tube internal diameter is sufficiently small to minimize any dead volume while at the same time being sufficiently large to permit ready delivery of agent to the subject. Those skilled in the art can achieve appropriate configurations based on this disclosure without undue experimentation.

A second novel key element shown in FIG. 4 is a nasal pressure sensor, 860 (also shown in FIG. 3 as element 304). The nasal pressure sensor detects small changes in pressure near the nasal opening caused by breathing. Typically these changes are less than 2-3 cm H20 (0.03 PSI) must be very sensitive and accurate. Even during mouth breathing, pressure fluctuations can be detected near the nasal opening, although the pressure changes are even less than described above. Typically, a nasal pressure measurement system consists of a small bore sensing line inserted into the nasal opening that connects to a very low pressure sensor located a small distance from the sampling point to minimize pressure losses in the sampling line (although in theory, a pressure sensor could be embedded in the nasal opening, this is not currently implemented due to the size of the precision pressure sensors). Pressure fluctuations measured by the pressure sensor (various types of pressure sensors are common and known to those skilled in the art) are typically temperature compensated and digitized for processing by a digital processing system. In addition to the decrease in pressure during inhalation and increase in pressure during exhalation, the shape of these waveforms can indicate important aspects of the breathing such as effort to breath, occlusions or high resistance during inhalation or exhalation, among other attributes).

In addition to a pressure sensor, flow sensors can also be used. Pressure sensors are typically considered to have more information related to wave shape, but flow sensors can be very simple thermistors or other devices that can be directly inserted into the nasal opening to reduce the need for tubing.

A third novel key element of the shown in FIG. 4, is an ECG lead, 860 (also shown in FIG. 3 as element 305, along with its communication line 305*a*) which provides the system of this invention the ability to secure direct cardiac signals. Along with a second lead which can be attached to the undergarments of the subject or directly to the skin as a conventional ECG electrode is attached, a single lead ECG can be obtained. Addition of an ECG signal allows not only the detection of the heart rate, but detection of arrhythmias. Also several derived signals such as pulse transit time and can determined by using the ECG signal in conjunction with the PPG signal.

Through use of the novel alar probe design described above, (in addition to the previously appreciated superior probe position on the lateral side of the nostril just behind the prominent part, which is referred to as the fibro-areolar tissue, see US20100192952), the probe of the present invention, for the first time, also facilitates closed-loop as well as open-loop delivery of fluids and pharmacologically active agents, non-invasively, to a site of excellent access and bioavailability (the nasal epithelium). It also provide more accurate measurements of the subject's breathing patterns (via the nasal pressure transducer sensor), and ECG readings. Of course, in various embodiments, not all of these elements are required to be present. For example, the agent delivery tube and the nasal pressure sensor may be present, while the ECG sensor may be absent or located elsewhere. Likewise, as mentioned above, the agent delivery system may deliver agents to the nasal epithelium, while the SPOC may be emplaced at the subject's cheek or ear. Alternatively, the SPOC may be emplaced at the subject's nose, while the agent delivery system delivers agent to the subject at any other convenient site, including but not limited to intraperitoneally, intravenously, sublingually, etc. Those skilled in the art will appreciate that the present system accommodates a large number of permutations and combinations, without departing from the central teachings of this invention. It will also be appreciated that a similar arrangement of components may be included for both nares of a subject as described above, such that there is redundancy in the system and, in addition, there are additional options available for providing different drug combinations to the left and right nasal epithelia.

Thus, in a preferred embodiment, the alar probe 800 is dimensioned so that placement onto the fibro-areolar region is optimized for the user. Other embodiments are contemplated as well, including clips, hooks; and reflectance designs for either inside or outside nose. which could be inconspicuous and would be especially advantageous for ambulatory and long term use.

TET system optionally remains in place as the subject is transferred to higher levels of medical care for both monitoring and drug therapy. Once IV access is obtained, drug delivery can be switched to this route. Preferably, the TET remains in place through all levels of medical care and it preferably is adapted to interface with other medical treatment and monitoring systems.

In one embodiment, where the subject is undergoing surgery or anesthesia/conscious sedation is otherwise required, a propofol sensor/monitor can be attached to the SPOC array, or alternatively in-line with an endotracheal tube, laryngeal mask airway, etc. to allow physicians and physician extenders to provide anesthesia/conscious sedation with propofol and propofol "cocktails" (e.g. combinations including analgesics and Ketamine)

The complete TET ensemble preferably adds only a small fraction to the weight (normally 60-80 pounds) carried by the subject.

In real-world practice, an injured subject who is conscious is able to rapidly emplace the TET on his/her nose or other appropriate site on the subject and the system immediately activates and begins providing pain medication and other medications based on the sensor data interpretation and algorithms. If the injured subject is incapacitated, a fellow subject emplaces the SPOC system on the subject. Additionally, since each subject preferably carries medications adapted for insertion into the TET system, they could be used on a wounded subject, thus increasing the amount of medication available in the field. Alternatively, or in addition, the TET assembly is in place as in integral part of a helmet and/or telemetry gear.

A key feature of the TET is its ability to deliver medications in a timely manner through a site where absorption is almost as reliable as IV injections. Multiple studies have shown that the nasal epithelium absorbs about 60-80% of the dose of an IV injection of the same quantity of medication, (see, for example, Velhorse-Janssen, et al., 2009, "A Review of the Clinical Pharmacokinetics of Opioids, Benzodiazepines, and Antimigraine Drugs Delivered Intranasally", Clinical Therapeutics, Vol. 31, Number 12, pp. 2954-2987; Moksens et al., 2010, J. Opioid Manag., 6(1):17-26, "Pharmacokinetics of intranasal fentanyl spray in patients with cancer and breakthrough pain"; Dale et al., "Nasal administration of opioids for pain management in adults", Acta. Anaesthesiol Scand. 2002; 46:759-770). This will likely be true even if a subject is hypotensive since this area of the nasal septum is richly supplied by arteries which are branches of both the internal and external carotid. Likewise, vasopressin (unlike alpha adrenergic vasopressors) is unlikely to cause intense local vasoconstriction in the nasal area, thus allowing absorption of other medications given at the same site.

It is important to note that the TET system is adapted to provide both the initial monitoring and medication delivery to the injured subject and then continue to provide monitoring as well as medication delivery by conventional routes once IV access is obtained.

The accelerometer or like motion and/or orientation detection sensor, monitors whether a subject is actively moving or has suddenly ceased to move. Preferably, the accelerometer or like motion sensor is used to limit the power consumption of the TET system by maintaining it in "sleep" mode until it senses a sudden change in the subject's level of activity. In one embodiment, the accelerometer is adapted to detect very regular but intense body movement indicative of seizure activity, in which case a signal from the accelerometer sensor is processed by the controller to provide a benzodiazepine or other antiseizure medications if the subject system is in place or once the SPOC assembly is emplaced by a other personnel. The accelerometer would also be capable of monitoring the body position of the subject. A long period of inactivity in the prone or supine position is optionally programmed into the system to trigger a remote alarm so that other personnel are alerted to determine the status of the subject being monitored. Likewise, the accelerometer or other motion sensor is used as an additional monitoring parameter while a subject is being treated by the TET system. A sudden reduction in movement is optionally programmed into the controller as an indication of inadequate pain control in the setting of acceptable vital sign parameters, while a reduction in movement coupled with unacceptable vital signs is optionally programmed into the controller to be interpreted as an urgency requiring provision of resuscitative measures. In some instances, the accelerometer or alternate motion sensing component of the TET system is the first indication of a problem with a subject, in some instances, even prior to the emplacement of SPOC on the subject—provided the subject is carrying the system somewhere in his/her kit.

Example 9

Photoplethysmography Sensor and Nasal Pressure Sensor Signal Processing and Control of Infusion Pump In an exemplary embodiment of this invention, a prototype has been developed to confirm the working principles outlined herein above. In this prototype, photoplethysmography sensor signals and nasal pressure signals are acquired from a subject, the signals are processed and output controls to an infusion pump are produced to control drug delivery. This example demonstrates that the applications of the present technology are operative with these and a wide variety of other possible sensors.

A subject was fitted with a nasal photoplethysmography unit and a nasal pressure transducer unit. Raw data from the photoplethysmography (PPG) sensor and the nasal pressure sensor were acquired and processed as described below to return heart rate, breath rate, and obstruction level information with respect to the subject. These parameters are then used to govern pump titration rate.

As discussed generally above, signal acquisition from the subject may be initiated manually, or signal acquisition may be initiated automatically, for example, as a result of accelerometer signals to the control unit indicating a change in subject status, including, but not limited to, a beyond threshold period of inactivity, excessive, repetitive shaking, indicative of seizure, rapid change in vertical to horizontal orientation, indicative of a fall, or other pre-determined motion-related parameters. Of course, other motion sensing-means besides an accelerometer may be utilized for this purpose.

Definitions, Acronyms, and Abbreviations

DC=The low frequency component of either the red or infrared channels of the PPG sensor found by subtracting the AC component from the raw signal.
AC=The cardiac or high frequency component of either the red or infrared channels of the PPG sensor
DC=The low frequency component of either the red or infrared channels of the PPG sensor found by subtracting the AC component from the raw signal.

Algorithm Description

The algorithm can be broken up into three main phases:
1. Filtering and preprocessing: streaming data is separated into the channels that will be used in parameter calculation and individual breaths and heart beats are identified and marked.
2. Parameter Calculation: the main predictive elements of the model are computed
3. Model output generation: the parameters are combined into the desired outputs Filtering and Preprocessing Here the IR and RED channels of the PPG signal are first sorted into AC and DC channels using a novel algorithm. Whereas a standard low pass filter is typically used to separate the DC component from the raw PPG signal, this device uses the following unique approach:
1. An initial guess of heart rate (such as 60 beats per minute) is used at the onset of processing.
2. This heart rate is converted into an appropriate search window (such as 1.5/(heart rate)).
3. A local maximum is found in the raw PPG signal within this search window. This is the peak of a single heart beat.
4. A new estimate of heart rate is found by subtracting the time of previous maximum from the current maximum. This new estimate of heart rate is typically averaged with previous heart rate estimates for stability.
5. The "valleys" are found by finding the minimum value of the raw PPG signal between the current maximum and the previous maximum.
6. If there is more data, return to step #2 and repeat.

Using this approach, the locations of the peaks and valleys for each heart beat are identified and stored in a table. Halfway between each peak and valley a "midpoint" is identified. The DC component is then found by a linear interpolation between these midpoints.

This approach is different from traditional approaches to finding the DC component in that it produces an estimate that does not have a lag or time shift relative to the raw PPG signal. Rapid changes in DC baseline are, therefore, more accurately captured using this approach.

The AC component is then found using a point-by-point subtraction of the DC component from the raw PPG signal.

Next, the DC component is filtered using a band-pass Butterworth filter to find the respiratory component of the PPG signal. Two possible ways the band-pass cutoff frequencies can be determined are:
1. Use a set range based on common breath rates (such as 1 to 0.1 Hz)
2. Use the nasal pressure signal to determine the average breath rate and then center the filter cutoffs over that breath rate.

The nasal pressure signal is then also filtered using a band-pass Butterworth filter to remove artifacts and noise. Filtering the nasal pressure signal helps identify prominent breath features (peak inhalation, peak exhalation, etc) and helps reject noise and motion artifacts.

Finally the individual breaths are identified in the pressure signal. The start-of-inspiration (SOI) and end-of-breath (EOB) as well as the peak inhalation and exhalation are found and stored in a table.

Parameter Calculation

From the nasal pressure and two PPG channels (IR and RED) a wide range of parameters can be calculated to help predict respiratory and cardiac phenomena. Some of these parameters include:

Nasal Pressure Amplitude: the distance between the peak of inhalation and the peak of exhalation for each breath averaged within a time window (1 minute for instance)

Nasal Pressure Breath Rate: The average breath rate found within a window of time.

Nasal Pressure Amplitude Variance: the variance of all the nasal pressure amplitudes found within a time window.

Nasal Pressure Breath Period Variance: the variance of the individual breath times (end-of-breath time minus start-of-breath time) for each breath within a time window.

DC Drop: the distance between the base of a DC drop and its baseline (baseline is typically the average DC value over a larger time window)

DC Drop Duration: the time it takes for the DC component to return to baseline after a drop from baseline.

DC Drop Area: the area found by integrating the signal (DC Baseline-DC Component) during a DC drop from baseline.

AC Heart Rate: the average heart rate found in the AC component within a time window.

AC Heart Period Variance: the variance of the individual heart beat lengths within a time window.

AC Amplitude: an average of the individual heart beat amplitudes (maximum minus minimum) within a time window.

AC Amplitude Variance: the variance of the individual heart beat amplitudes within a time window.

SAO2 Drop: the drop in the blood $O_2$ saturation found by converting the IR and RED PPG signals into an estimate of blood oxygenation (ie the more traditional use of the PPG signals)

PPG Resp Energy: the energy in the respiratory component of the PPG signal within a time window.

Model Output Generation

The parameters described above are typically converted into unit-less "percent" values. This is done by calculating a baseline using a large time window and then each parameter is converted to a percent-change-from-baseline. After this conversion, the parameters are then combined in appropriate proportions to generate model outputs. Most commonly, these parameters are combined using a simple linear combination though a more advanced method such as tap-delay lines or neural networks can also be used.

Figure 7:
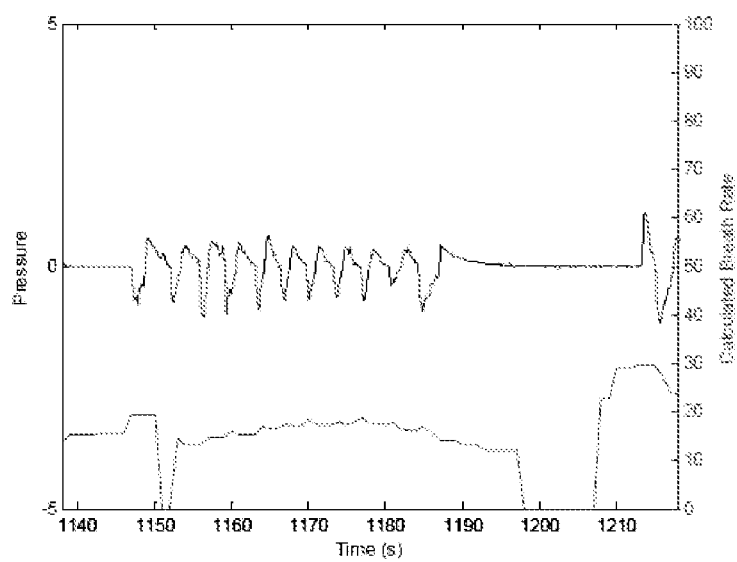
FIG. 7 shows the system's ability to detect another respiratory pause.

The parameters described above can be combined to produce signals that regulate the titration of the infusion pump. The two main model outputs that control the pump are "Breath Rate" and "Obstruction Level". Other indications of respiratory or cardiac distress can also be inferred from these parameters and pump infusion rate can be adjusted accordingly Algorithm Validation Results A preliminary validation process has been conducted by collecting data on subjects simulating respiratory failure and visually inspecting the prototype's output. Some examples of these tests are shown in FIGS. 7 and 8.

Based on the processing of the PPG and nasal pressure signals, the system of this invention is able to select which drugs, and the quantities of such drugs to be administered to the subject. Of course, ongoing iterative application of given pharmacologic and fluidic interventions are reflected in the ongoing monitoring of PD, PK or PD and PK parameters acquired from the subject, allowing for dynamic modifications to the intervention, within appropriate pre-set limits defined by qualified medical personnel for a given context.

Example 10

User Interface

In preferred embodiments according to this invention, the closed-loop or open loop system or apparatus is emplaced on a subject, either by the subject or a colleague, physician, or the like. On being emplaced, the system initiates, conducts an internal self check to ensure that it is operating properly, that it has sufficient power for reliable operation, that it is properly interfaced with the subject and is able to acquire appropriate PD, PK, or PD and PK signals from the subject. The thus emplaced and properly operational system, in a preferred embodiment, then goes into a sleep or standby mode in which operational parameters are minimized along with minimal power consumption.

On being stimulated by an appropriate wake-up signal, which may be the subject pressing a start button, or an integrated motion sensor such as an accelerometer recognizing a motion state that is defined as requiring wake-up (e.g. excessive vibration, or no motion at all by the subject, or a sudden change in vertical to horizontal orientation), or due to an external telemetry signal from a central monitoring station, the system wakes up, quickly performs an operational self check and then measures appropriate PD and/or PK or other parameters for the subject. If all parameters check out as being normal or within pre-defined acceptable tolerances, the unit may once again enter a sleep mode. If any parameters are out of pre-defined tolerance, the unit immediately initiates delivery to the subject appropriate agents (fluids and/or nutrients or pharmacologically active agents), to bring the subject's parameters back within pre-defined acceptable tolerances. In the TET system embodiment described above, in a preferred embodiment thereof, the unit is entirely self-contained and autonomous and requires little or no intervention from the subject themselves or from external personnel.

Figure 5:
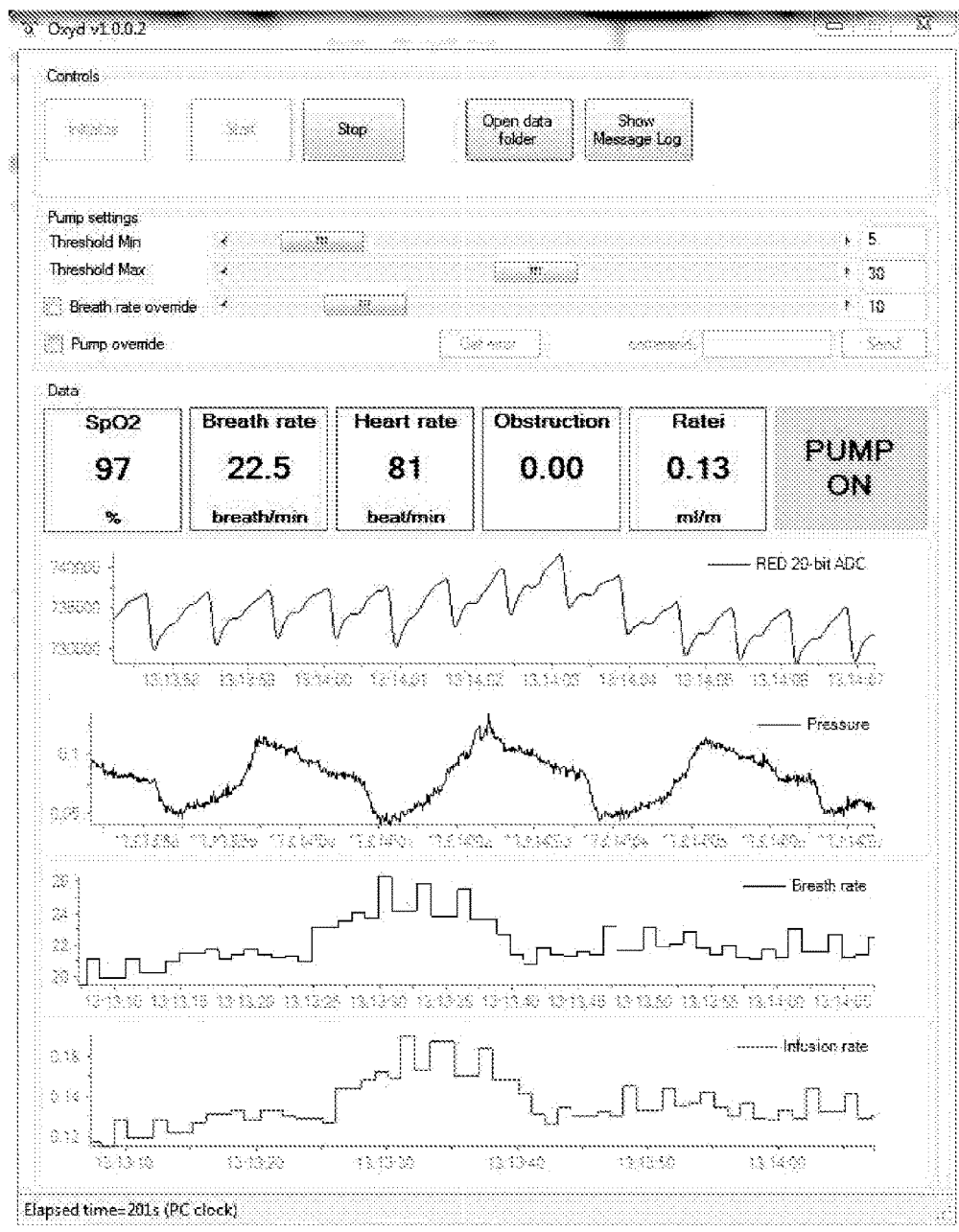
FIG. 5 provides photographic depiction of the user interface of a prototype of one embodiment of the apparatus according to this invention. the "Red" signal shows the heart beats in the pleth; in blue, pressure waveforms reveals the decreases in nasal pressure during inhalation and the increases during exhalation, occurring more slowly than the heart beats; the breath rate and infusion rate are on a slower time scale in the bottom two plots; an additional box is included that shows the "Obstruction level".
Figure 6:
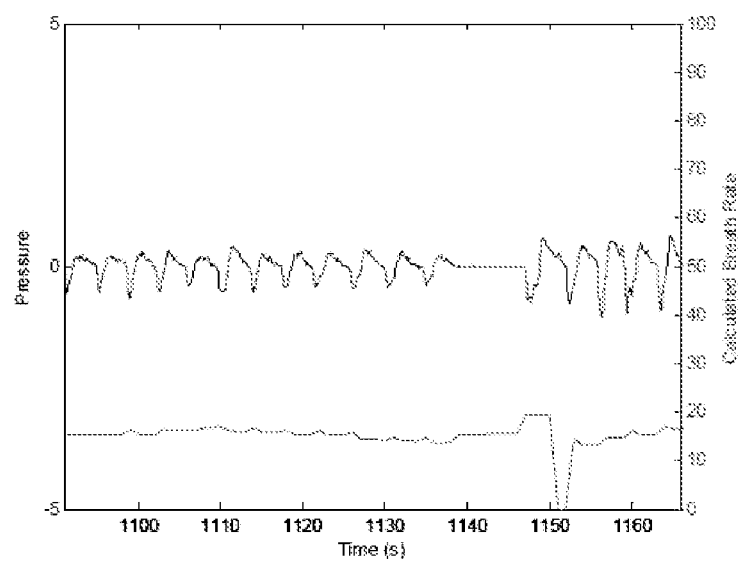
FIG. 6 shows the raw pressure signal and model output for breath rate during a small pause in breathing.

In an operational prototype of the present invention, a graphical user interface is provided, shown in FIG. 5. This is not intended to limit the interface options that are available in the apparatus or system of the invention. Rather, this is intended only to show that at the date of filing of this application, the system according to this invention is operational and in the possession of the inventors and to further extend the written description, comprehensibility and enablement for the present invention.

Turning to FIG. 5, it following elements can be seen and are understood as follows:

At the top of the figure, a variety of settings for the pump control software are shown, including the minimum and maximum thresholds that determine when the pump is fully on and when it is fully off. There is an override for the pump and breath rate to permit manually setting the pump or the breath rate.

Numeric values are shown for breath rate, heart rate, and ratei, (ratei is the current infusion pump setting [rate of infusion], which changes with breath rate or other cardio-respiratory parameters (e.g., respiratory effort, heart rate, arrhythmias), and an indicator that the pump is currently on.

The red signal is the red signal from the pulse-oximeter. There are two raw signals from the pulse-ox, infrared and red that are used in combination to determine the oxygen saturation. The IR signal is less sensitive to saturation changes and thus provides a more stable signal for PPG processing for purposes of this invention.

The AIN 0 signal is the nasal pressure indicating the change in pressure in the nasal opening during breathing. AIN is analog input 0 from the A/D converter, which is obtained from the pressure sensor. This signal very accurately represents breathing, including when mouth breathing is occurring.

The first two graphs are 10 second plots showing the real-time breathing and pulse. The next two graphs are 1 minute long graphs of breath rate and infusion rate, showing how the infusion rate changes over time based on the measured breath rate.

The Red 20 bit ADC value is obtained via the OxyPleth pulse oximeter. In practice, this would be the value coming directly off the photodetector when the red LED is pulsing, (typically, pulse oximeters pulse red and infrared light alternatively into a single photodetector). Both signals are obtained by the PC via the serial port of the OxyPleth.

The AIN0 is the nasal pressure signal obtained through a nasal oxygen canula and is converted via a very sensitive pressure transducer (Microswitch, part #DCXL01DS) and then A/D converted via an A/D converter.

The breath rate is calculated from the nasal pressure signal by detecting changes in pressure during the breathing signal, or alternatively can be calculated via changes in the PPG signal.

The infusion rate signal is sent to the infusion pump to dynamically control it. Currently, this signal is derived from the breath signal (which comes from the nasal pressure signal, but could also come from the pleth/IR signal). When the breath rate is high, the pump is on fully. When the breath rate falls below the upper threshold, the pump rate decreases until the lower threshold, at which point it turns off. This represents one simple method of controlling the pump. There are much more sophisticated ways in which those skilled in the art could modify this, based on the present disclosure, including, but not limited to, by using breathing pattern characteristics, such as entropy of the breathing pattern, and the like.

The DLL=true shows a debug statement indicating that the DSP algorithms are being called and returning valid data (e.g. the interface software collects the data and sends it to the DSP algorithms in a separate DLL. When the DLL successfully processes the waveform data and returns the information to the user interface, it returns the data, this indicator says true.

Example 11

PPGcare™ in Combination with the Subject Physiological Monitor(s) According to the Present Invention Introducing PPGcare™

PPGcare™ provides real-time monitoring and assessment of the total pharmacodynamic (PD) impact of drug delivery on the patient's well-being. The system monitors the physiological effects of a patient's drug regimen on their cardiopulmonary status. In addition to the commonly monitored vital signs such as heart rate and oxygen saturation, PPGcare™ measures respiratory rate and analyzes photoplethysmography (PPG) signals for hypopnea, central and obstructive apnea, and trends these values to determine the degree of respiratory depression and respiratory "effort". Because these measurements are obtained from sensors at a "single point of contact" (SPOC) on the nasal ala, surrogates for cerebral blood flow and venous capacitance can be measured.

From the central alar source, the PPGcare™ provides real-time heart rate, oxygen saturation, respiration rate, respiratory effort, and respiratory obstruction index. The system directly monitors the PD effects of all the factors that may contribute to hypopnea and apnea, and monitors the combined effects of hypoxemia, opioids, other drugs, and the patient's physiological state. PPGcare™ ensures the safest pain medication infusion based on a robust and accurate PD assessment of the patient's respiratory and cardiovascular status.

PPGcare™ alerts a healthcare professional immediately if a patient is trending towards respiratory distress or depression, allowing early intervention to prevent respiratory arrest, and it can discontinue medication infusion until a healthcare professional intervenes.

How it Works

PPGcare™ Technology Utilizes Photoplethysmography (PPG)

PPGcare™ technology utilizes photoplethysmography (PPG), a measurement that can be obtained from pulse oximeters. Instead of using a sensor on an extremity, like a fingertip, the PPGcare™ uses a tiny, comfortable SPOC sensor array that attaches to the ala of the patient (or if the patient is on nasal oxygen, from the nasal septum). Unlike a pulse oximeter located on an extremity, the source of the signal for the PPGcare™ is the arterial plexus (Kiesselbach's plexus on the nasal septum/equivalent on the nasal alae) fed by the last branch of the external and first branch of the internal carotid arteries. The result is a magnitude higher signal with markedly improved signal to noise ratio, and measurement of a wide range of physiologic parameters that are input into proprietary algorithms to provide early warning of respiratory and cardiovascular changes.

From the central alar source, the PPGcare™ provides real-time heart rate, oxygen saturation, respiration rate, respiratory effort, and respiratory obstruction index. The system directly monitors the PD effects of all the factors that may contribute to hypopnea and apnea, and monitors the combined effects of hypoxemia, opioids, other drugs, and the patient's physiological state.

Use in Infusion Pump Monitoring

Introducing PPGcare™

PPGcare™ provides real-time monitoring and assessment of the total pharmacodynamic (PD) impact of drug delivery on the patient's well-being. The system monitors the physiological effects of a patient's drug regimen on their cardiopulmonary status. In addition to the commonly monitored vital signs such as heart rate and oxygen saturation, PPGcare™ measures respiratory rate and analyzes photoplethysmography (PPG) signals for hypopnea, central and obstructive apnea, and trends these values to determine the degree of respiratory depression and respiratory "effort". Because these measurements are obtained from sensors at a "single point of contact" (SPOC) on the nasal ala, surrogates for cerebral blood flow and venous capacitance can be measured. PPGcare™ alerts a healthcare professional immediately if a patient is trending towards respiratory distress or depression, allowing early intervention to prevent respiratory arrest, and it can discontinue medication infusion until a healthcare professional intervenes.

PPGcare™—Complete Pharmacodynamic Monitoring

Today, pulse oximeters are relied upon to provide oxygen saturation and heart rate. But the distal location of the sensors, usually the patient's fingertip, significantly limits the information that can be obtained. While fingertip placement is sufficient for these measurements, the fingertip source is too remote from the carotid artery to provide other valuable information, and peripheral blood flow can be adversely affected by a wide range of medications and physiologic states that make measurements unreliable. Capnography, a mandated safety measure for patients receiving anesthesia, can measure end-tidal carbon dioxide and alert to impending respiratory failure, but is only reliable in intubated patients, and is unsuited for use on general hospital wards. End-tidal carbon dioxide measurements are prone to numerous conditions which can lead to faulty data and interpretation.

From the central alar source, the PPGcare™ provides real-time heart rate, oxygen saturation, respiration rate, respiratory effort, and respiratory obstruction index. The system directly monitors the PD effects of all the factors that may contribute to hypopnea and apnea, and monitors the combined effects of hypoxemia, opioids, other drugs, and the patient's physiological state. PPGcare™ ensures the safest pain medication infusion based on a robust and accurate PD assessment of the patient's respiratory and cardiovascular status.

Opportunities

The Need for New Technology

Infusion pump manufacturers are subject to challenging regulatory pressures, in large part as the result of safety concerns. With the FDA's Infusion Pump Improvement Initiative, focus on the industry will intensify. As Jeffrey Shuren, M.D., director of the FDA's Center for Devices and Radiological Health, said upon the new initiative's announcement, "These pumps often provide critical fluids to high-risk patients, so failures have significant implications. It is time for a more comprehensive approach than we've taken to date." PPGcare™ technology addresses issues discussed in this initiative by introducing a comprehensive level of safety to new and existing infusion pump platforms.

Between 2005 and 2009, 56,000 adverse events involving infusion pumps were reported to the FDA. Pumps can be mis-programmed, malfunction, and not respond to a patient's physiological responses to medications and underlying medical conditions. Whatever the cause, healthcare professionals need an innovative solution that will immediately alert them when dangerous events occur, especially in instances where the patient's medical condition deteriorates rapidly.

An Innovative Solution for Infusion Pump Safety

The PPGcare™ technology is now in a prototype stage, and is being readied for human trials. The first generation is being designed to monitor and alert healthcare professionals before adverse events occur and could automatically slow or stop drug infusion. It could be a stand-alone monitor for any existing infusion pump system, or it could be incorporated into a third party's next-generation infusion pumps.

Later generations of the technology could offer further features in correlating patient vital signs data to pump infusion rates, offering increased patient care and pump safety advancements for the healthcare professional.

Per the present invention, the PPGcare™ is made even more safe by implementation in combination with the present safety system, whereby, in the event that the PPGcare™ detects an adverse subject condition, an appropriate signal is sent to the occlusion device of the present invention and flow of medication to the subject is either completely or partially shut off.

Example 12

Safety Solution for Minimally Sedated Subjects

As noted at the outset of this patent disclosure, to date, no commercially available closed-loop or "advisory" system exists, at least in the United States, for administration of anesthetics (see Sahinovic et al., Current Opinion in Anesthesiology, 2010, 23:734-740). Reproduced below is the American Society of Anesthesiologist's comments to the FDA respecting an Application for Premarket Approval for SEDASYS™ System by Ethicon Endo-Surgery, Inc. Docket No FDA-2009-N-0664; Meeting ID 2009-4438 before FDA's Anesthesiology and Respiratory Therapy Devices Panel of the Medical Devices Advisory Committee, publicly available at http://www.asahq.org/For-Members/Practice-Management/ASA-Practice-Management-Resources/ASA-Regulatory-Comment-Letters/ASA-Comments-to-the-FDA-regarding-SEDASYS.aspx.

Since, in one aspect of the present invention, a system, method and apparatus is provided which addresses the concerns expressed by the ASA before the FDA, in the letter stating concerns below, we comment on how the system, method and apparatus of the present invention addresses the concerns expressed by the ASA. Text of the letter itself is provided below in plain text, while commentary provided thereon by the present applicants is provided in <italicized text between left and right arrowheads>:

On behalf of the American Society of Anesthesiologists (ASA) and its over 43,000 members, whose primary responsibility is the safety of patients under sedation or anesthesia, thank you for the opportunity to comment on the premarket approval application for the SEDASYS™ Computer-Assisted Personalized Sedation System sponsored by Ethicon Endo-Surgery, Inc.

Submitted for premarket approval on Mar. 27, 2008, the SEDASYS device is indicated "for the intravenous administration of 1% (10 milligrams/milliliters) propofol injectable emulsion for the initiation and maintenance of minimal to moderate sedation, as identified by the American Society of Anesthesiologists Continuum of Depth of Sedation, in adult patients (American Society of Anesthesiologists physical status I or II) undergoing colonoscopy and esophagoduodenoscopy procedures."

According to the manufacturer, the SEDASYS™ device has been designed to use patient sensors that measure blood pressure, EKG, hemoglobin oxygen saturation (SpO2), exhaled carbon dioxide levels (ETCO2), and response to verbal commands to control, via computer, the rate of propofol and oxygen administration to patients requiring moderate or "conscious" sedation. While we appreciate the attempts of the manufacturer to incorporate patient respiratory and cardiovascular monitors into the device, we still have several serious concerns regarding the proposed use of SEDASYS™, including:

1. The lack of data to demonstrate the level of safety required of a complex device such as this, which monitors critical life support functions and determines the delivery rate of a potent intravenous anesthetic;

<Naturally, the comprehensive safety solution of the present invention would need to be implemented into a system for minimal sedation and tested in a large trial to address this lack of data comment>

2. The limitations of oxygen saturation (SpO2) and end tidal CO2 (ETCO2) measurements when used for the purpose of detecting respiratory depression in sedated patients;

<It is our contention that by employing PPGcare™, as disclosed herein, (comprising at least the following elements: (i) a CSS PPG monitor, which optionally measures expired CO2, and which can provide supplemental oxygen and positive pressure ventilation (to maintain airway patency, maintain/improve ventilation and ensure adequate blood oxygen saturation) on detection of at least increased respiratory effort, reduced respiration rate, changes in the inspiratory/expiratory ratio [I:E ratio] and/or additional signals indicating hypoventilation, (ii) a means for decreasing or shutting off further infusion of opioid), this basis of expressed concern would be substantially mitigated; the method for detecting breathing problems may employ the signal processing and analysis algorithms disclosed in U.S. Pat. No. 7,785,262; the nasal alar probe may include means for delivery of oxygen, as disclosed in, for example, U.S. Pat. No. 6,909,912; as disclosed herein, utilizing "nasal pillows" to form a tight seal at the nasal passage allows for accurate measurement of NAP and expired CO2 (ETCO2) concentration; permutations and combinations of the elements disclosed in this patent disclosure address this expressed concern of the ASA>

3. The inability of SEDASYS™ to prevent or manage loss of consciousness;

<By including the CSS (actually SPOC) monitoring, which provides the subject with a safety system to ensure that the depth of sedation/anesthesia does not become excessive and cause hypoventilation, that goes unaddressed, while at the same time automatically intervening by, for example, occluding the infusion pump based on PPGcare™ signals indicating respiratory distress, obtundation (reduced level of consciousness/ability to response to stimulation) all ensure that in a quick on and quick off propofol administration regimen, the loss of consciousness is controlled and rendered benign>

4. The properties, inherent risks and current labeling of the anesthetic drug propofol itself; and <Naturally, propofol's inherent pharmacological properties are not altered by the safety solutions disclosed herein, but the safety solutions disclosed herein substantially diminish the danger of using this agent; in addition, in one embodiment according to this invention, a breath-based, expired-propofol concentration sensor, as disclosed in U.S. Pat. Nos. 7,104,963; 6,981,947; U.S. Ser. No. 11/512,856 and incorporated here by reference, is included, which provides a reading of the free blood propofol concentration which provides a separate means for controlling the propofol infusion in detection of a free blood propofol concentration which approaches or exceeds a pre-defined limit>

5. Safety requirements for closed loop control devices such as SEDASYS™.

<A significant utility of the PPGcare™ system according to this invention is to provide enhanced safety in a closed loop control system for propofol or other medication infusion>

I. Lack of Safety Data

Our first concern lies with the limited number of published clinical trials that form the basis of the device's safety record. We know of only three published abstracts and one published paper evaluating the SEDASYS™ device. All of these articles have been published by one research group and, with the exception of one abstract, all come from a single institution in the United States and one in Belgium (1, 2, 3, 4). More important, each of these trials report that the complications of hypoxemia, apnea, and over-sedation occurred in a significant number of patients.

<As noted above, the comprehensive safety solution according to this invention addresses and overcomes each of the stated concerns with respect to hypoxemia, apnea, over-sedation by acquisition of CSS signals that indicate these conditions, coupled with measurement by pulse oximetry at the CSS or both the CSS and PSS, oxygen saturation and ETCO2 can be carefully monitored, alarms are initiated, and infusion is reduced or shut off, when respiratory distress, apnea, hypoxemia or over-sedation is detected>

While no "physician intervention" was reported to be required for SEDASYS™ patients in these trials, the studies do not define what constituted a "physician intervention" or the threshold for such an intervention. For instance, would interventions provided by a nurse, such as lifting a patient's jaw, inserting an oral airway or stimulating the patient, qualify as a "physician intervention?" Further, the studies that recorded apneic episodes lasting longer than 30 seconds reported an incidence of 36% (1, 2, 3). Similarly, the studies that recorded hypoxemia, defined as an oxygen saturation less than 90%, found hypoxemia in 5.8% of patients (1, 2, 3), a rate we believe is a high for any anesthetic treatment.

The largest study to date, available only in abstract form (4), reported neither apnea nor hypoxemia independently, but rather reported a composite measure known as the "area under the curve," reflecting the overall duration and severity of hypoxemia for each patient. The significance of the findings regarding "area under the curve" was not discussed or defined in this preliminary abstract, except to say that the "area under the curve" was lower for patients treated with SEDASYS™ than for patients sedated with midazolam combined with fentanyl or meperidine. The authors of this study did not provide reasons for measuring the "area under the curve" rather than the much simpler incidence of hypoxemia. It is apparent, though, that hypoxemia, no matter how it is described, occurred in some patients treated with SEDASYS™ in this series. Further, patients in this series were receiving supplemental oxygen and, as we will discuss later, SpO2 can be a very late and insensitive indicator of hypoventilation in patients receiving oxygen.

<As noted above, the PPGcare™ system, method and device according to this invention addresses and overcomes these dangers by including not only a monitor of respiratory depression, but an immediate means for intervention, namely nasal pillows or other means (e.g., a face or nasal mask) for administration of positive pressure ventilation as soon as bradypnea, increased respiratory effort or apnea or hypoxemia is detected—with diminution and/or termination of sedation as required to secure subject safety>

In summary, hypoxemia, along with apnea and hypoventilation, did occur in a significant percentage of patients in each of the four studies published to support the safety of the device. Moderate sedation (the indication for which SEDASYS™ is being considered) is defined as "a drug-induced depression of consciousness during which patients respond purposefully to verbal commands, either alone or accompanied by light tactile stimulation." However, some patients in each series, and as high as 58% in one series, (1) became unresponsive for at least some time during the procedure, and thus progressed to the states of deep sedation or general anesthesia. Therefore, not only the small number of studies, but the high incidence of apnea and hypoxemia in the existing studies do not adequately support the ability of the device to prevent unconsciousness and cardiorespiratory depression.

<Inclusion of PPGcare™ technology disclosed herein, as discussed above, addresses each and every one of the above-stated concerns>

II. Limitations of the Oxygen Saturation (SpO2) and End Tidal CO2 (ETCO2) Measurements when Used for the Purpose of Detecting Respiratory Depression in Sedated Patients Propofol, narcotics and other sedative drugs all affect patients' breathing in the same way—by reducing the drive to breathe, causing a decrease in the rate and depth of respiration (hypoventilation). Hypoventilation leads in turn to the accumulation of carbon dioxide and acid in the body, until they eventually rise to levels high enough to depress the heart and brain. The elevation in carbon dioxide, if not detected and readily reversed by ventilatory support, further increases sedation and causes a downward spiral that can ultimately lead to unconsciousness, and in extreme cases, death.

The SEDASYS™ system does indeed measure end-tidal carbon dioxide (ETCO2), an established technique to detect hypoventilation. However, SEDASYS™ uses open nasal cannulae, rather than a closed connection with the lungs, such as an endotracheal tube, as the means to collect the exhaled gas from which carbon dioxide concentration is measured.

<While, of course, use of an endotracheal tube could be used, this is highly invasive and is the reason that the manufacturers of the system in question have not included such an intervention; per the present invention, a minimally or essentially non-invasive solution is provided whereby a closed nasal system is utilized for ETCO2 measurement, and, as appropriate, application of positive pressure ventilation to remove otherwise dangerous buildup of CO2, and, as necessary, provide supplemental oxygen to achieve safe levels of blood oxygen saturation>

A problem with the open nasal cannula technique is that it allows room air to mix with gas exhaled by the patient, often resulting in a falsely low carbon dioxide reading. Further, the accuracy of ETCO2 in the detection of hypoventilation depends on the position of the cannulae, the structure of the patient's nose and mouth, and the patient's individual respiratory pattern (i.e. some patients are primarily nose breathers, some are primarily mouth breathers and some are a combination of both). With this technique, the ability of a computerized ETCO2 monitor to detect hypoventilation is limited by its capacity to only detect slowing or complete cessation of respiration, which are late signs of respiratory depression. Earlier detection depends on a dedicated and experienced health care provider, who understands the limitations of the monitors and who is trained to recognize the patient variables that contribute to respiratory depression and hypoventilation.

<While, of course, the presence of trained personnel would be one solution, the whole purpose of the system in question is to eliminate the need and expense of such personnel being present. The present PPGcare™ system detects hypoventilation and hypoxemia in real time by signal processing of the CSS signal, which, as demonstrated in at least U.S. Pat. No. 7,785,262, provides an early and reliable means for detection of hypoventilation, permitting appropriate alarming of trained personnel, and/or implementation of a safety routine in which the immediate cause of danger is addressed by providing positive pressure ventilation and, if need be reduction and/or cessation of the drug delivery>

The second respiratory monitor used by SEDASYS™ is the pulse oximeter, although it does not measure ventilation or breathing directly. Instead, it measures one of the changes that can accompany hypoventilation which is a reduction of oxygen that is brought into the lung. Reduced ventilation, caused by the patient being sedated, brings insufficient oxygen into the lungs to supply the blood, especially in patients with any pre-existing compromise in lung function. When patients are breathing room air, hypoventilation causes a rapid drop in the SpO 2, which can be measured by the pulse oximeter. This early drop in SpO2, in patients breathing room air, can alert physicians quickly to hypoventilation. For example, Vargo et al. (5) found that 50% of the episodes of apnea or disordered breathing were detected by SpO2 monitoring during upper endoscopic procedures. In their protocol, room air was used until the oxygen saturation fell, to maximize the chances for detection of hypoventilation.

However, when a patient is receiving supplemental oxygen, as in those treated with SEDASYS™, even reduced ventilation can bring enough of the more concentrated oxygen into the lungs to prevent a decrease in blood oxygen concentration or SpO2. Fu et al. (6) demonstrated that the use of supplemental oxygen removes the ability of pulse oximetry to detect hypoventilation. After breathing at half the normal rate of ventilation, fifty percent of Fu's patients who breathed room air had an oxygen saturation of less than 90%. However, almost all of Fu's patients who received supplemental oxygen, even at inspired oxygen concentrations as low as 25-30%, maintained oxygen saturations greater than 90% after ten minutes of hypoventilation. Furthermore, the combination of hypoventilation and supplemental oxygen can cause the level of carbon dioxide and acid in the blood to rise to dangerous levels without a change in the oximeter reading. Davidson (7) reported profound hypoventilation with an arterial carbon dioxide level (PaCO2) rising to 281 mmHg (normal of 40 mmHg) despite an oxygen saturation of 95% as measured by pulse oximetry in a sedated, spontaneously breathing patient receiving oxygen. It is clear that the monitors used by the SEDASYS™ system, such as pulse oximeter and ETCO2, have limitations and must be interpreted in context by experienced individuals with adequate training.

<Once again, PPGcare™ according to this invention provides the solution to the above expressed concerns. By utilizing CSS PPG, the reliance on pulse oximetry to detect hypoventilation is eliminated, as is the danger of missing the hypoventilation by virtue of the conflation caused by supplemental oxygen confounding the oximeter's ability to detect dropping hemoglobin oxygen saturation due to the use of supplemental oxygen. Only on detection of an adverse breathing indication, such as increased breathing effort or reduced respiratory rate, does the PPGcare™ system of the present invention supply supplemental oxygen, thereby retrieving the value of the pulse oximetry technology without putting the subject at risk—which is the intent of providing supplemental oxygen in the existing practice as pointed out in the ASA comments, which, in fact, is precisely what puts the patient's hypoventilation at risk of not being detected in the system absent PPGcare™>

III. The Inability of SEDASYS™ to Prevent or Manage Loss of Consciousness

What would appear to be the SEDASYS™ device's most reliable monitor is the patient's ability to purposefully respond to the device's verbal or tactile commands by pushing a button. However, this monitor is limited to the device's proposed use—the administration of minimal and moderate sedation, during which patients can reliably and purposefully respond to verbal stimulation. In current practice in the United States, many patients undergoing endoscopic procedures require, or at least desire, deeper levels of sedation than SEDASYS™ is designed to administer. It is not always possible to predict this need for deeper sedation before the procedure begins. Dr. Zuccaro describes this in his editorial published in *Gastrointestinal Endoscopy* in 2006: "there is no question that many patients undergoing endoscopy, particularly for long or complex procedures, are deeply sedated at some point during the procedure. This is in part driven by the patient, who often expects or demands a painless experience. Because sedation is a continuum, increasing the frequency of deep sedation logically increases the frequency of inadequate ventilation or airway obstruction." (8)

Further, propofol provides excellent sedation but is poor at relieving anxiety or pain. Withdrawal responses during colonoscopy and cough during EGD, in the opinion of Rex and VanNatta (9, 10), makes moderate sedation, using propofol alone, inadequate for both the patient and the endoscopist. These authors (10) conclude that propofol combined with other agents, can be used effectively to provide moderate sedation, but that "propofol as a single agent is ineffective for targeting moderate sedation for endoscopic procedures."

The limited anxiolytic and [particularly limited] analgesic effects of propofol explain why many of the studies evaluating SEDASYS™ (1, 2, 3, 4), and the use of propofol sedation during endoscopy without SEDASYS™ (10, 11, 12), [frequently] include [the co-]administration of [propofol with] narcotics or benzodiazepines. However, both the sedative effects and the respiratory depressant effects of these agents are additive with propofol. Therefore, co-administration of other agents, especially during the propofol infusion itself, can easily render ineffective the limitations placed by SEDASYS™ on the administration of propofol. In daily clinical practice, SEDASYS™ will frequently be used to administer propofol along with the simultaneous administration of other sedatives and analgesics by practitioners to provide the desired relief of anxiety and pain. This may explain why the four manufacturer-sponsored studies of SEDASYS™ found some patients in each trial whose sedation was deeper than intended, and in one study (1) found that 58% of patients became unresponsive.

<Per the present PPGcare™ system of this invention, even if a subject does descend into a deeper state of sedation or unconsciousness than is intended, the subject is saved from risk by inclusion of one or more of the following elements of the system, as disclosed herein: (i) inclusion of CSS PPG for extraction, processing and evaluation of the vascular impedance signal which includes information on breathing effort, breathing rate and other parameters; (ii) a feed of the analyzed CSS PPG signal to an occlusion device to reduce or shut off infusion of propofol or other respiratory depression causing medications—of course, in a dedicated system, the CSS PPG signal can be fed to a dedicated infusion pump which is equipped with hardware/software to accept such incoming signals—but in the absence of a dedicated infusion pump-CSS PPG communication link, the agnostic occlusion solution provides the required safety measure for the subject, and the infusion pump will then alarm medical personnel when it detects that its output has been occluded; (iii) a source of positive pressure ventilation to reverse the negative effects of hypoventilation; (iv) one or more pulse oximeters, which provide readouts of blood oxygen saturation levels which are accurate as there has been no need up to the point of intervention to flush the subject with supplemental oxygen which might mask the hypoventilation, as eloquently noted in the ASA comments to the FDA>

IV. Properties of the Anesthetic Drug Propofol

In an editorial in *Gastrointestinal Endoscopy*, Dr. Iravani, a UCLA anesthesiologist, states succinctly; "one of propofol's attractive features, the quick onset of sedation, could be its downfall: The depth of sedation could change rapidly from moderate sedation to deep sedation or general anesthesia and result in respiratory depression and/or airway obstruction." (13) As ASA indicated in recent comments to the FDA regarding fospropofol, a pro-drug of propofol (see the ASA comments dated Apr. 23, 2008 regarding NDA22-244 fospropofol disodium injection), "propofol is a potent general anesthetic with a very steep dose-response curve."

The FDA has already recognized, as part of the product labeling, that propofol and more recently fospropofol "should be administered only by persons trained in the administration of general anesthesia and not involved in the conduct of the surgical/diagnostic procedure. Patients should be continuously monitored, and facilities for maintenance of a patent airway, artificial ventilation, oxygen enrichment, and circulatory resuscitation must be immediately available." The FDA has maintained this safety standard despite requests from groups advocating for administration of propofol by nurses and physicians without such specialized training. However, recent articles demonstrate that the SEDASYS™ system is being proposed by some as a way to circumvent these established FDA labeling requirements. According to Dr. Pambianco and colleagues, the SEDASYS™ system is "intended to provide endoscopist/nurse teams an "on label" method to administer propofol sedation for colonoscopy and esophagogastroduodenoscopy." (4) This position is being advanced even though the incidence of deep sedation and hypoxemia reported with SEDASYS™ is no lower, and sometimes higher, than that reported in the past with propofol administered directly by registered nurses and endoscopists (10, 11) without the use of the device. Published studies demonstrate that the device offers little, if any, additional safety benefit, and no reason for the FDA to change its well-established labeling requirements for propofol with or without the use of SEDASYS™.

<Because of the comprehensive safety solution provided by the present PPGcare™ system of this invention, it is anticipated that in an advisory capacity, the PPGcare™ system would in fact provide those skilled personnel in the medical procedure suite with additional safety information that they are not receiving currently, whether the system at issue in the ASA's comments is present or not. If that system were being used, the safety solutions provided by PPGcare™ would substantially enhance its safety profile and, in time, as the safety profile is proven by extensive testing, it is anticipated that these concerns by the ASA could be substantially diffused>

Because of the variability of individual patient response to a given drug, especially a potent one, no electronic or mechanical device used to administer propofol can be expected to prevent adverse reactions entirely, and no device can substitute for the important requirement of human oversight.

<While the present applicants do not disagree that human oversight is desirable, it is believed that the safety solutions provided herein by PPGcare™ would enhance the subject's safety, including when trained personnel are present, and, certainly, if trained, dedicated personnel are not present, the implementation of the safety solutions provided herein would be absolutely critical; because the safety solutions disclosed herein are substantially agnostic with respect to the input medication or infusate, that is, the combined physiological output from medical intervention and underlying clinical condition is being measured, it is in fact possible that in time, the ASA will reconsider whether, even given the individual responses they note above, a system including PPGcare™ is not safer than human oversight in the absence of the present system>

All the published trials of the SEDASYS™ system have reported the occurrence of unintended deep sedation. Under deep sedation or general anesthesia, patients may face several life threatening complications including airway occlusion, apnea, hypoxia, and cardiovascular collapse. Individuals not trained and experienced in the administration of general anesthesia may not be able to restore breathing or normal cardiac activity in time to prevent patient injury. This scenario is even more concerning if the physician responsible for detecting and treating complications of sedation has their attention directed to performing the procedure.

<Because PPGcare™ as disclosed herein is a dedicated system for enhancing safety, and because, in at least one iteration, the PPGcare™ system has in-place the life support systems need to avert trauma to the subject undergoing either minimal or deep sedation, properly trained personnel present in the treatment suite are immediately alerted when the subject experiences hypoventilatory complications, the initiation of measures to address the hypoventilation (administration of positive pressure ventilation and, if necessary, diminution or cessation of drug administration), the PPGcare™ system provides a surrogate for precisely the type of oversight that the ASA is calling for, and enhances the safety of the considered procedures, whether dedicated anesthesiologists are present or not and whether the patient succumbs to total or only partial sedation or anesthesia, or not>

There are no reversal agents available for propofol, should too much of the drug be given or other complications arise.

<There is, however, PPGcare™, as disclosed herein, which, while not reversing the PD or PK effects of propofol, provides the support necessary so that propofol or any other drug administered or combined with propofol does not do mischief to the subject being treated>

Therefore, the need remains for continuous patient monitoring by a trained and qualified individual without other responsibilities, who can maintain the patient's ventilation and circulation until the drug wears off. We would expect that, as an essential part of a clinical study, such monitoring would be present in the clinical trials that are being submitted to establish the safety of the SEDASYS™ system. We are concerned whether, in the non-controlled clinical setting, patients will continue to receive an equivalent level of medical attention while the SEDASYS™ system is in use.

<As noted above, whether the system at issue in the ASA comments is in use or not, the inclusion of PPGcare™ in the environment would be a desirable safety enhancement as it provides in-place ventilation as needed upon detection of hypoventilation, and reduction or cessation of the agent causing the hypoventilation in the first place; while this may not eliminate the need for trained anesthesiologists to be present in the treatment suite, it should substantially allow those anesthesiologists that are present to multiply their efficacy by being on call in the event that the PPGcare™ system initiates the interventions disclosed herein or even if it is set up to only indicate that intervention is required>

V. Safety Requirements for Closed Loop Controller Devices Such as SEDASYS™

The SEDASYS™ system falls into the class of devices known as Physiologic Closed Loop Controllers (PCLC). The International Electrotechnical Commission/International Standard Organization is drafting comprehensive standards regarding the safe use of PCLC's for medical devices (IEC 60601-1-10 Ed1). Therefore, should the SEDASYS™ system be approved, we assume and hope that it will be required to comply with these standards, once published.

Specifically, these draft standards include requirements for the parameters such as the SpO2, ETCO2, EKG, and propofol infusion value to be displayed by the device, how the device responds to inoperable components (such as the pulse oximeter, capnometer, EKG, or noninvasive blood pressure monitor in the case of the SEDASYS™ system) and information to be included in the PCLC instructions for use.

<Each of these stated safety standards are met by various iterations of the elements intended for inclusion in a given implementation of PPGcare™>

Gillham et al. (14) published a peer-reviewed study of a similar type of closed loop infusion controller, using patient responses to voice commands to determine the appropriate propofol drug level. They studied 20 patients undergoing endoscopic retrograde cannulation of the pancreatic duct (ERCP), a somewhat more invasive procedure than colonoscopy. In these patients, they noted the need for manual override of the device in 4 of their patients, because of inadequate sedation in three patients and confusion in 1 patient. Four additional patients were deemed oversedated during the procedure. Therefore, 40% of their patients either were oversedated, or required manual override of the system for insufficient sedation.

The monitoring aspects of the SEDASYS™ could improve patient care currently available in some settings by using pulse oximetry, end tidal CO2, and patient responsiveness monitoring to alert physicians and nurses to needed changes in sedative dosing during endoscopic procedures.

<PPGcare™ goes much further than these suggestions for improving safety by providing a separate source of information relating to the cardiorespiratory status of the subject which immediately detects hypoventilation or impending hypoventilation, and by providing an in-place solution for providing remedial positive pressure ventilation, rather than depending on the confounding supply of supplemental oxygen throughout the given procedure, which, in fact, renders the pulse oximeter readouts worthless; while PPGcare™ cannot anticipate the varied levels of stimulation, it comes very close to providing real time responses, rather than "after the fact" interventions to prevent hypoxia, apnea or unresponsiveness; PPGcare™ does not need to rescue patients from deeper than intended levels of sedation which, in and of themselves, are not dangerous, provided adequate ventilation is occurring and reduction or termination of the sedative is timely implemented>

However, the computer driven, mechanized drug delivery system can never anticipate the varied levels of stimulation, and can only react "after the fact"; once the patient becomes hypoxic, apneic or unresponsive. And of course, the SEDASYS™ system cannot rescue the patient from deeper levels of sedation. Physicians and nurses with high levels of training and experience in the treatment of patients before, during, and after sedative administration will continue to be required to perform at least the following functions during endoscopy:

1. Patient Selection

A. The identification of patients who will need more sedation than available with the minimal or moderate sedation provided by SEDASYS™;

B. Identification of patients with increased risk of airway obstruction;

C. Identification of patients with increased risk of pulmonary aspiration; and

D. Identification of patients with increased risk of respiratory or cardiovascular depression.

<In fact, PPGcare™ is able to assist trained personnel by predicting certain patient pre-dispositions—see, for example, U.S. Pat. No. 7,785,262, which provides a protocol for testing patient susceptibility to airway obstructions and other forms of respiratory challenge; by including a module in PPGcare™ which implements such pre-procedure screening of subjects, the relevant staff can initiate procedures with enhanced degrees of care if the need for such care is indicated, and can initiate such procedures with enhanced information than is currently available from any system, including that at issue in the reviewed comments of the ASA>

2. Continuous Patient Monitoring

A. The current labeling of propofol includes the precaution that the individual who administers the drug should "not (be) involved in the conduct of the surgical/diagnostic procedure." This reflects the well-established principle that there must be an independent practitioner whose sole responsibility is administering propofol and monitoring the patient to assess the level of consciousness and to identify early signs of hypertension, bradycardia, hypoventilation, apnea, airway obstruction, and/or oxygen desaturation.

B. Organizations that accredit hospitals, ambulatory health facilities and office practices, such as the Joint Commission, the Accreditation Association for Ambulatory Health Care and the American Association for the Accreditation of Ambulatory Surgical Facilities, require the immediate availability of a staff member with documented expertise in airway management and advanced cardiopulmonary resuscitation, as well as immediate access to emergency equipment, during procedures performed with propofol sedation.

C. The presence of an additional practitioner who devotes his or her full attention to monitoring the patient's response to sedative drugs and who is able to accept complete responsibility for sedation provides additional patient benefit because it allows the practitioner conducting the surgical or diagnostic procedure to devote his or her full attention to the procedure.

<Each of the above points is addressed by PPGcare™—it provides additional information not currently available from any source so that dedicated trained personnel can act with increased assurances of the subjects status; in addition, so long as such personnel are available, because of the enhanced safety features provided by PPGcare™, on proper training of personnel who are present, appropriate expertise can be brought in while the system provides ventilatory support as needed;

3. Anticipation of the Level of Stimulation

The level of stimulation associated with each part of the surgical procedure must be assessed before the stimulus occurs, so that the level of the anesthetic or sedative drug can be increased in time to meet the anticipated needs of the surgical procedure or decreased to avoid over-sedation during periods of little stimulation. SEDASYS™ may be able to respond to change in patient stimulation, but it cannot anticipate these changes.

<PPGcare™ can react to changes more quickly than even trained staff, and, in addition, it provides information that assists trained staff to react appropriately>

4. Rescue and the Treatment of Complications

In order to act quickly and effectively to prevent and treat any complications involving the respiratory or cardiovascular systems, personnel must be immediately available who have expertise in the assessment of respiration and circulation disturbances and have documented training and current experience in the management of these disorders.

In summary, the use of potent, rapidly acting general anesthetics, such as propofol and now fospropofol, continues to require patient care by personnel trained in the management of deep sedation and general anesthesia, and not involved in the surgical or diagnostic procedure itself. This remains true even if the intent is to provide minimal to moderate sedation, which we know from the literature may not be sufficient for many patients undergoing endoscopy procedures. A computer-assisted closed loop controller, such as SEDASYS™, cannot substitute adequately for the essential human functions. Therefore, in order to maintain an acceptable level of safety, pre-market approval for the SEDASYS™ system should include:

1. The requirement for trained, certified personnel dedicated to continuous monitoring of the patient and the anesthetic administration, identical to that currently in effect for the administration of propofol and fospropofol, be included in the pre-market approval;
2. Displays on the device to provide to the operator continuous output information from all patient monitors, along with the EKG, capnogram, and pulse oximeter waveforms, as well as propofol and oxygen infusion rates;
3. The activation of audible and visual notifications when the propofol infusion rate is automatically changed by the device;
4. The activation of audible and visual alarms when any of the SEDASYS™ monitors ceases normal function, loses its patient signal, or senses a pre-determined "alarm condition;"
5. Warning labels regarding the potential harmful effects of sedative and analgesics if administered simultaneously with the SEDASYS™ infusion; and
6. More extensive pre- and post-market surveillance to ascertain the safety of the device in the clinical setting.

<The present applicants would, of course, add that inclusion of an appropriate embodiment of the PPGcare™ system of the present patent disclosure would likewise be a desirable, if not essential, addition to any such system>

Thank you for your thoughtful consideration of our comments. If you have any questions or require additional information, please do not hesitate to contact Chip Amoe, J. D., M.P.A, Assistant Director—Federal Affairs, in our ASA Washington Office, (202) 289-2222.

Sincerely,
Roger A. Moore, M.D.
President
American Society of Anesthesiologists

REFERENCES

1. Pambianco D J, McRorie J, Martin J, Poltilove R, Whitten C J: Feasibility assessment of computer assisted personalized sedation: a sedation delivery system to administer propofol for gastrointestinal endoscopy (abstr) *Gastrointestinal Endoscopy.* 2006; 63:AB189.
2. Moerman A, Pambianco D J, McRorie J, Martin J, Struys M: Feasibility Assessment of a sedation delivery system to administer propofol for GI endosopy. *Anesthesiology* 2006; 105:A1586
3. Pambianco D J, Whitten C J, Moerman A, Struys M M, Martin J F: An Assessment of Computer-Assisted Personalized Sedation: a sedation delivery system to administer propofol for gastrointestinal endoscopy. *Gastrointestinal Endoscopy* 2008; 68:542-547.
4. Pambianco D J, Pruitt R E, Hardi R, Weinstein M L, Bray W C, Kodali V P, Vargo J J, Schubert T: A computer-assisted personalized sedation system to administer propofol versus standard-of-care sedation for colonoscopy and esophagogastroduodenoscopy: a 1,000 subject randomized, controlled, multicenter, pivotal trial. *Gastroenterology* 2008; 135:294.

Vargo J J, Zuccaro G, Dumot J A, Conwell D L, Morrow J B, Shay S S: Automated graphic assessment of respiratory activity is superior to pulse oximetry and visual assessment of the detection of early respiratory depression during therapeutic upper endoscopy. *Gastrointestinal Endoscopy* 2002; 55:826-831

Fu E S, Downs J B, Schweiger J W, Miguel R V, Smith R A: Supplemental Oxygen Impairs detection of hypoventilation by pulse oximetry. *Chest* 2004; 126:1552-1558

Davidson J A H, Hosie H E: Limitations of pulse oximetry: respiratory insufficiency—a failure of detection. *British Medical Journal* 1993; 307:372-373

Zuccaro G: Sedation and analgesia for GI endoscopy. *Gastrointestinal Endoscopy* 2006; 63:95-96.

Rex D K: Review article: moderate sedation for endoscopy: sedation regimens for non-anesthesiologists. *Alimentary Pharmacology and Therapeutics* 2006; 24:163-171.

VanNatta M E, Rex, D K: Propofol alone titrated to deep sedation versus propofol in combination with opioids and/or benzodiazepines and titrated to moderate sedation for colonoscopy. *Am J Gastroenterology* 2006; 101:2209-2217

Cohen L B, Hightower C D, Wood D A, Miller K M, Aisenberg J: Moderate level sedation during endoscopy: a prospective study using low-dose propofol, meperidine/fentanyl, and midazolam. 2004; *Gastrointestinal Endoscopy* 58:795-803.

McQuaid K R, Laine L: A systematic review and meta-analysis of randomized, controlled trials of moderate sedation for routine endoscopic procedures. *Gastrointestinal Endoscopy* 2008; 67: 910-923.

Iravani M: On computers, nurses, and propofol: further evidence for the jury. *Gastrointestinal Endoscopy* 2008; 68: 510-512

Gillham M J, Hutchinson R C, Carter R, Kenny G N C: Patient-maintained sedation for ERCP with a target-controlled infusion of propofol: a pilot study. *Gastrointestinal Endoscopy* 2001; 54:14-17.

Example 13

Signal Acquisition, Processing and Statistics

This portion of the disclosure summarizes the results achieved in the development of the Single Point of Contact Diagnostic System (SPCDS, or SPOC). The goal of the project was to develop and validate algorithms to calculate RDI (Respiratory Disturbance Index) for a single point of contact diagnostic system consisting of a nasal pressure sensor and a nasal pulse-oximetry/plethysmography sensor. The following bullets summarize the work described hereinbelow:

Polysomnography (PSG) and photoplethysmography (PPG) data was obtained from 35 subjects and scored manually by a trained research technician. The data on the first 20 subjects will be used as a training set, and the data on the remaining 15 subjects were used as a validation set;

Optionally, a study to collect data on up to 10 subjects with epiglottic catheter as a measure of respiratory effort was included;

Preliminary assessment of the prototype AHI estimator based on new patient data and analysis/integration of appropriate algorithms and analysis is provided summarizing in-sample data;

Statistical Analysis: To determine the accuracy of the SPCDS, RDIs were calculated for each study and compared to manual scoring. Receiver-operator characteristic curves can be constructed for the RDIs calculated to assess the performance of the automated algorithm across the spectrum of SDB severity (RDI cutoffs of 5, 10, 15, 20 and 30 events per hour for defining obstructive sleep apnea). The area under the receiver-operator characteristic curve were calculated for each threshold and reported with the standard error and the limits of the 95% confidence interval. Positive likelihood ratio, negative likelihood ratio, optimum sensitivity and specificity were calculated for each threshold. An epoch by epoch assessment of agreement for the detection of respiratory events was conducted.

The outcome of this work was the development of a prototype algorithm validated on 20 subjects recruited from a sleep lab.

The operation of the prototype was validated using analysis of a 15 patient test set utilizing the statistical methods described above and below.

Synchronization

Precise synchronization is an important prerequisite for accurately analyzing the SPOC data. There are three types of synchronization that we implemented during this project. First, low level synchronization involves the alignment of the pulse-oximetry/photoplethysmography (PPG) data with the polysomnography (PSG) data. Second, to optimally detect events, a portion of the parameters that are delayed indicators of events (e.g. post-event parameters) must be "aligned" with the parameters that are already synchronized with the events. And third, "predicted event to scored event" synchronization to allow for the matching of SPOC-labeled events with manually scored events is necessary to determine sensitivity and specificity values.

Figure 13:
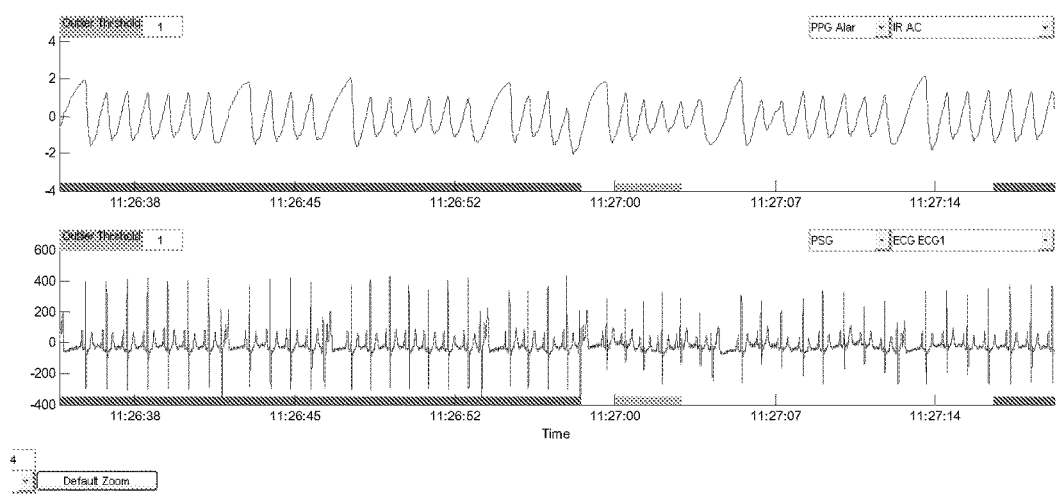
FIG. 13 shows synchronization of PPG and PSG data using a genetic alignment algorithm to optimally match the PPG AC signal with the PSG ECG signal

The accurate synchronization of the PSG and PPG data was a major task. The PSG data is collected via the Alice system and the PPG data is collected using a NICO monitor connected to a PC utilizing a LabView program. The LabView program sends the PPG data along with sync pulses to the Alice system to ensure that the data remains aligned. Unfortunately, the data typically slowly drifted out of alignment, even when using the sync pulses. The sync pulses only ended up providing a rough but inaccurate alignment of the data. We utilized a genetic alignment algorithm to match the two data streams by maximizing the correlation between the ECG channel in the PSG and the AC signal in the PPG. The results for each patient were validated manually and the alignment was determined to be excellent. An example alignment is shown in FIG. 13.

The second synchronization effort is one of aligning parameters that correspond to events with parameters that correspond to post-event phenomena. For instance, the nasal pressure signal drops during an apnea event, but the pleth DC signal drops during the post-event time. In order to maximize the classification capability of these signals, it is desirable to shift the pleth DC signal back in time to be better aligned with the nasal pressure signal. To optimize this process, we determined the maximum area under the curve (AUC) of each parameter's event-prediction ROC curve. We then shifted the parameters and determined the shift that produced the largest AUC (e.g. the best prediction). This synchronization dramatically increased the discrimination provided by these "post-event" parameters.

The third synchronization, aligning the predicted and actual events for sensitivity analysis, will be described in greater detail in the Results section.

Model Optimization

To derive a predictive model, there are multiple levels of optimization that can be utilized. First, individual parameters must be conceived, implemented, evaluated, and optimized. Second, individual parameters must be combined optimally to create the desired model.

The first step in creating a model to detect events is to create appropriate parameters that capture information of interest. We started the project with a literature review and several brain-storming sessions to determine physiologic effects we were hoping to capture mathematically from the data. Once the physiologic effects are identified, parameters are coded and evaluated to determine how well they capture the information intended and how well the information predicts the events. Each physiologic effect (e.g. venous capacitance change, reflected by a change in pleth DC value) may have several possible parameters that attempt to capture its useful information (e.g. area in the DC drop, DC drop depth, DC drop time, etc.) and each parameter may have several sub-parameters that need to be optimized (e.g. window width to determine DC baseline for calculating DC drop). All of these parameters and sub-parameters were optimized using the AUC of an ROC curve generated by separating event breaths from non-event breaths. This AUC methodology allowed us to optimize the individual parameters without having to do end-to-end comparisons of event detection (e.g. event synchronization, RDI calculation, etc.). The AUC methodology provides a method of maximizing each parameter's ability to separate the event vs. non-event distributions.

The physiologic effects we attempted to parameterize were:
Venous Compartmentalization
Rise of DC during events
Fall of DC during arousals
Slope of DC "recovery"
Envelope changes in the BR signal.

Saturation:
  Drop/Rise in $SpO_2$ over IR during event/recovery.
  Desaturation slope
Respiratory System:
  Amplitude of flow and pressure drops/rises during events/arousals.
  Breath Amplitude variability
  Shark fin pattern during early part of occlusion
  Breathing effort pattern from IRDC curve.
Cardiac System:
  HR & HR variability
  AC amplitude and AC amplitude variance
Nervous system:
  HR variability, Breath Rate variability, IR DC variability Because many of the parameters are based on characteristics of breathing, we decided to first parse the data files into breaths to allow for a consistent methodology for parameterization and averaging. Breaths were determined based on the nasal pressure signal. During apneas when the breathing was not easily determined, an average breath rate was utilized to parse the data. The training set was then labeled from the manual scoring table, producing breath-by-breath labeling of the events. Each parameter was then calculated for each breath and the breath-based labeling and parameters were used to calculate ROC curves. Breath-by-breath analysis is not optimal since an event might be 3-5 breaths and a parameter might miss the first and last breath, for instance. This technique, however, does provide a low-complexity methodology for determining the separation provided by the parameters and allows for optimization of the parameters and sub-parameters.

The parameters derived from this analysis consist of:
5 Nasal pressure parameters
6 $SpO_2$ parameters
9 Pleth cardiac parameters
8 Pleth low frequency parameters
3 Pleth breath parameters (bandpass filtered at breath rate)

Figure 14:
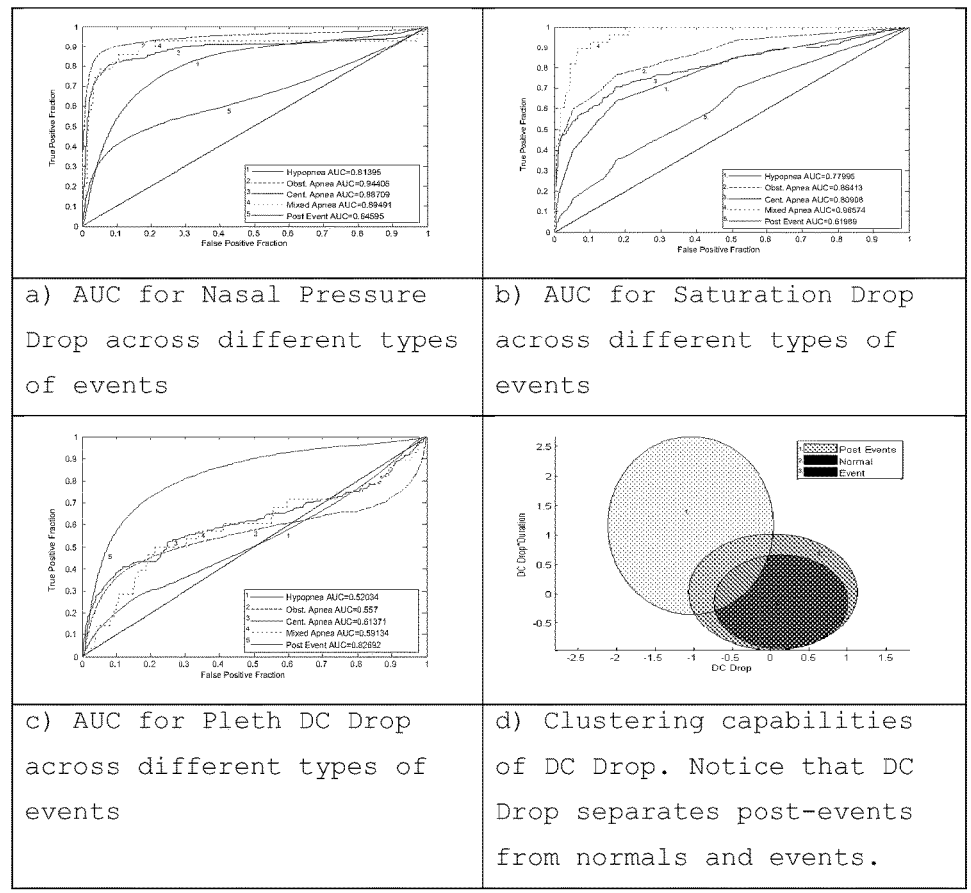
FIG. 14 shows optimization of individual parameters (a) AUC for Nasal Pressure Drop across different types of events; (b) AUC for Saturation Drop across different types of events; (c) AUC for Pleth DC Drop across different types of events; (d) Clustering capabilities of DC Drop. Notice that DC Drop separates post-events from normals and events.

FIG. 14 shows several plots indicating the performance of the individual parameters on breath-by-breath classification.

Once the individual parameters are optimized, the next step is to create multi-parameter models that maximally capture the information and coupling of the individual parameters as well as the temporal structure of the data. An important consideration in multi-parameter modeling is that it is the unique (independent of other parameters already in the model) information that a parameter adds to the model that makes it valuable, not its individual ability to separate the classes. Another important point is that optimization of any model requires good criteria. We determined that the best result is one that maximizes multiple criteria simultaneously: correlation with RDI, Kappa statistic for epoch-by-epoch confusion matrices, and diagnostic agreement. Although this complicates the optimization process, the performance surfaces of the models was not steep or highly non-linear, so optimization of multiple criteria was possible without excessive effort.

To use these statistics for optimization, however, we needed to implement several algorithms to compute them. First, events were predicted by the multi-parameter model and a windowing algorithm was used to modify breath-by-breath events into events similar to those scored manually (e.g. 10 second events, etc.). The RDI was calculated by summing the events and dividing by "valid study time" (note: not sleep time). The epoch-by-epoch confusion matrices were computed by summing the predicted and scored events per 30 second epoch. Diagnostic agreement was also computed based on the ability of the system to accurately predict a range of RDIs (more information in the Results section). Some subtleties exist in these statistics. For instance, high RDI patients will have 1000s of events whereas low RDI patients will have 10s of events. The high RDI patients will therefore dominate the epoch-by-epoch Kappa value.

An important feature of our multi-parameter modelling is the addition of temporal information. Many of the parameters are highly predictive of events, but have a high rate of false positives as well. When analyzing the data however, it is clear that events have a different temporal structure (smooth) than the false alarms (peaky). In addition, some parameters detect events, some parameters predict recovery (or post-events), and some parameters indicate normal breathing. By utilizing a temporal model, additional information about the progression of the signals over time can be utilized to make decisions.

There are many approaches to adding temporal information. The most common approach is averaging which is a subset of moving average filters (finite impulse response filters, or FIRS). Strict averaging multiplies each sample by 1/N (where N is the number of samples in the average) and sums the results. Moving average or FIR filters are similar, except that each sample can have a different weight. This allows the filter to give varying emphasis to different delays or time frames (for instance, more emphasis to the recent past than the distant past). Implementation of this type of filter often includes the concept of a tap-delay line which is a memory structure that stores the recent past of the signal and scales each one to create the model output. We call this approach the TDL (tap-delay line) and use it as our baseline temporal filtering approach.

We also experimented with temporal neural network models and the Hidden Markov Model (HMM). We utilized a tap-delay neural network (TDNN) model which is the most common temporal neural network and is a non-linear generalization of the FIR filter. The HMM provides a state-based (stochastic) approach to extracting temporal information. The HMM creates states based on the inputs to the model and calculates the likelihood that the current set of data was generated by the model. Therefore, an HMM model would be created with apnea events and the data leading up to and following the event. Other HMM models would be created to represent other events or normal breathing. New data is passed through all the models and the model that has the highest probability of matching the data "labels" the data.

In this study, with only 20 patients in the training set, the TDL, TDNN, and HMM models all produced roughly equivalent performance. In modeling theory, the simplest model that has adequate performance is most likely to generalize across new data, particularly with a small training set (increased complexity requires larger training sets to adequately train). For this reason, our analysis focused on the TDL model. Experimentally, 5 memory elements were sufficient to capture the information of interest in the signal. Typically, this memory was centered on the breath of interest, meaning that the memory structure contained the breath under test and the 2 breaths before and after it.

Miscellaneous Analysis
Several side-studies were implemented during the project.
Arousal Detection
One such study looked at the ability of the parameters to determine arousals. In our database, 72% of events have a labeled arousal within 5 seconds after the event. The majority of the remaining 28% appear to have similar characteristics to an arousal in the breathing parameters, but are not labeled as arousals (insufficient EEG activity?). In a quick evaluation of our parameters, we were able to detect these arousals using only DC drop with an AUC of 0.85.

Analysis of Saturation Differences

Another topic of interest was whether the saturation information at the central site was similar in value and discriminability to the saturation at the finger. The three studies were scored, first with the finger saturation and a month later with the nasal alar saturation. The scoring is shown in the table below. We also calculated the epoch-by-epoch confusion matrix and determined that the Kappa statistic for this matrix was 0.92 and had an agreement rate of 98%. The differences in the scoring are similar to if not less than the typical difference in scoring between multiple scorers, and thus considered insignificant.

|  | Finger SpO2 | Alar SpO2 |
| --- | --- | --- |
| SPOC-04 | 36.5 | 36.1 |
| SPOC-06 | 29.1 | 25.2 |
| SPOC-08 | 13.9 | 12.2 |

|  |  | Nasal Alar | | |
| --- | --- | --- | --- | --- |
|  |  | 0 | 1 | 2 |
| Finger | 0 | 2368 | 9 | 0 |
|  | 1 | 51 | 420 | 0 |
|  | 2 | 0 | 0 | 7 |

Next, we evaluated the differences in our models when nasal saturation was replaced by finger saturation. Some caveats of note are that the NICO (alar) reports saturation in increments of 1% whereas the Alice system (finger) reports saturation in increments of 0.1%. When looking for saturation drops of 2-5%, the increased resolution of the Alice system is particularly important. Additionally, the NICO does not seem to handle the increased signal strength of the ear-lobe sensor when attached to the alar. The alar has less flesh and more blood flow than the finger, thus producing a much stronger signal. In our previous studies using the Novametrix Oxypleth, we did not have this problem. The NICO tended to threshold the saturation at 100% and thus produced even less resolution than the finger. It is important to note that this is a data collection limitation, not a physiologic limitation. The following table shows the percent of the time that the saturation at the nasal alar was determined to be 100% (relatively uncommon normally).

| Patient | Total Clipped Time (hrs) | Total Record Time (hrs) | % Time Clipped |
| --- | --- | --- | --- |
| SPOC-01 | 3.58 | 8.75 | 40.9% |
| SPOC-02 | 5.69 | 8.77 | 64.8% |
| SPOC-03 | 2.85 | 3.37 | 84.4% |
| SPOC-04 | 0.27 | 7.40 | 3.7% |
| SPOC-05 | 0.00 | 6.76 | 0.0% |
| SPOC-06 | 0.35 | 7.80 | 4.5% |
| SPOC-07 | 1.64 | 6.62 | 24.8% |
| SPOC-08 | 0.26 | 8.79 | 3.0% |
| SPOC-09 | 0.42 | 7.21 | 5.8% |
| SPOC-10 | 0.73 | 6.06 | 12.1% |
| SPOC-11 | 0.02 | 7.70 | 0.2% |
| SPOC-12 | 7.64 | 7.83 | 97.7% |
| SPOC-13 | 4.35 | 7.53 | 57.8% |
| SPOC-14 | 3.40 | 7.85 | 43.3% |
| SPOC-16 | 1.14 | 7.86 | 14.5% |
| SPOC-17 | 0.09 | 7.20 | 1.2% |
| SPOC-18 | 0.01 | 6.91 | 0.1% |
| SPOC-19 | 4.81 | 7.34 | 65.6% |
| SPOC-20 | 0.02 | 6.40 | 0.3% |
| SPOC-21 | 0.01 | 6.23 | 0.2% |
| SPOC-22 | 2.93 | 7.79 | 37.6% |
| SPOC-23 | 4.77 | 7.96 | 59.9% |
| SPOC-24 | 1.01 | 5.34 | 18.9% |
| SPOC-25 | 0.00 | 7.13 | 0.0% |
| SPOC-26 | 0.07 | 2.96 | 2.3% |
| SPOC-27 | 2.76 | 7.07 | 39.0% |
| SPOC-28 | 1.37 | 8.49 | 16.2% |
| SPOC-29 | 0.32 | 6.52 | 4.9% |
| SPOC-30 | 1.00 | 6.43 | 15.5% |
| SPOC-31 | 1.28 | 6.64 | 19.2% |
| SPOC-33 | 0.06 | 6.63 | 0.9% |
| SPOC-34 | 0.07 | 7.56 | 0.9% |
| SPOC-35 | 0.71 | 7.35 | 9.6% |
| SPOC-36 | 0.94 | 5.20 | 18.1% |
| SPOC-37 | 3.14 | 7.26 | 43.3% |

When comparing nasal alar saturation and finger saturation, we found that the average saturation drop during events with the nasal alar was 2.5±1.8 and with the finger 2.8±2.1. When analyzing the delays in the signals by calculating the optimal time-shift to align the saturation drop with the event window, the finger saturation delay was 7.5 seconds and the nasal alar delay was 5 seconds. Theoretically, central sites may desaturate faster than peripheral sites, although this cannot be strictly proved with this data due to differences in the data acquisition of the finger (Alice) and alar (NICO). Lastly, we calculated the ROC curves for detection of events with the nasal and finger saturation. FIG. 14(b) shows that these two ROC curves are virtually identical. Thus, although the saturation signals were collected differently and were suboptimal at the nasal alar, the information content of both signals was equivalent. Oxygen Desaturation Index To further analyze the differences in saturation, and also create baseline model statistics, we endeavored to automatically calculate the manual scoring oxygenation desaturation indices (ODIs) from the PSG and PPG data. In the patient reports, the Desat Index is simply given as "#/hr", with no further explanation of how it is calculated. We assumed they used a 3% cutoff to get the number of Desats (#) and that they divided by Time in Bed (TIB), but we don't know if these assumptions are correct.

For our calculations, the Desaturation Index is equal to the number of times the $SpO_2$ value falls below a cutoff value (relative to a baseline) divided by the time in bed (TIB). For both the predicted alar-based (PPG) and finger-based (PSG) desaturation indices, we evaluated a variety of $SpO_2$ cutoff values to determine which one most closely matched the manually scored Desaturation Index as well as dividing by both TIB and total sleep time (TST). The TIB is the time from Light Off to Light On and TIB is equal to the TST plus the times labeled WK. We optimized these parameters by minimizing the mean squared error (MSE) between the predicted ODI and the manually scored ODI. It turns out that using the PSG $SPO_2$ to predict scoring (optimal possible solution), a cutoff of 3.5% and TIB gave the lowest MSE. Except for 3 patients, the difference between Total Recording time and TIB is less than 30 minutes.

From this optimization, we calculated 3 sets of Desat Indices:

Using the PSG signal, we calculated Desat Index=# of Desats/TIB (Column C) using a cutoff of 3.5%.

Using the PPG signal, we calculated Desat Index=# Desats/TIB (Column D) using a cutoff of 3.01%.

Using the PPG signal, we calculated Desat Index=# Desats/Total Recording Time (Column E) using a cutoff of 3.01%.

The results are shown in the table below. We also calculated the mean squared error without patients 16 and 18. Because these two patients have large Desat Index values, they also have larger absolute error values and have a disproportionate effect on the MSE value ($L_2$ and high norms emphasize larger errors more than smaller errors). We thought it would be helpful to look at the MSE without these two patients included. The table shows MSE with and without those two patients.

| | | Column C | Column D | Column E |
|---|---|---|---|---|
| | | | Calculated Desat Index | |
| Column A Patient (SPOC)# | Column B Given Desat Index (PSG) | PSG cutoff = 3.5%/TIB | PSG cutoff = 3.01%/TIB | PSG cutoff = 3.01%/Rectime |
| 1 | 7.4 | 7.3 | 9.0 | 9.2 |
| 2 | 3.6 | 7.2 | 4.0 | 4.2 |
| 3 | 4.7 | 2.4 | 0.9 | 0.9 |
| 4 | 14.5 | 15.6 | 15.8 | 15.5 |
| 6 | 17.9 | 20.5 | 15.9 | 16.5 |
| 8 | 7.4 | 10.4 | 7.8 | 7.5 |
| 9 | 8.9 | 6.4 | 15.5 | 15.1 |
| 11 | 1.3 | 0.0 | 0.0 | 3.8 |
| 12 | 0.1 | 0.2 | 0.0 | 0.0 |
| 13 | 7.1 | 7.1 | 5.2 | 5.0 |
| 14 | 10.1 | 9.0 | 8.9 | 8.6 |
| 16 | 94.1 | 88.0 | 80.1 | 77.1 |
| 17 | 0.6 | 2.2 | 1.6 | 1.5 |
| 18 | 39.8 | 42.1 | 33.8 | 31.4 |
| 19 | 5.1 | 3.5 | 1.0 | 0.9 |
| 20 | 20.2 | 14.8 | 14.8 | 13.9 |
| 21 | 2.0 | 7.0 | 6.2 | 3.5 |
| Mean | 14.4 | 14.3 | 13.0 | 12.6 |
| Std. Dev. | 22.7 | 21.5 | 19.3 | 18.4 |
| MSE* | 0 | 8.6 | 21.8 | 29.0 |
| MSE: no 16&18** | 0 | 7.0 | 9.2 | 8.8 |

*MSE: Mean Squared Error between values in column and Given Desat Index (Column B)
**MSE no 16&18: Mean Square Error not including patients 16 and 18 (patients with very high index values)

Figure 15:
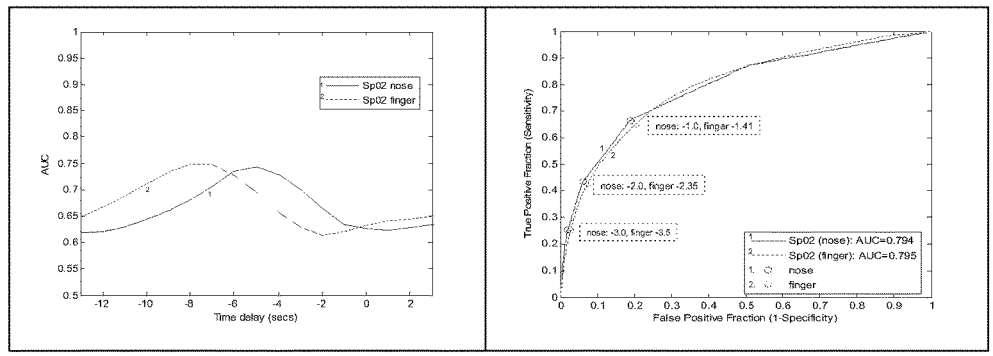
FIG. 15 shows saturation differences between a PPG probe placed at a Central Source Site (CSS), in this case, a nasal alar site, as compared with a Peripheral Source/Sensing Site (PSS), in this case, a finger, showing, in (a) optimal time shifts between finger and alar saturation and in (b) ROC curve of event prediction using finger and alar saturations.
Figure 16:
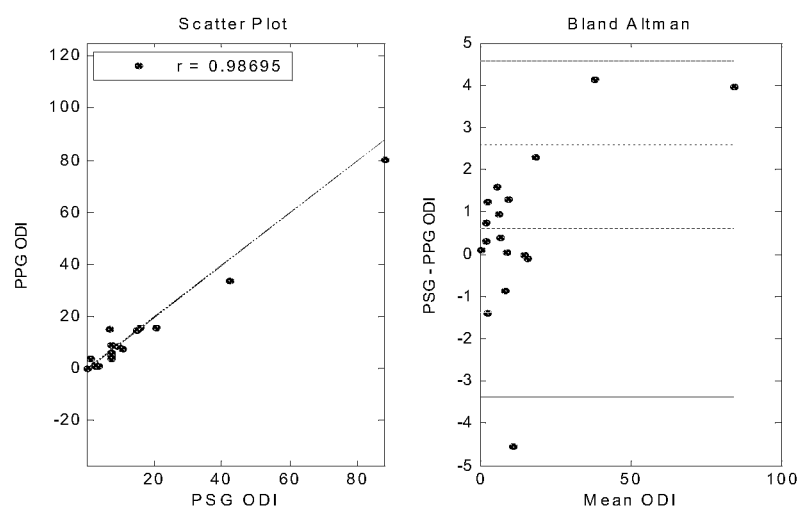
FIG. 16 shows correlation and Bland Altman for nasal (PPG) vs. finger (PSG) ODI

FIG. 15 shows the excellent correlation between the ODI calculated with the nasal probe and the ODI calculated with the finger probe. The correlation coefficient is 0.987 and the bias is 0.7 with a precision of 2.

Classification of Central vs. Obstructive Apnea

We also implemented a short study to determine the ability of the current SPOC data to predict the difference between central and obstructive apneas. In particular, we studied the EPISPOC patients since the epiglottal catheter allows for more "scientific" scoring of obstructive, central, and mixed apneas. At the time this study was done, 4 EPISPOC patients were available (102-105). The study utilized a new parameter called BR Energy to classify. BR Energy estimates the breath effort by summing the energy (square of BR signal) over a 10-second window and dividing by the average energy over a 300-second baseline window. This methodology determines changes in breathing effort. The tables below summarize the performance of the model to detect the difference between central and obstructive apnea and also the difference between central and mixed versus obstructive apnea. Agreement rates are good and the Kappa statistic indicates "moderate agreement" between the PSG and predicted labeling.

| Central vs. Obstructive | | | |
|---|---|---|---|
| | | CE System | |
| | | Central | Obst |
| PSG | Central | 40 | 39 |
| | Obst | 28 | 465 |
| PSG | Central | 7.0% | 6.8% |
| | Obst | 4.9% | 81.3% |

Kappa = 0.48, Agreement = 88%

| Central and Mixed vs. Obstructive | | | |
|---|---|---|---|
| | | CE System | |
| | | Cen/Mix | Obst |
| PSG | Cen/Mix | 256 | 94 |
| | Obst | 135 | 358 |
| | | CE Systsm | |
| | | Central | Obst |
| PSG | Central | 30.4% | 11.2% |
| | Obst | 16.0% | 42.5% |

Kappa = 0.48, Agreement = 73%

The Model and Training Set Analysis

The final SPOC model evolved over time, to include the following parameters:

Nasal pressure drop: for each breath, the percent change in amplitude from baseline is computed. The signal is filtered to remove high-frequency spikes and outliers, and the nasal pressure drop is computed as the difference between the baseline peak amplitude minus the maximum peak amplitude during the breath. For stable breathing, the baseline peak amplitude is the average of peak amplitude over a 40-breath window centered on the breath of interest. For unstable breathing (e.g. during periods of many events), the baseline peak amplitude is the mean of the largest 50% of the peaks in that window.

$SpO_2$ drop: for each breath, $SpO_2$ Drop is computed as the mean of the $SpO_2$ during that breath subtracted from baseline. The baseline $SpO_2$ is calculated as the modified median of the $SpO_2$ in the two minute window centered on the current breath, where the modified median is the $80^{th}$ percentile value of the sorted breaths in that window.

Pleth DC drop area: for each breath, DC Drop Area is the integral of the portion of the DC signal that drops 1% or more below the baseline. The AC and DC signals are separated using the patented algorithm to optimally separate the cardiac signals from the respiratory and other signals. The baseline is computed as the average of the DC signal in a five-minute window centered on the breath of interest.

Pleth heart rate: for each breath, the pleth cardiac signal is parsed for peaks and the heart rate is determined by counting the peaks in the preceding 10 seconds.

Each of these parameters is time shifted (when necessary) and weighted using a five-tap delay line (TDL model) to create a single signal that indicates events. An optimal threshold is then determined to detect events. The events are then utilized to calculate RDI, the epoch-by-epoch Kappa statistic, and diagnostic agreement.

Figure 17:
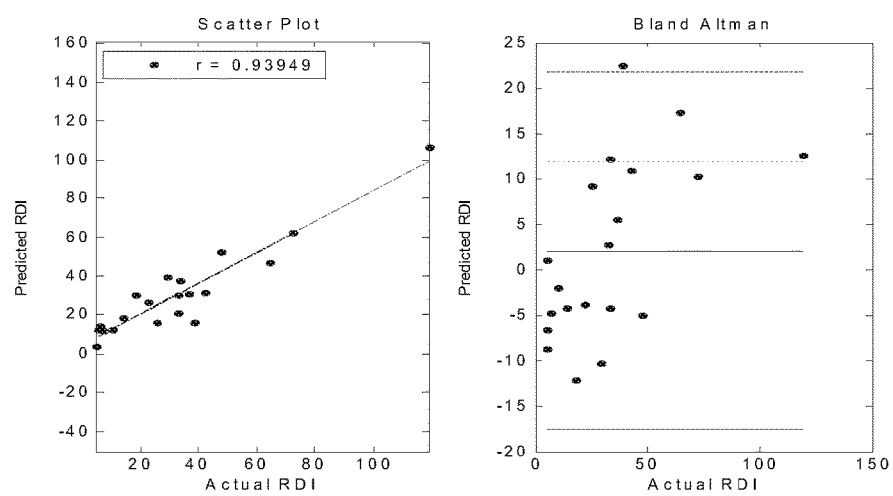
FIG. 17 shows correlation between SPOC model and scored RDI

Performance of this model was good as shown in FIG. 17; it is noted that the models must be scaled to correlate well with RDI, rather than actually determining the actual value of RDI. The model may be improved through evaluation of robustness and routine experimentation.

We not only created a new model that matched RDI without scaling, we also did a series of tests on the models to determine their "robustness" and ability to generalize outside of the training set. The resulting new model performs well on mean RDI error (mean absolute error of 8.9, dominated by the large RDI patients), diagnostic agreement (95%), and the Kappa statistic of the confusion matrix (0.465). The new model replaced the "Pleth DC Drop Area" parameter with the similar "Pleth IR DC Drop" parameter and replaced the "Pleth heart rate" parameter with the "Pleth Red AC Amplitude Variance" parameter.

Pleth IR DC Drop: for each breath, the IR DC Drop is calculated as the ratio between the average IR DC value during the breath and the baseline IR DC value. The baseline IR DC value is an average of the IR DC value over a 40-second window centered on the current breath.

Pleth Red AC Amplitude Variance: for each breath, the Pleth Red AC Amplitude Variance is calculated as the variance of the peak-to-trough distances of all beats detected in the breath and 10 seconds prior to the breath.

Figure 18:
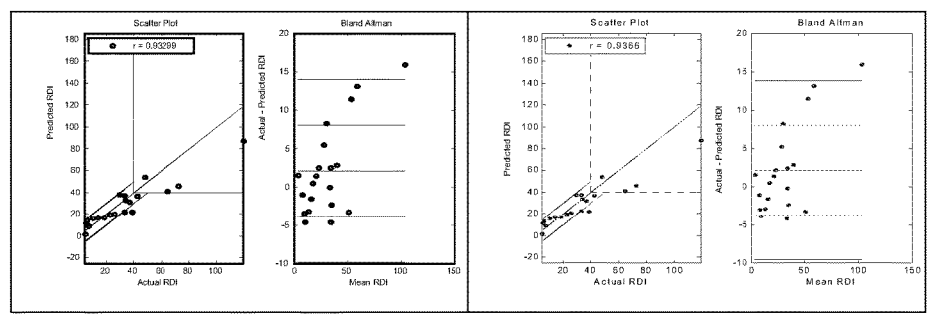
FIG. 18 shows leave-one-out performance for final model, (a) Correlation of predicted versus actual RDI using leave-one out performance. r=0.933; (b) Correlation of predicted versus actual RDI using all 15 patients in training set. r=0.937.

Model robustness was evaluated using the leave-one-out and leave-five-out techniques. In the leave-one-out method, 15 different models were created with only 14 of the 15 patients with RDI<40. Each model was used to only predict the RDI for the one patient not included in the training set. The final evaluation is determined by calculating statistics for the 15 different models on each of the "left out" patients. As shown in FIG. 18, performance of the model during the leave-one-out testing was nearly identical to the performance of the model using all 15 patients as the training and testing sets. This indicates that the model is robust across all 15 patients used in this study.

Figure 19:
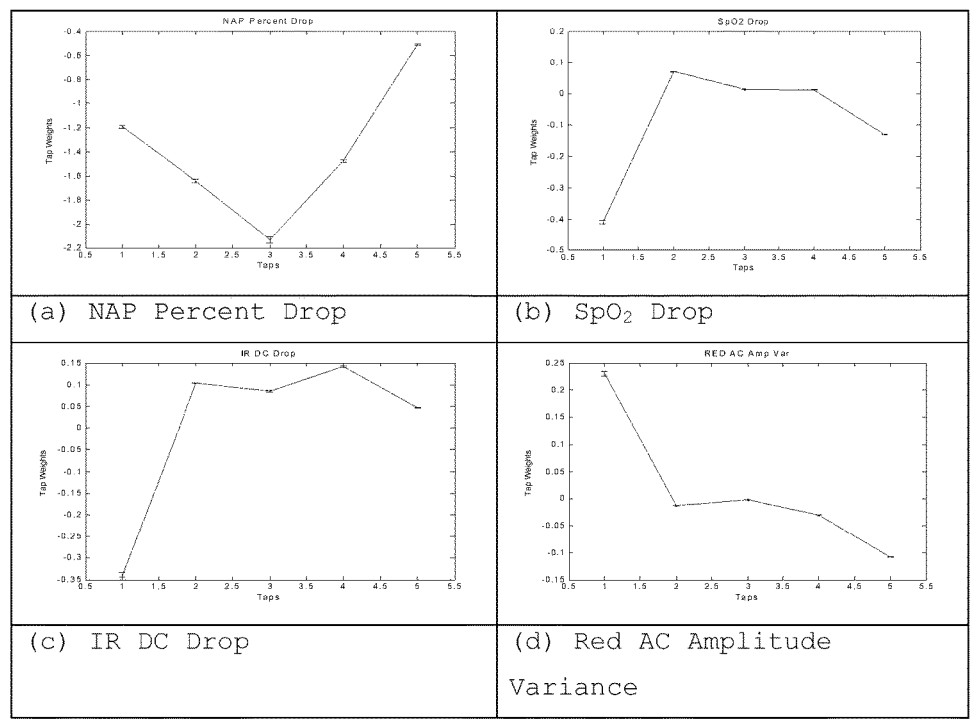
FIG. 19 shows amplitude and variance of weights derived from leave-five-out analysis.

To further test the robustness of this new model, we implemented a leave-five-out methodology that utilizes only 10 patient databases for training. This is a more difficult task since the training set is smaller. Performance was similar to above again proving successful generalization. We also analyzed the variance of the weights in the model. A good model will have very similar weights when trained on different data sets—this indicates that the model is not sensitive to the choice of training set and is capturing the information of interest. FIG. 19 shows the weights for each of the 5 taps of the TDL for each parameter in the final model. In particular, notice the variance bars for each weight and how small the variance is between the 50 random selections of 10 patients. This is an excellent indication that the models are robust to patient selection.

Our last sanity check to ensure we have a robust model is to utilize the EPISPOC patients as an independent test set. Using the 15 patients with RDI<40 as the training set and the 4 good EPISPOC patients as the test set, we achieved a correlation coefficient of 0.99 and a 100% diagnostic agreement. The table below shows the predicted and actual RDIs for these patients.

|  | PSG RDI | SPOC RDI |
|---|---|---|
| EPISPOC-102 | 48.4 | 53.2 |
| EPISPOC-103 | 42.2 | 51.1 |
| EPISPOC-104 | 70.2 | 75.9 |
| EPISPOC-105 | 47.5 | 53.6 |

In summary, all indications are that this model should generalize well to new data, under the following assumptions: (1) The training data represents the population of interest well, and (2) the test data comes from the same population as the training data.

Further Model Evaluation

Figure 20:
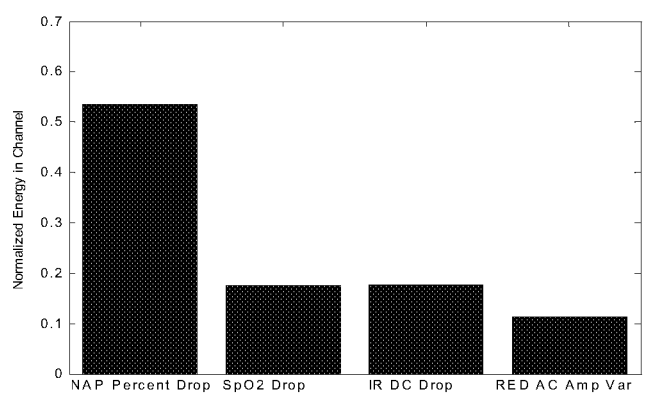
FIG. 20 shows the contribution of each channel to the model's output.

It is desirable to understand the amount of information from each parameter that is utilized by the model. To do this, the energy in each of the four channels was summed across the 20 patients and the four parameters were then normalized to sum to 1. FIG. 20 shows the contribution from each channel in the model's output. As expected, nasal pressure has the largest single contribution to the model at ~50%, with the other three parameters contributing between 10% and 18%.

Further analysis shows that the largest errors in the prediction of the RDI arise from patients who have a significant difference between sleep time and study time. The table below shows that the two patients who fell outside the White/Westbrook diagnostic agreement both had significant wake times during the study. The current SPOC model does not have the capability to compute sleep time and therefore assumes the patient is asleep during the entire study.

|  | PSG RDI | SPOC RDI | TST Over-Prediction (hrs) |
|---|---|---|---|
| SPOC-01 | 33.2 | 21.8 | 4.3 |
| SPOC-02 | 10.2 | 14.9 | 0.9 |
| SPOC-03 | 18 | 16.1 | −1.6 |
| SPOC-04 | 36.5 | 33.1 | 2.3 |
| SPOC-05 | 5.3 | 11.6 | 2.3 |
| SPOC-06 | 29.1 | 38.1 | 1.1 |
| SPOC-07 | 25.2 | 20.9 | 1.0 |
| SPOC-08 | 13.9 | 17.1 | 1.2 |
| SPOC-09 | 32.6 | 36.0 | 1.2 |
| SPOC-10 | 47.5 | 53.0 | 0.3 |
| SPOC-11 | 5.5 | 13.4 | 0.9 |
| SPOC-12 | 4.8 | 1.6 | 2.8 |
| SPOC-13 | 33.3 | 34.4 | 1.5 |
| SPOC-14 | 42.4 | 37.9 | 1.5 |
| SPOC-16 | 119 | 92.1 | 0.5 |
| SPOC-17 | 6.9 | 9.7 | 0.6 |
| SPOC-18 | 72.1 | 49.1 | 1.0 |
| SPOC-19 | 22.2 | 21.3 | 0.6 |
| SPOC-20 | 64.3 | 43.3 | 2.0 |
| SPOC-21 | 38.3 | 22.1 | 3.5 |

* RED Patients fell outside White/Westbrook Agreement Boundaries

Pleth Only Model

Since the Nasal Pressure is the major contributor to the model, we decided to evaluate the performance of a pleth only model (e.g. using data only from the pulse-oximeter). The best model parameters were:

$SpO_2$ Drop: discussed earlier

IR BE Energy: Breath effort signal as defined in the obstructive/central apnea section.

RED DC Drop Area: The area of the DC drop in the RED signal relative to a baseline. The baseline is as computed in the same way as in previous similar parameters.

Pleth Red AC HR Variability: the variability of heart rate measured in a 10 second window preceding the current breath.

Figure 21:
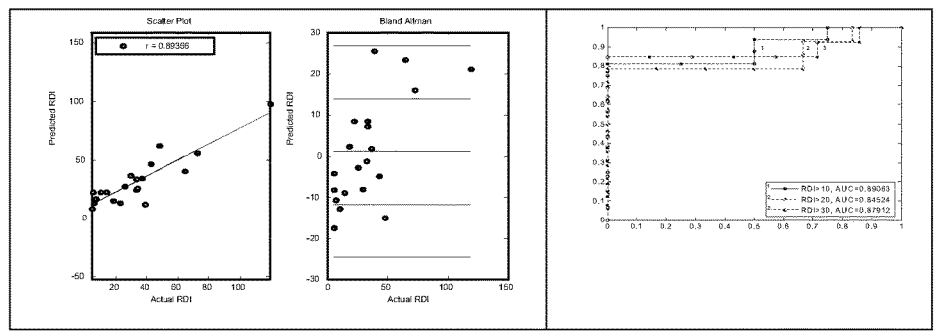
FIG. 21 shows the performance of a pleth-only model: (a) Correlation plot and Bland Altman; (b) ROC curves for RDI>10, 20, 30

This model performed well, but not as well as the model that also included nasal pressure. FIG. 21(a) shows the correlation plot for RDI with a correlation coefficient of 0.894, with a bias of approximately 1 RDI point and precision of approximately 10. The ROC curves showed an AUC between 0.84 and 0.89 for the RDI>10, 20, 30 predictions.

Statistical Analysis Techniques

This section will summarize the rules and techniques we used to calculate the various statistics used during this project.

Sensitivity Analysis

For sensitivity analysis, events needed to be matched between the manual and predicted scoring. This matching then results in the labeling of events as true positive, false positive, and false negative (true negatives are ill-defined). The following rules (consistent with those used in De Almeida, et. al. "Nasal pressure recordings to detect obstructive sleep apnea", Sleep Breath 2006 10(2):62-69) were applied for aligning and matching events:

The time at the center of each event, both manually scored and predicted, was used for alignment.

If a predicted event occurred within 10 seconds of an actual event, it was scored a true positive.

False negative events were those that were manually scored as an event without a predicted event within 10 seconds.

False positive events are when a predicted event was not within 10 seconds of a manually scored event.

If two predicted events occurred within 10 seconds of an actual event, one was scored a true positive, the other a false positive.

White/Westbrook Diagnostic Agreement

As defined in "D. White, T Gibb, J Wall, P Westbrook, 'Assessment of Accuracy and Analysis Time of a Novel Device to Monitor Sleep and Breathing in the Home', Sleep, 18(2):115-126", the diagnostic agreement rules are as follows:

Agreement defined as:
AHI≥40 events per hour (e/hr) on both systems
If AHI<40 on PSG, AHI within 10 e/hr on both Overestimate of AHI defined as:
AHI 10 e/hr greater on system than PSG (both<40 e/hr)

Underestimate of AHI defined as:
AHI 10 e/hr less on system than PSG (both<40 e/hr)

Figure 22:
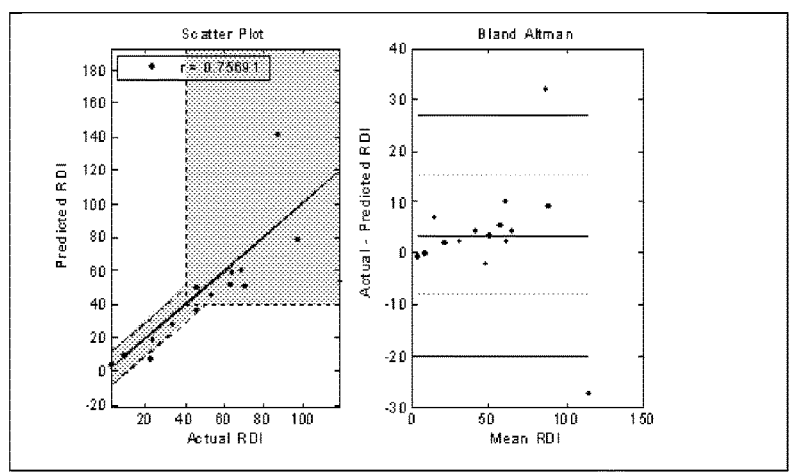
FIG. 22 shows an Example of diagnostic agreement in correlation plot.

The most recent correlation plots show the diagnostic agreement regions with dashed lines. FIG. 22 shows the diagnostic agreement region in grey. In the example plot, only 1 of the data points falls outside the diagnostic agreement range.

Kappa Agreement

Cohen's Kappa statistic provides the degree to which two judges concur in the respective classification of N items into k mutually exclusive categories—relative to that expected by chance. It is a "chance corrected proportional agreement". Unweighted Kappa assumes no relationship between events, Linear weighted Kappa assumes numeric relationship (e.g. 1 is closer to 2 than it is to 3). An example epoch-by-epoch confusion matrix of a system prediction that has 90% agreement (always predicts zero events per epoch) is shown below. As expected, the Kappa value for this matrix is 0. To the right of the matrix is a set of generally accepted interpretations of the ranges of Kappa values.

|     |   | System Prediction | | | |
| --- | --- | --- | --- | --- | --- |
|     |   | 0 | 1 | 2 | 3 |
| PSG | 0 | 8154 | 0 | 0 | 0 |
|     | 1 | 870 | 0 | 0 | 0 |
|     | 2 | 9 | 0 | 0 | 0 |

| kappa | Interpretation |
| --- | --- |
| <0 | No agreement |
| 0.0-0.19 | Poor agreement |
| 0.20-0.39 | Fair agreement |
| 0.40-0.59 | Moderate agreement |
| 0.60-0.79 | Substantial agreement |
| 0.80-1.00 | Almost perfect agreement |

Agreement Percent = 90.3%
Kappa = 0!

Validation Set Results

The validation set consists of 15 patients. We ran an analysis of the SPOC data from this validation set and developed predictions of RDI and events. At this point, scoring information on the patients was utilized to fully analyze the results.

The patient population in the validation set was more severe than in the training set. The mean RDI for the training set was 33 with 20% of the patients having an RDI>40, while the mean RDI for the validation set was 53 with 60% of the patients having an RDI>40. The scored RDI and the predicted RDI for each patient are shown below.

| SPOC RDI | RDI from Alice PSG Scoring Report |
| --- | --- |
| 3.9 | 2.4 |
| 8.8 | 8.6 |
| 7.2 | 21.5 |
| 18.9 | 23.1 |
| 28.6 | 33.1 |
| 49.6 | 45.4 |
| 36.9 | 45.7 |
| 46.3 | 53.2 |
| 51.7 | 62.1 |
| 58.9 | 63.4 |
| 59.8 | 68.8 |
| 50.2 | 70.1 |
| 141.8 | 87.1 |
| 78.8 | 96.8 |
| 54.5 | 118.6 |

Figure 23:
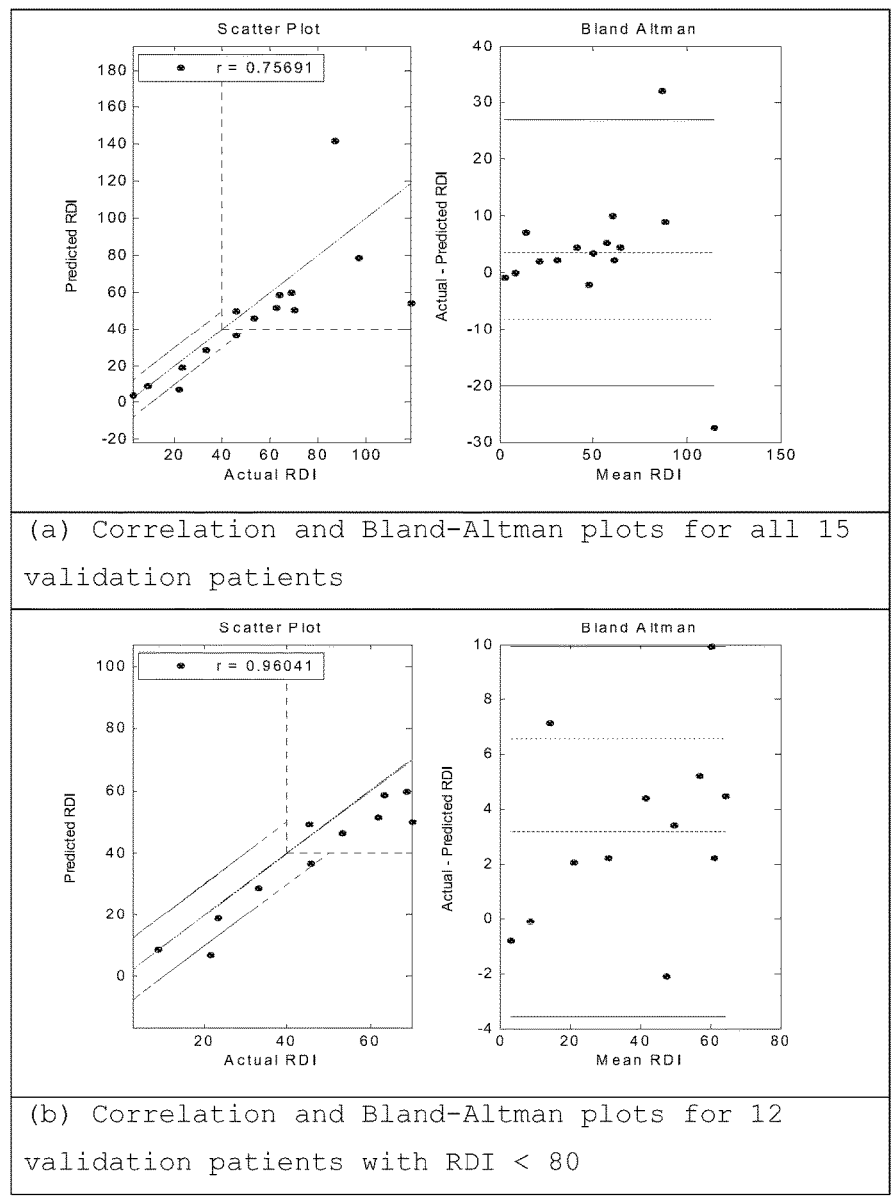
FIG. 23 shows validation results for the SPOC model: (a) Correlation and Bland-Altman plots for all 15 validation patients; (b) Correlation and Bland-Altman plots for 12 validation patients with RDI<80.

Although the population was somewhat different than the training set, the SPOC algorithms still performed quite well. The system correctly classified all severe (RDI>40) patients as severe. Although the RDI correlation is lower than in the training set, this was driven by two outliers with high RDI values (RDI>80). As shown in FIG. 23 the correlation coefficient for all 15 patients was 0.76 (bias=3, precision=10), while the correlation coefficient for patients with RDI<80 is 0.96 with a bias of 3 and precision of 3. The plots also show a diagnostic agreement of 93% missing only on SPOC-22 where the predicted value was 7 and the scored RDI was 20.

The table below shows the epoch-by-epoch analysis of the number of events. The Kappa statistic for the validation set was 0.47 which is slightly higher than the training set.

|     |   | System Number of Events | | | |
| --- | --- | --- | --- | --- | --- |
|     |   | 0 | 1 | 2 | 3 |
| PSG System | 0 | 7064 | 1364 | 31 | 0 |
| Number of | 1 | 961 | 1969 | 18 | 1 |
|     | 2 | 34 | 61 | 3 | 0 |

With only 2 patients in the validation set having an RDI<20 and both of them being less than 10, the ROC curves and AUC for RDI>10, 15, and 20 were all identical. The AUC was excellent at 0.96. The ROC for all three are shown in FIG. 24.

As discussed above with the AUCs for various RDIs, the AUC analysis with ODI in the validation set is of questionable validity due to the fact that only 2 patients have RDIs less than 20. The table of ODIs versus PSG RDIs is shown below.

| SPOC ODI | PSG RDI |
|---|---|
| 0.00 | 2.40 |
| 0.93 | 8.60 |
| 6.95 | 21.50 |
| 5.96 | 23.10 |
| 3.87 | 33.10 |
| 21.79 | 45.40 |
| 1.66 | 45.70 |
| 29.22 | 53.20 |
| 24.33 | 62.10 |
| 28.55 | 63.40 |
| 37.21 | 68.80 |
| 16.08 | 70.10 |
| 18.92 | 87.10 |
| 51.87 | 96.80 |
| 37.67 | 118.60 |

Figure 24:
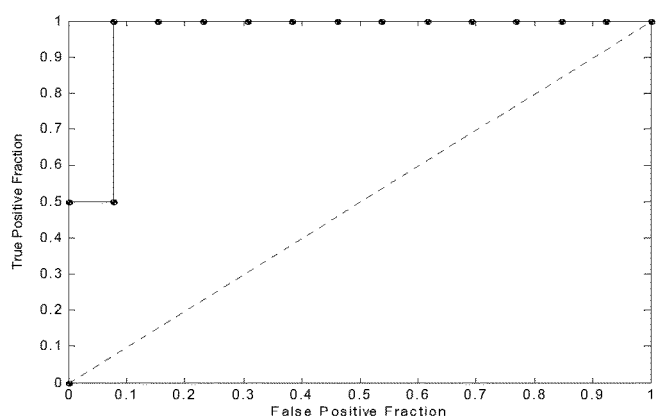
FIG. 24 shows ROC curve for validation set. All three curves, RDI>10, 15, and 20 are identical.
Figure 25:
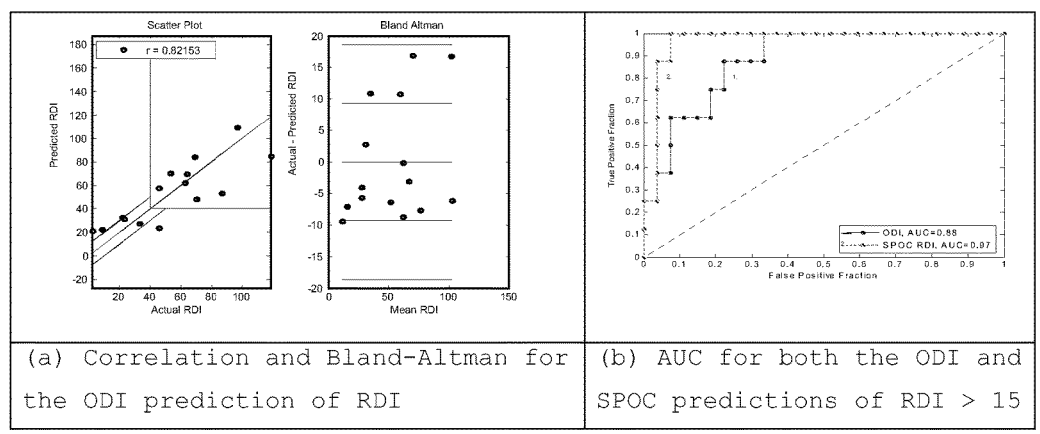
FIG. 25 shows the performance of ODI model of RDI: (a) Correlation and Bland-Altman for the ODI prediction of RDI; (b) AUC for both the ODI and SPOC predictions of RDI>15.

The correlation plot for ODI prediction of RDI (after linear scaling) are shown in FIG. 24. The correlation coefficient is only r=0.82 and the precision is 10 (after linear adjustment, the bias is 0 by definition). The ROC curves using both RDI and SPOC prediction for RDI>15 on all 35 patients (to get a better distribution of low RDI patients) is shown in FIG. 25. Notice that the SPOC RDI has an AUC of 0.97 whereas the ODI AUC is 0.88.

Review of Outliers

In the validation set, there were 3 patients we considered to be outliers: SPOC-22, SPOC-24, and SPOC-26 (although SPOC-24 and SPOC-26 were correctly classified as "severe"). The table of predicted versus manually scored RDIs in the validation set is shown below, with the outliers highlighted.

| Patient | PSG RDI | Reported SPOC RDI |
|---|---|---|
| SPOC-22 | 21.5 | 7.2 |
| SPOC-23 | 70.1 | 50.2 |
| SPOC-24 | 118.6 | 54.5 |
| SPOC-25 | 68.8 | 59.8 |
| SPOC-26 | 87.1 | 141.8 |
| SPOC-27 | 45.7 | 36.9 |
| SPOC-28 | 8.6 | 8.8 |
| SPOC-29 | 53.2 | 46.3 |
| SPOC-30 | 33.1 | 28.6 |
| SPOC-31 | 45.4 | 49.6 |
| SPOC-33 | 62.1 | 51.7 |
| SPOC-34 | 96.8 | 78.8 |
| SPOC-35 | 23.1 | 18.9 |
| SPOC-36 | 63.4 | 58.9 |
| SPOC-37 | 2.4 | 3.9 |

In our preliminary report of validation set results, we under predicted RDI for two of these (22 and 24) and over-predicted the RDI of SPOC-26. A closer look at SPOC-26 showed that there were four hours of time in which the pleth signal was "disconnected". This type of error was not being detected by our algorithm at the time of testing. After correcting for this disconnection, however, the RDI estimate for SPOC-26 drops from 141 to 52 (although there were some disconnections in the other patients, none were long enough to significantly affect the scoring).

In analyzing the under-prediction that is prevalent for the high RDI patients, there appears to be two primary causes: (1) the SPOC system was trained on low and moderate patients in order to produce better diagnostic accuracy, and (2) there was a significant difference between sleep time and study time in a few patients.

In our models, a good example of how training on low and moderate patients affects the scoring of the severe patients is in calculating the baseline. Each parameter (such as DC Drop and $SpO_2$ Drop) calculates a "baseline" from which to compare the current breath. For patients with many events, this baseline is artificially more "severe" on average, which causes the current breath to seem less "severe" and allows a number of events to just miss their "threshold". As described previously, in the Nasal Pressure Drop parameter we utilized two separate baseline calculations—one for moderate and mild patients and one for severe patients. With the increased number of severe patients in the validation set, it now appears that this methodology should be utilized more frequently in our models. Another approach is to create separate models for severe and non-severe patients (the SPOC system has proven its ability to determine the difference). Of course, an important consideration is whether fixing the RDI of severe patients is even an important issue if this device is to be used only for "screening".

The second source of under prediction is the lack of accurate sleep scoring in the SPOC data. This issue is particularly relevant for SPOC-22 which is moderate and was our only diagnostic disagreement. The SPOC prediction of RDI was 7.2 whereas the PSG RDI was 21.5. However, patient 22 was awake for over half the night. During this waking period, the SPOC system predicted an RDI of close to zero causing the overall RDI to be artificially low. SPOC-22 was rather extreme in his wake time vs. sleep time, taking 86 minutes to fall asleep whereas the other patients averaged only 14 minutes to fall asleep. With a more appropriate estimate of sleep-time, the SPOC RDI prediction for patient 22 would have been 14, which would have been a diagnostic agreement. Improving sleep time estimates, if possible, would appear to be an effective means of improving the RDI prediction for mild and moderate patients.

Conclusion

This document has summarized the efforts and results obtained from this SPCDS project. The data driven approach has created a system that appears to be robust to differences in patient population and performs well relative to other systems on the market. The system uses a unique combination of nasal pressure, saturation, and plethysmography parameters and each of the 4 parameters contributes unique information that is utilized by the system. Although there were a few outliers in the validation set that produced a lower than expected correlation with RDI, these outliers are largely caused by two factors: (1) the difference between sleep time and valid data time (our surrogate for sleep), and (2) our focus on correctly discriminating mild and moderate patients. The largest outliers were limited to the very high RDI patients (RDI>80) and the RDI correlation for patients with RDI<80 was 0.96. Even with the sleep-time induced underestimates, the White/Westbrook diagnostic agreement was 93%. With compensation for this sleep time disparity, the diagnostic agreement was 100%.

In the near future, we propose to continue development of the algorithms and primarily focus on three issues:
1. Detection of sleep and awake time
2. Detection of central vs. obstructive apnea
3. Use of dual (mild vs. severe) models or more complex models with the larger training and validation sets.

Example 14

Central Source Site PPG Signal Acquisition, Measurement of Expired CO2 and Provision of Positive Pressure Ventilation In a scenario where it is necessary to minimally sedate a subject, e.g. for a colonoscopy, propofol (alone or in combination with other pharmacologically active agents, can be administered intravenously. This can be under the control of a trained anaesthesiologist, under the at least partial control of a subject (e.g. by testing ability of the subject to perceive a signal and the subject activating a propofol infusion pump on perceiving the signal), under automated control, or in a system comprising various elements of each of these.

The present example of acquiring patient physiological data, acquired at a central source site of a patient, and, utilizing information derivable from that signal in the control of delivery of medication or fluids to a subject in need of such treatment. This specific example provides a photoplesmythographic solution, referred to for convenience herein as PPGcare™, whereby, during delivery of anesthetic agent to a subject, a first signal is acquired at a central source site of the subject and is monitored for evidence derivable from the first signal which is known to be indicative of hypoventilation. On detection of evidence of hypoventilation, a second signal is generated which is sent to a controller to (i) alert staff of the identified hypoventilation; (ii) to automatically initiate positive pressure ventilation of the subject; and, if the positive pressure ventilation does not produce evidence of resolution of hypoventilation in the subject, to (iii) decrease or stop delivery of anesthetic agent. In a sophisticated embodiment implementing this exemplary application, a central controller extracts the information required from the central source site photoplethysmography signal to acquire the venous impedance signal from which evidence of increased breathing effort or decreased breathing rate or regularity is extracted. The controller, then, based on the evidence, and in a preferred embodiment, after confirming that no contradictory signal is being acquired from any other sensor, limits or turns off delivery of the anesthetic agent unless/until the evidence of hypoventilation is resolved or trained personnel intervene.

Figure 26A:
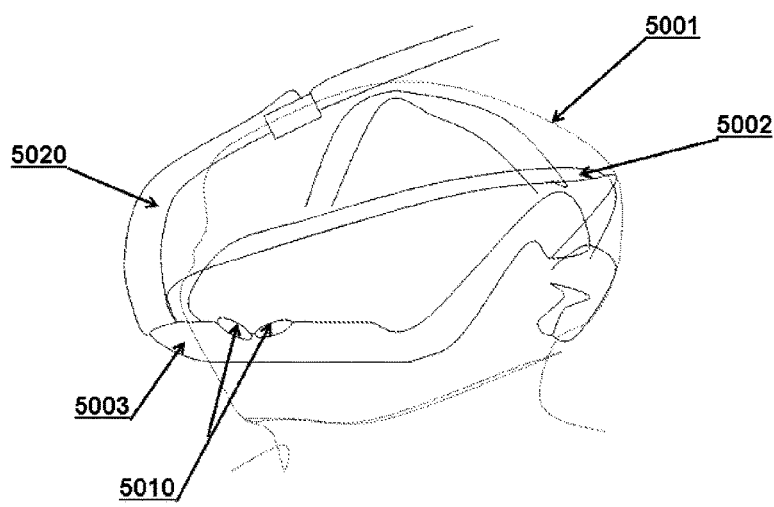
FIG. 26A, B, C show an embodiment of an assembly to provide positive pressure ventilation and delivery of pharmacologically active agents while acquiring exhaled breath information, as needed, based on signal acquired from a subject.

The best mode for carrying out this aspect of the invention can be appreciated by review of FIG. 26. In FIG. 26A, there is shown a system according to this invention, 5000, operatively adhered to a subject 5001, shown in outline. A harness system 5002 is shown for keeping an air exchange housing 5003 of a PPGcare™ unit 5000 in proper position and alignment on the face of the subject 5001. As will be seen from the further description below, the air exchange housing 5003 comprises means for sealingly measuring $CO_2$ in exhaled air, means 5010 for provision of positive pressure ventilation of the subject 5000, a source of gas, which is considered a fluid for purposes of this invention, 5020, which may include a source of high oxygen gas, ordinary breathing air, inhalational anesthetic or other volatile agents and the like. The source of gas 5020 is under control of the PPGcare™ system of this invention, such that, upon detection of hypoventilation, PPGcare™ initiates positive pressure ventilation, preferably with oxygen enriched air.

Figure 26B:
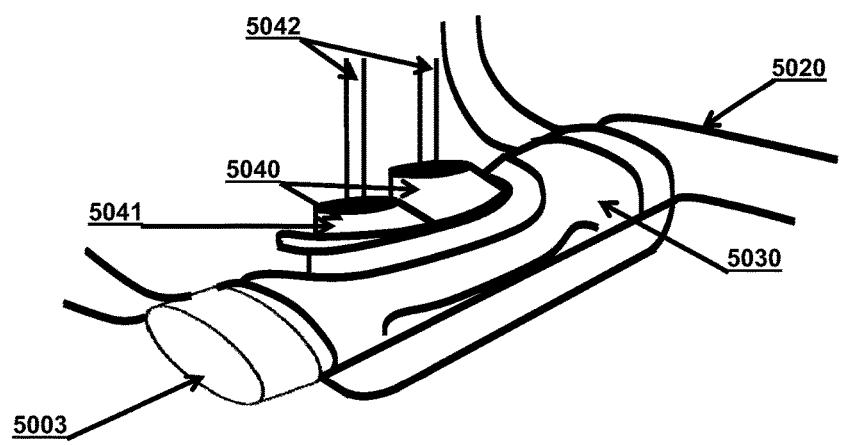

Referring now to FIG. 26*b*, there is shown a detail of one representation of an Air Exchange Housing 5003 as shown in FIG. 26A, with the source of gas 5020 connected to a housing unit 5030 into which positive pressure gas can be infused when/if the PPGcare™ controller receives a signal indicating subject hypoventilation. For sealingly engaging with the nares of the subject, there are provided two "nasal pillows" 5040, each comprising a nasal seal 5041 running through which there is provided any number of tubes, channels or the like 5042 for provision of any or all of the elements of the various aspects of this invention, including but not limited to: means for measuring exhaled $CO_2$, e.g. a capnometer probe, electrical connections for a Central Source Site PPG probe, (i.e. both for at least one photodiode or the like and at least one photodetector, or the like, for which wavelengths of illumination and detection may be multiplexed, according to methods known in the art), to acquire photoplethysmographic signals, pulse oximetry signals or both, means for delivery of pharmacologic agent(s) or fluids to the nasal septum, as described in the full patent disclosure.

Figure 26C:
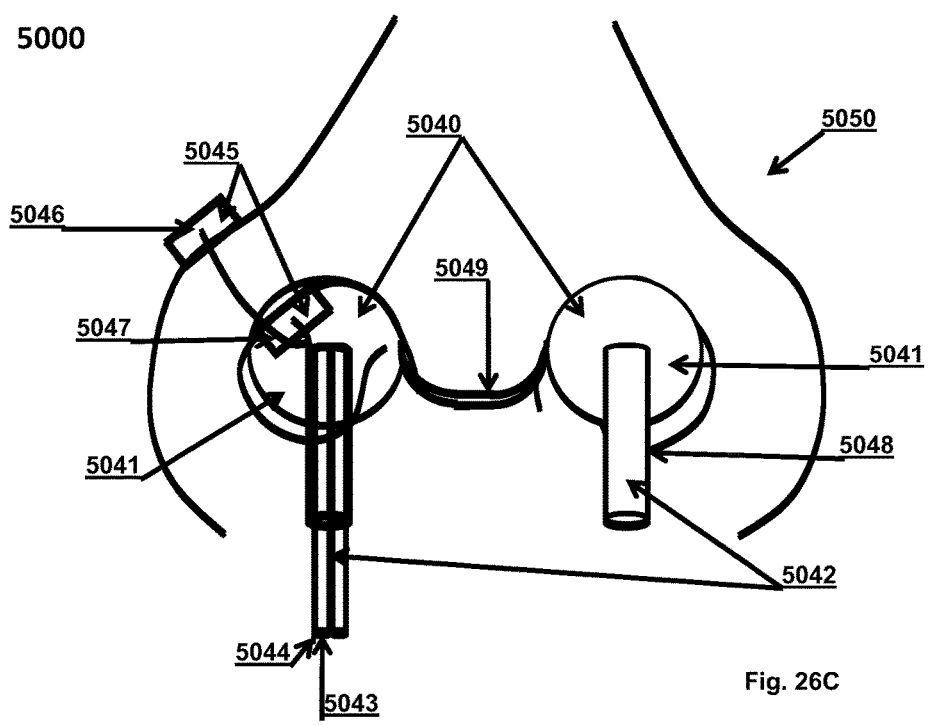

In FIG. 26C, there is provided a detailed, from below view, of one embodiment according to this invention of a nasal interface of the nasal interface unit 5050 which provides a representation of various elements of the PPGcare™ system 5000, method and apparatus, from this rather unique angle of the human anatomy. Looking upward into the nares of a subject, there is shown two "nasal pillows" 5040, each comprising a nasal seal 5041 running through which there is provided any number of tubes, channels or the like 5042 for provision of any or all of the elements of the various aspects of this invention, including but not limited to: means for measuring exhaled $CO_2$, e.g. a capnometer probe 5043, electrical connections for a Central Source Site PPG probe 5044, (i.e. both for at least one photodiode 5046 or the like and at least one photodetector 5047, or the like, for which wavelengths of illumination and detection may be multiplexed, according to methods known in the art), to acquire photoplethysmographic signals, pulse oximetry signals or both, and/or means 5048 for delivery of pharmacologic agent(s) or fluids to the nasal septum, as described elsewhere in this application. The assembly of different elements described in this example may be such that each element with respect to each other element is held in good registration with the physiology of the subject by an alignment member, 5049, for example, which registers the assembly to the nasal septum. Each of the elements may be likewise held in pliant registration with each other element of the system and in relation to the alignment member 5049. Referring back to other figures, examples and disclosure provided herein, one skilled in the art will appreciate how an infusion apparatus may be controlled by acquisition of PPG signal from a central source site to measure subject physiologic parameters, and to control, on the basis of analysis of the central source site PPG signal, infusion of anesthetic, other pharmacologically active agents and/or fluids.

Example 15

PSG and PPG

In this study, 35 patients were examined from a sleep study in which a full array of polysomnography (PSG) parameters were collected alongside photoplethysmography (PPG) parameters collected by a single sensor on the alar site. The goal was to determine whether respiratory rate and IE ratio could be accurate determined using PPG alone.

Results:

In the 35 patients studied respiratory rate was reliably detected using PPG ($r^2=0.88$). IE ratio, however, could not be determined through PPG alone, however. Simulations show that the process used to filter out the high frequency or cardiac component from PPG is responsible for removing IE ratio information from the signal. Because the cardiac component is by the far the strongest component of the signal, separating IE ratio from PPG may be impossible.

Respiratory Rate

Figure 27:
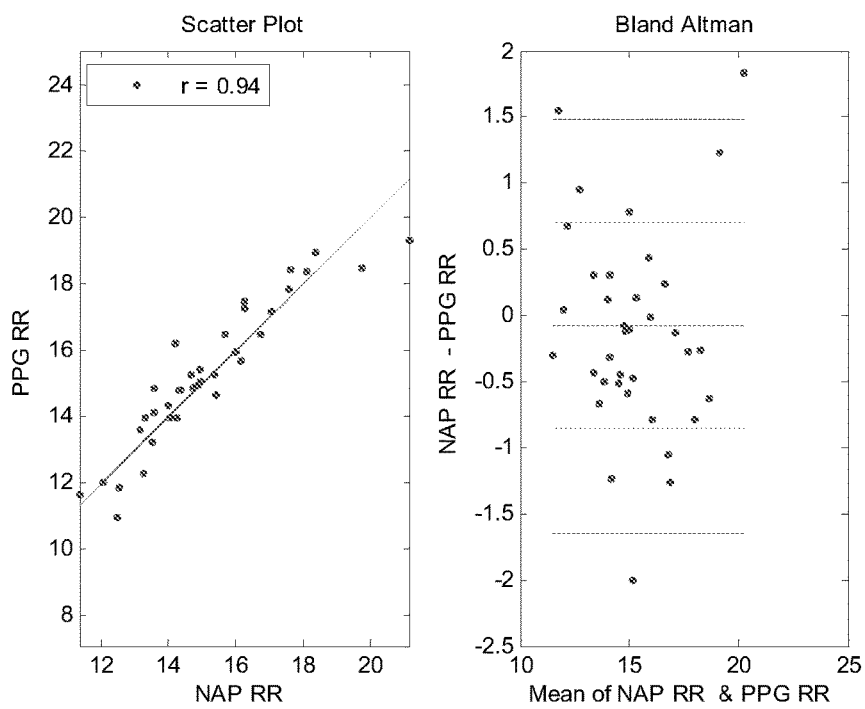
FIG. 27: The left panel shows the correlation between average respiratory rate as determined by nasal pressure (NAP) and PPG (r2=0.88). The bland-altman is shown in the right panel.

An algorithm to reliably remove respiratory rate from the IR and RED PPG signals has been developed. This algorithm processes the signal to effectively remove the cardiac component and DC shifts unrelated to respiratory effort. Over the course of a sleep study, this respiratory component effectively tracks the respiratory rate as determined by the nasal pressure. FIG. 27 shows how the PPG tracks the average respiratory rate of a sleeping patient.

Figure 28:
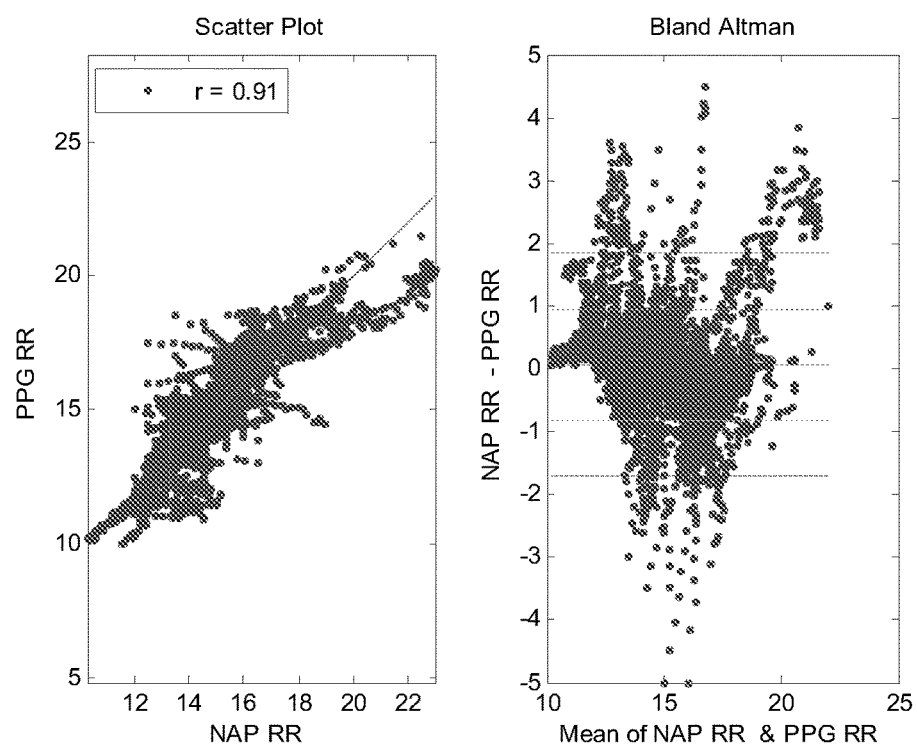

In addition to the long term average, a more short term respiratory rate was tested. FIG. 28 shows smaller one minute regions taken from the 35 patients. FIG. 28 shows 4,473 one minute regions of data. These regions were selected based on the following criteria:
1. Nasal pressure was not zero and was not saturated
2. PPG SaO2 was above 75%
3. No LED changes
4. IR and RED channels agreed on heart rate and respiratory rate It should be noted here that even within these regions, nasal pressure is not 100% reliable and sections of noise exist in the NAP signal that the above criteria did not disqualify.

IE Ratio

Figure 29:
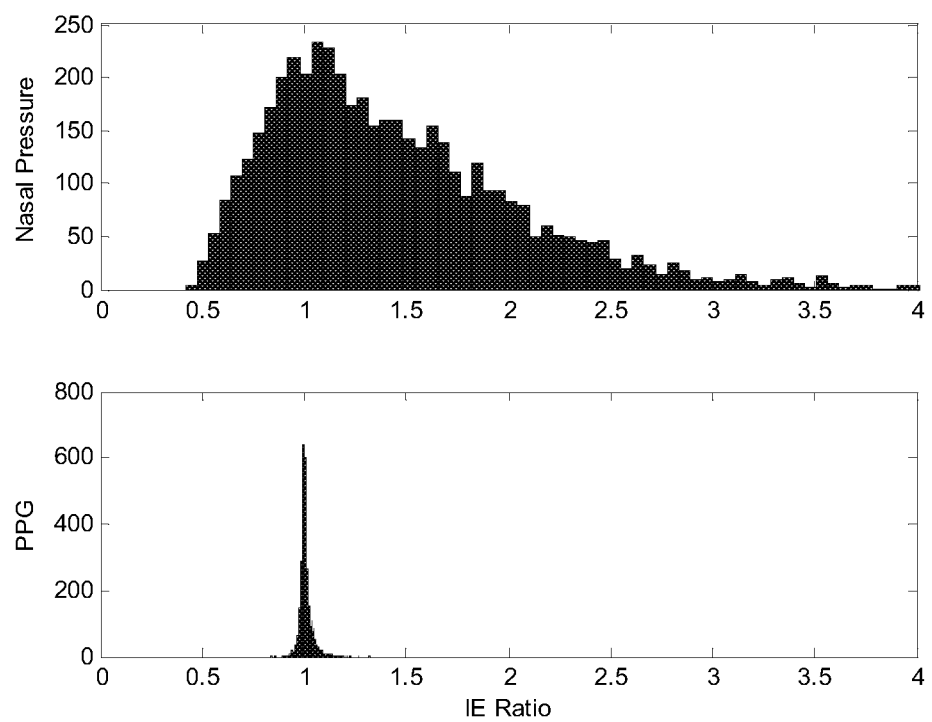
FIG. 29: The top panel shows a histogram of IE ratios calculated from 4,473 one minute regions using nasal pressure. The bottom panel shows a histogram of IE ratios from the same regions using PPG.

IE ratio as calculated by PPG did not correlate reliably with IE ratio calculated using NAP signal. The top panel of FIG. 29 shows a histogram of IE ratios calculated from one minute regions using the NAP signal. The bottom panel shows a histogram of IE ratios from the same regions calculated using the PPG signal. Whereas the NAP signal provides a wide spread of measured IE ratios, the IE ratios calculated from PPG are clustered around a 1:1.

Figure 30:
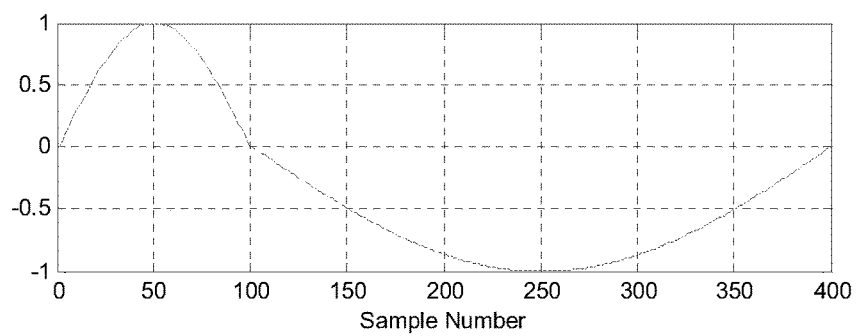
FIG. 30: Test signal with an IE ratio of 1:3 used in simulation study.
Figure 31:
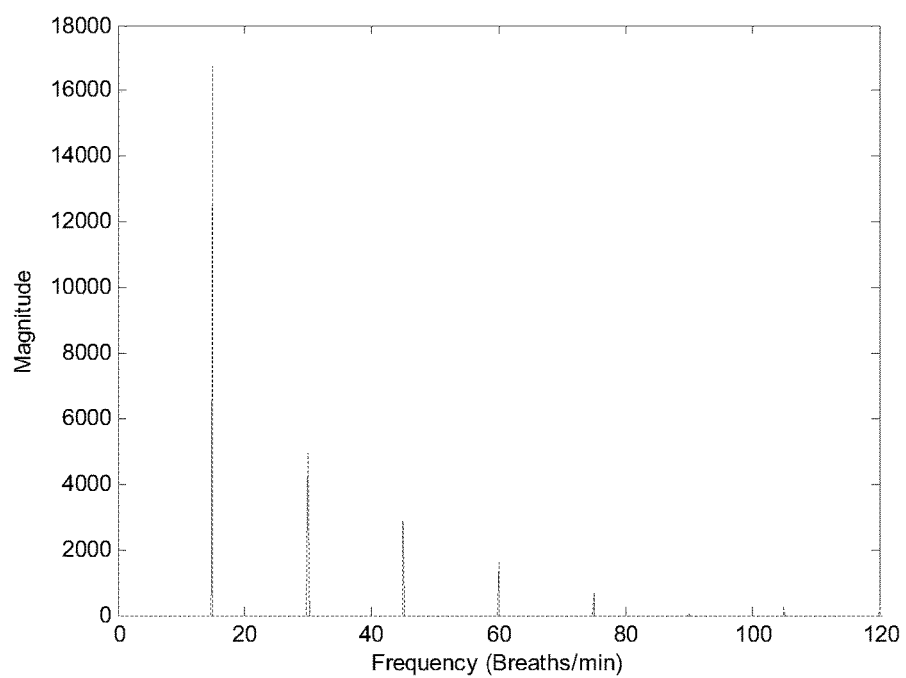
FIG. 31: Frequency spectrum of the test breath shown in FIG. 4.

A simulation was conducted to investigate the reason for the absence of IE ratio information in the PPG signal. A test signal was generate with an IE ratio of 1:3 as shown in FIG. 30. FIG. 31 shows the frequency spectrum of this test breath.

Figure 32:
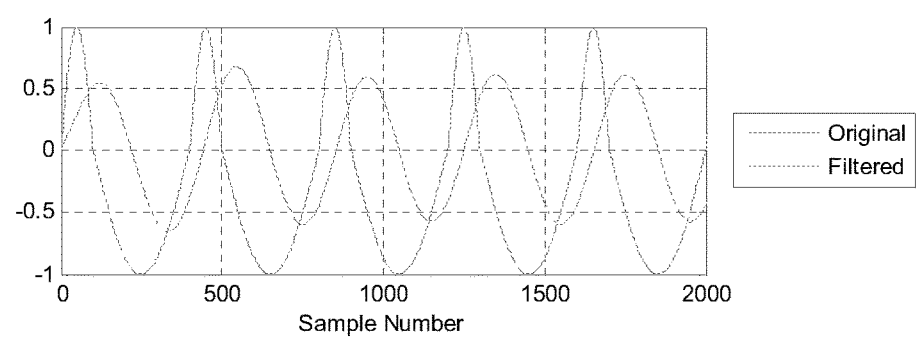
FIG. 32: The original test signal (blue) and the processed respiratory component (green) after the algorithm as been applied.

Although the fundamental breath rate of this test signal is 15 breaths/min (0.25 Hz), the uneven IE ratios creates energy at harmonic frequencies (30, 45, 60, and 75 breaths/min). These higher harmonics enter the range of frequencies affected by the cardiac component. The same filtering algorithm applied to the sleep study to extract the respiratory component from PPG was applied to this test signal. The resulting signal is shown in FIG. 32. FIG. 32 shows that because the bandpass filter for respiratory rate is tight to remove noise in adjacent frequency bands, the respiratory signal that remains is very close to sinusoidal (single frequency). This sinusoidal signal has very little IE ratio information remaining. Some strategies were tested to better separate the IE ratio from the PPG data in the sleep studies but thus far none have been successful. Other approaches exist, but this will require significantly more effort.

CONCLUSION

The PPG is a reliable independent channel to determine respiratory rate and can therefore be a good compliment or backup to nasal pressure. The IE ratio, however, is difficult to reliably extract from the PPG signal.

What is claimed is:

1. A system for monitoring and control for safe administration, reduction or cessation of administration of at least one of medication to a subject, comprising:
   (a) at least one photoplethysmography (PPG) sensor adapted to secure to a central source site of the subject;
   (b) an infusion pump for delivering the at least one medication to the subject, wherein the infusion pump comprises an infusion controller for increasing or decreasing flow of medication to the subject; and
   (c) an infusion pump agnostic safety device that is adapted to be deployed onto tubing adapted to deliver the at least one medication from the infusion pump to the subject, wherein the safety device comprises an occlusion apparatus and an occlusion controller, wherein the occlusion controller receives signals from the PPG sensor, calculates at least one respiratory parameter based on the signals from the PPG sensor, and if the at least one respiratory parameter is determined by the occlusion controller to be adverse, the occlusion controller directs the occlusion apparatus to partially or completely occlude the tubing
   wherein the infusion pump agnostic safety device only occludes the tubing in the event the occlusion controller determines that an adverse event has occurred.

2. The system of claim 1, wherein the at least one respiratory parameter comprises respiratory rate, respiratory effort, or both.

3. The system of claim 1, wherein the occlusion controller is further configured to initiate an alarm if the at least one respiratory parameter is determined by the occlusion controller to be adverse.

4. The system of claim 1, further comprising at least one additional sensor.

5. The system of claim 4, wherein the at least one additional sensor is selected from the group consisting of an electrocardiograph, a capnometer, a nasal pressure sensor and a nasal flow sensor.

6. The system of claim 4, wherein the occlusion controller sends signals to the occlusion apparatus to partially or completely occlude the tubing if an adverse parameter based on signals from the at least one additional sensor is detected.

7. The system of claim 1, wherein the infusion pump is a patient controlled anaesthesia (PCA) pump.

8. The system of claim 1, wherein the medication comprises at least one of an opioid, a benzodiazepine and propofol.

9. The system of claim 1, further comprising ventilation means for applying positive ventilation pressure to the subject upon receipt by the ventilation means of a control signal to initiate, increase or decrease ventilation.

10. The system of claim 9, wherein the control signal to initiate, increase or decrease ventilation is given to the ventilation means from the occlusion controller when at least one adverse respiratory parameter is determined by the controller.

11. The system of claim 1, wherein the central source site of the individual is the nasal septum or the nasal alar.

* * * * *